(12) United States Patent
Park et al.

(10) Patent No.: US 11,233,202 B2
(45) Date of Patent: Jan. 25, 2022

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si (KR)

(72) Inventors: Jonggwang Park, Ulsan (KR); Yun Suk Lee, Seongnam-si (KR); Kiho So, Cheonan-si (KR); Hyoung Keun Park, Chuncheon-si (KR); Yeonseok Jeong, Gangwon-do (KR); Yeon Hee Choi, Cheonan-si (KR); Jae-Taek Kwon, Cheonan-si (KR)

(73) Assignee: DUK SAN NEOLUX CO., LTD., Cheonan-si (KR)

(*) Notice: Subject to any disclaimer, the term of this patent is extended or adjusted under 35 U.S.C. 154(b) by 483 days.

(21) Appl. No.: 16/310,619

(22) PCT Filed: Apr. 25, 2017

(86) PCT No.: PCT/KR2017/004382
§ 371 (c)(1),
(2) Date: Dec. 17, 2018

(87) PCT Pub. No.: WO2017/217654
PCT Pub. Date: Dec. 21, 2017

(65) Prior Publication Data
US 2021/0226130 A1    Jul. 22, 2021

(51) Int. Cl.
*C07D 209/86*    (2006.01)
*H01L 51/00*    (2006.01)
(Continued)

(52) U.S. Cl.
CPC ........ *H01L 51/0061* (2013.01); *C07D 209/86* (2013.01); *C07D 401/10* (2013.01);
(Continued)

(58) Field of Classification Search
CPC .................................................. C07D 209/86
See application file for complete search history.

(56) References Cited

U.S. PATENT DOCUMENTS

2014/0209878 A1* 7/2014 Jung ................... H01L 51/0072
257/40

FOREIGN PATENT DOCUMENTS

| CN | 105051011 A | 11/2015 |
|----|-------------|---------|
| JP | 2005-154421 A | 6/2005 |

(Continued)

OTHER PUBLICATIONS

Computer-generated English-language translation of WO-2016153283-A1.*

(Continued)

*Primary Examiner* — Vu A Nguyen
(74) *Attorney, Agent, or Firm* — The PL Law Group, PLLC

(57) ABSTRACT

The present invention provides the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electronic device can be lowered, and the luminous efficiency and life time of the organic electronic device can be improved.

20 Claims, 1 Drawing Sheet

(51) Int. Cl.
  *H01L 51/50*      (2006.01)
  *C07D 401/10*     (2006.01)
  *C07D 409/12*     (2006.01)
  *C07D 409/14*     (2006.01)
  *C09K 11/06*      (2006.01)
  *H01L 51/05*      (2006.01)
  *H01L 51/42*      (2006.01)

(52) U.S. Cl.
  CPC ......... *C07D 409/12* (2013.01); *C07D 409/14* (2013.01); *C09K 11/06* (2013.01); *H01L 51/006* (2013.01); *C07B 2200/05* (2013.01); *C09K 2211/1018* (2013.01); *H01L 51/0052* (2013.01); *H01L 51/0067* (2013.01); *H01L 51/0072* (2013.01); *H01L 51/0074* (2013.01); *H01L 51/0504* (2013.01); *H01L 51/42* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

FOREIGN PATENT DOCUMENTS

| | | |
|---|---|---|
| JP | 4458361 B2 | 4/2010 |
| JP | 4589223 B2 | 12/2010 |
| JP | 4975318 B2 | 7/2012 |
| JP | 5032016 B2 | 9/2012 |
| JP | 5082356 B2 | 11/2012 |
| JP | 5085842 B2 | 11/2012 |
| JP | 5585044 B2 | 9/2014 |
| KR | 10-2014-0018789 A | 2/2014 |
| KR | 10-2014-0097935 A | 8/2014 |
| KR | 10-1462070 B1 | 11/2014 |
| KR | 10-2015-0112880 A | 10/2015 |
| KR | 10-1565039 B1 | 11/2015 |
| KR | 10-2016-0012895 A | 2/2016 |
| KR | 10-1627583 B1 | 6/2016 |
| KR | 10-1627584 B1 | 6/2016 |
| WO | WO-2016153283 A1 * 9/2016 ............ C07D 209/82 |
| WO | WO-2016175533 A2 * 11/2016 ............ C07D 333/76 |

OTHER PUBLICATIONS

Computer-generated English-language translation of WO-2016175533-A2.*
SciFinder Search (Year: 2021).*

* cited by examiner

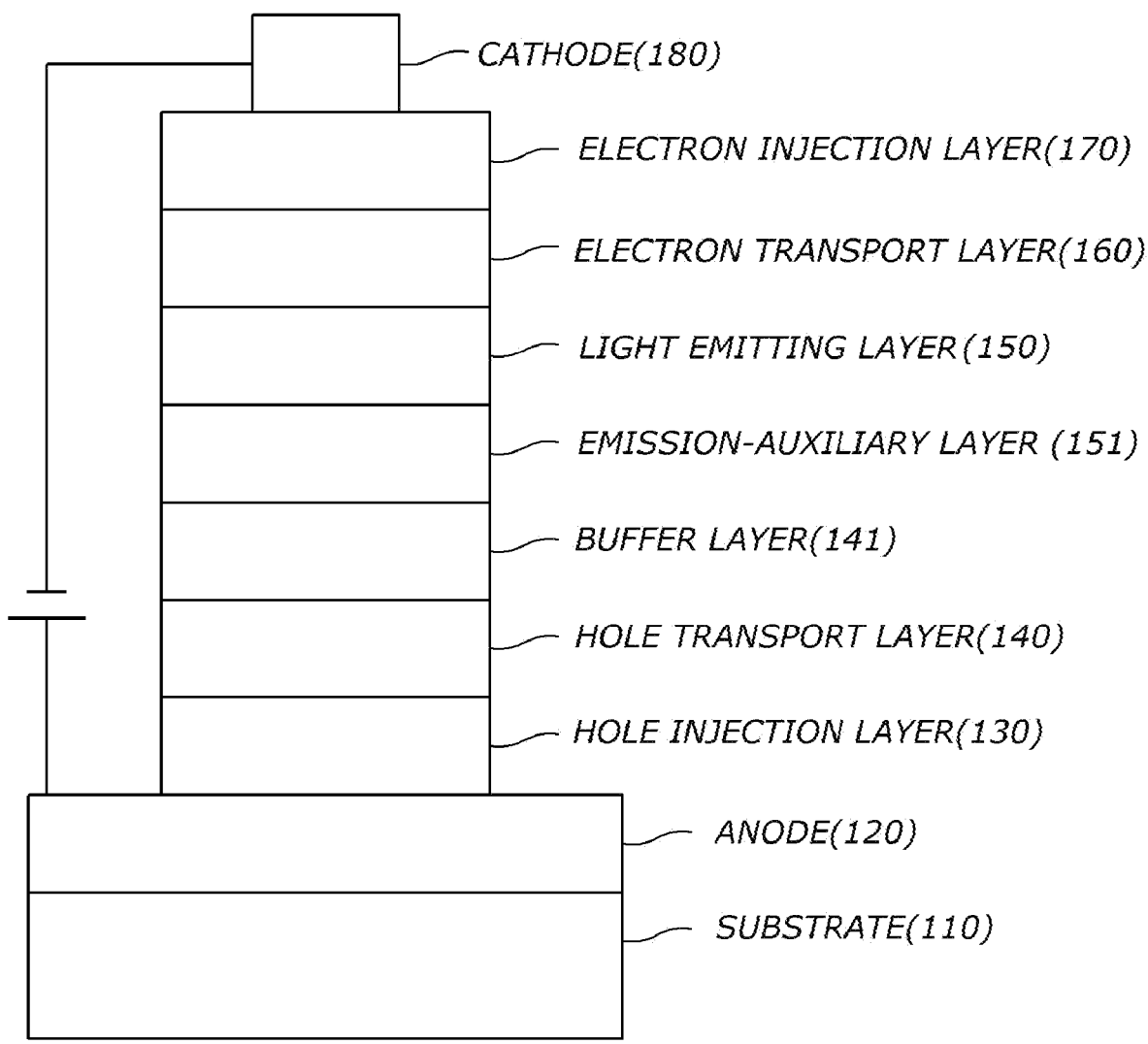

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2016-0075404, filed on Jun. 17, 2016, which is hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when energy levels and T1 values among the respective layers included in the organic material layer, inherent material properties (mobility, interfacial properties, etc.) and the like are optimal combination.

Further, an emission-auxiliary layer must be present between the hole transport layer and the light emitting layer in order to solve the problem of luminescence in the hole transport layer of recent organic electroluminescent devices, and it is time to develop different emission-auxiliary layers according to respective light emitting layers (R, G, B).

In general, an electron is transferred from an electron transport layer to a light emitting layer and a hole is transferred from a hole transport layer to the light emitting layer, as a result, an exciton is formed by the recombination of the electron and hole.

However, material used in a hole transport layer has a low T1 value because the material should have a low HOMO value. As a result, the exciton generated in the light emitting layer is transferred to the interface of the hole transport layer or the hole transport layer, and thereby emitting light at the interface of the hole transport layer or a charge unbalance in the light-emitting layer.

When light is emitted from the interface of the hole transporting layer, the color purity and efficiency of the organic electronic element are lowered and the lifetime is shortened. Therefore, it is strongly desired to develop materials for the emission-auxiliary layer having a HOMO level between the HOMO energy level of the hole transporting layer and the HOMO energy level of the light emitting layer, a high T1 energy value and a hole mobility within a suitable driving voltage range (within a driving voltage range of blue element of a full device).

However, this cannot be achieved simply by the structural properties of the core of the emission-auxiliary layer material. An element having a high efficiency and a long life span can be realized when the characteristics of core and sub-substituents of the emission-auxiliary layer material, the proper combination of the emission-auxiliary layer and the hole transport layer, and the proper combination of the emission-auxiliary layer and the light emitting layer.

On the other hand, it is also necessary to develop a hole injection/transport layer materials and an emission-auxiliary layer material having stable characteristics against Joule heat generated, that is, a high glass transition temperature when the element is driven.

It has been reported that the low glass transition temperature of the hole transporting layer and the emission-auxiliary layer material lowers the uniformity of the surface when the device is driven and causes the material to deform due to heat generated when the device is driven, as a result, the life span of the device is greatly affected.

Amine compound comprising a carbazole is very different in properties depending on the material structure, and thus it applies to a hole transport layer and an emission-auxiliary layer as material of an organic material layer. In particular, band gap (HOMO, LUMO), electrical properties, chemical properties, physical properties and the like are depending on the bonding position, number and the introduction of various linker of an amine group bonded to carbazole, and thus development to apply it to the hole transport layer and an emission-auxiliary layer has been proceeding so far.

As a representative example, the following Patent Documents 1 to 11 disclose the performance of an amine compound including a carbazole.

1. JP 2005-154421 A
2. JP 4458361 B2
3. JP 5085842 B2
4. JP 4589223 B2
5. JP 5032016 B2
6. JP 4975318 B2
7. JP 5082356 B2
8. JP 5585044 B2
9. KR 10-1462070 B1
10. KR 10-1627583 B1
11. KR 10-1627584 B1

Patent Documents 1 to 7 disclose a structure in which amines are bonded at the 3-position of carbazole. Since the 3-position of the carbazole is the para position of the nitrogen atom being an electron donor, the amino group substituted at the 3-position is activated by the nitrogen atom of the carbazole ring. That is, the compound having an amino group introduced into the 3-position of the carbazole has a lower ionization potential than an ordinary amine compound. Therefore, the hole injection barrier in the light emitting layer becomes large, which causes a problem that the driving voltage increases when the device is driven.

Patent Document 8 discloses a structure in which an amine is bonded at the 2-position of carbazole, and it is reported that the amine is likely to have a more appropriate ionization potential when the amine is bonded at 2-position than 3-position of the carbazole. However, it discloses only a use example for material in which a carbazole and an amine are directly bonded, and a performance characteristic due to introduction of linker between carbazole and amine cannot be confirmed by Patent Document 8.

Patent Documents 9 to 11 disclose a structure in which a linking group is introduced between a carbazole and an amine and is bonded to a 2-position of the carbazole, and Patent Documents 9 to 11 disclose the performance according to the type of the linker and the type of bonding (linear, non-linear).

However, it is still required to develop a hole transport layer and an emission-auxiliary layer materials for an organic electric device having high light emitting efficiency while exhibiting stability such as durability and heat resistance characteristics in process of the device deposition. Therefore, it is necessary to develop materials in the direction of improving luminous efficiency and lifetime by introducing various linking groups and amine substituents while increasing the number of amines in existing skeletons based on the compound disclosed in the prior art.

Object, Technical Solution and Effects of the Invention

The object of the present invention is to provide a compound having the efficient electron blocking ability and the hole transporting ability, the high luminous efficiency and the low driving voltage of the device, and the high heat resistance, capable of improving color purity and lifespan, an organic electric element comprising the same, and an electronic device thereof.

In accordance with an aspect of the present invention, the compound represented by the following formula is provided.

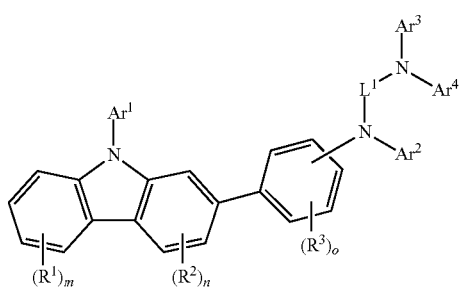

In another aspect of the present invention, organic electric element comprising the compound represented by the above formula and an electronic device including the organic electric element are provided.

According to the present invention, by using a specific compound having the carbazole core and the compound in which the kind of the amine group, the bonding position of the amine group, and the number of amine groups are specified, the hole transfer ability and the thermal stability of the organic electric device can be improved, and it has a high HOMO energy level, a high T1 value and a high refractive index, which are easy to achieve charge balance in the light emitting layer, and thus the luminous efficiency, the heat resistance, lifetime and the like the organic electric device can be improved and the driving voltage is lowered.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), bromine (Br), chlorine (Cl), or iodine (I).

Unless otherwise stated, the term "alkyl" or "alkyl group" as used herein has a single bond of 1 to 60 carbon atoms, and means the saturated aliphatic functional radicals including a linear alkyl group, a branched chain alkyl group, a cycloalkyl group (alicyclic), a cycloalkyl group substituted with an alkyl group and an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an oxygen radical attached to an alkyl group, but not limited to, and has 1 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises the case where R and R' are bonded to each other to form the spiro compound together with the carbon to which they are bonded.

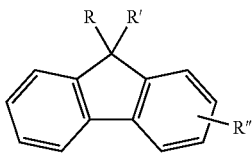

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may comprise a ring including $SO_2$ instead of carbon consisting of a ring. For example, "heterocyclic group" includes the following compound.

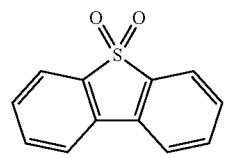 [SMILES: O=S1(=O)c2ccccc2-c2ccccc21]

The term "ring" as used herein means, a monocyclic and polycyclic, an aliphatic ring and heterocyclic group containing at least one heteroatom, and an aromatic ring and a non-aromatic ring.

The term "polycyclic ring" as used herein may comprise ring assemblies such as biphenyl and terphenyl, fused polycyclic system and a spiro compound, an aromatic ring and a non-aromatic ring, and an aliphatic ring and heterocyclic group containing at least one heteroatom.

The term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

The term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or a combination thereof.

The term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, a fluorenyl group, and a $C_2$-$C_{20}$ heterocyclic group containing at least one heteroatom selected from the group consisting of O, N, S, Si, and P.

A 'group name' comprised in an aryl group, an arylene group, a heterocyclic group and the like as example of each symbol and a substituent as used herein may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

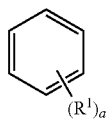

Wherein, when a is an integer of zero, the substituent R¹ is absent, that is, hydrogen atoms are bonded to all the carbon constituting the benzene ring, and chemical formulas or compounds may be written without explicitly describing the hydrogen. In addition, one substituent R¹ is bonded to any carbon of the carbons forming the benzene ring when "a" is an integer of 1. When "a" is an integer of 2 or 3, for example, substituents R¹s are bonded to the carbon of the benzene ring as followings. Also, substituents R¹s are bonded to the carbon of the benzene ring when "a" is an integer of 4 to 6 in a similar manner. Further, when "a" is an integer of 2 or more, R¹s may be the same or different from each other.

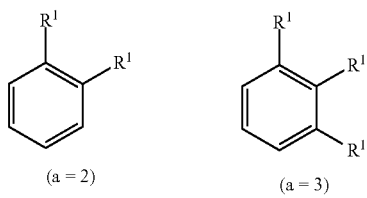

The FIG. illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, the electron transport-auxiliary layer, a buffer layer 141, etc., the electron transport layer 160 or the like may serve as the hole blocking layer, and a hole transport layer 140 and an electron transport layer 160 are each formed as one or more layers.

Although not shown, the organic electric element according to an embodiment of the present invention may further include a protective layer or a layer (Capping layer) for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170, as host or dopant of a light emitting layer 150, or as a material of a layer for improving luminous efficiency. For example, the inventive compound may be used as material of the light emitting layer 150, the hole transport layer 140 and/or the emission-auxiliary layer 151.

On the other hand, even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and T₁ values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B). On the other hand, even if the core of an emission-auxiliary layer is similar, it is very difficult to infer the characteristics of an emission-auxiliary layer because it is necessary to grasp the correlation between the emission-auxiliary layer and a hole transport layer and a light emitting layer (host).

Therefore, according to the present invention, energy level and T₁ value between the respective layers of the organic material layer, inherent material properties (mobility, interfacial properties, etc.) and the like can be optimized by forming a hole transport layer and/or an emission-auxiliary layer with the compound represented by the Formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

<Formula 1>

In the formula 1, each of symbols may be defined as follows.

$Ar^1$ to $Ar^4$ are each independently selected from the group consisting of a $C_6$-$C_{60}$ aryl group, a $C_2$-$C_{60}$ heterocyclic group containing at least one heteroatom selected from the group consisting of O, N, S, Si, and P, a fluorenyl group, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, with the proviso that a triphenylene group is excluded from $Ar^2$ and a carbazole group is excluded from $Ar^3$ and $Ar^4$.

Preferably, at least one of $Ar^1$ to $Ar^4$ is represented by the following Formula 5:

<Formula 5>

In the formula 5, each of symbols may be defined as follows, and "*" indicates the bonding position.

Y is S, O or $C(R^d)(R^e)$, wherein $R^d$ and $R^e$ are each independently selected from the group consisting of a $C_6$-$C_{20}$ aryl group, a fluorenyl group, a $C_2$-$C_{20}$ heterocyclic group containing at least one heteroatom selected from the group consisting of O, N, S, Si, and P, a fused ring group of a $C_3$-$C_{20}$ aliphatic ring and a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

$R^6$ and $R^7$ are each independently selected from the group consisting of a $C_6$-$C_{20}$ aryl group, a fluorenyl group, a $C_2$-$C_{20}$ heterocyclic group containing at least one heteroatom selected from the group consisting of O, N, S, Si, and P, a fused ring group of a $C_3$-$C_{20}$ aliphatic ring and a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, h is an integer of 0 to 4, g is an integer of 0 to 3, and plural $R^6$s and plural $R^7$s are each the same or different from each other where h and g are each an integer of 2 or more.

In addition, when at least one of $Ar^1$ to $Ar^4$ in Formula 1 is the Formula 5, preferably, the Formula 5 is one of the following Formulas 1-1 to 1-3, more preferably, Y in the formula 5 is S.

<Formula 1-1>

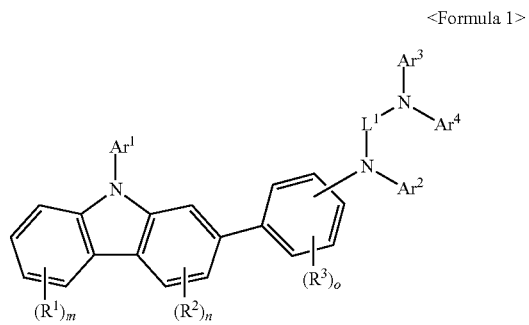

<Formula 1-2>

-continued

<Formula 1-3>

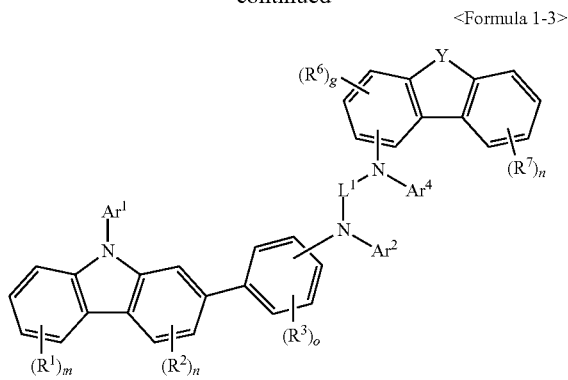

In the above Formulas 1-1 to 1-3, the symbols such as $Ar^1$ to $Ar^4$, $R^1$ to $R^3$, $R^6$, $R^7$, $L^1$, m, n, o, g, h and the like are the same as defined in Formula 1.

Where $Ar^1$ is an aryl group, $Ar^1$ may be preferably a $C_6$-$C_{30}$ aryl group, more preferably a $C_6$-$C_{18}$ aryl group, for example, phenyl, naphthyl, biphenyl, terphenyl, phenanthryl, triphenylene or the like; when $Ar^1$ is a heterocyclic group, $Ar^1$ may be preferably a $C_2$-$C_{30}$ heterocyclic group, more preferably a $C_2$-$C_{12}$ heterocyclic group, for example, dibenzothiophene, carbazole, dibenzofuran or the like; when $Ar^1$ is a fluorenyl group, $Ar^1$ may be, for example, 9,9-dimethyl-9H-fluorene.

When $Ar^2$ is an aryl group, $Ar^2$ may be preferably a $C_6$-$C_{30}$ aryl group, more preferably a $C_6$-$C_{14}$ aryl group, for example, phenyl, naphthyl, biphenyl, phenanthryl or the like, but triphenylene is excluded from the aryl group; when $Ar^2$ is a heterocyclic group, $Ar^2$ may be preferably a $C_2$-$C_{30}$ heterocyclic group, more preferably a $C_2$-$C_{16}$ heterocyclic group, for example, dibenzothiophene, benzonaphthothiophene, dibenzofuran, isoquinoline or the like; when $Ar^2$ is a fluorenyl group, $Ar^2$ may be 9,9-dimethyl-9H-fluorene.

When $Ar^3$ and $Ar^4$ are each an aryl group, $Ar^3$ and $Ar^4$ may be preferably a $C_6$-$C_{30}$ aryl group, more preferably a $C_6$-$C_{18}$ aryl group, for example, phenyl, naphthyl, biphenyl, terphenyl, phenanthryl or the like; when $Ar^3$ and $Ar^4$ are each a heterocyclic group, $Ar^3$ and $Ar^4$ may be preferably a $C_2$-$C_{30}$ heterocyclic group, more preferably a $C_2$-$C_{16}$ heterocyclic group, for example, pyridine, dibenzothiophene, benzonaphthothiophene, dibenzofuran, phenanthroline, isoquinoline or the like, but carbazole is excluded from the heterocyclic group; when $Ar^3$ and $Ar^4$ are each a fluorenyl group, $Ar^3$ and $Ar^4$ may be, for example, 9,9-dimethyl-9H-fluorene, 9,9-diphenyl-9H-fluorene, 9,9'-spirofluorene or the like.

$R^1$ to $R^3$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

m and o are each an integer of 0 to 4, n is an integer of 0 to 3, and plural $R^1$s to plural $R^3$s are each the same or different from each other where m, n or o is each an integer of 2 or more. When $R^1$ to $R^3$ are each an aryl group, $R^1$ to $R^3$ may be preferably a $C_6$-$C_{30}$ aryl group, more preferably a $C_6$-$C_{10}$ aryl group, for example, phenyl, naphthyl or the like.

Further, adjacent $R^1$ groups, adjacent $R^2$ groups and/or adjacent $R^3$ groups may optionally be linked together to each other to form a ring, where m, n or o is each an integer of 2 or more. Here, the ring may be a monocyclic or polycyclic ring, and the ring may be a $C_6$-$C_{30}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring or the like. When adjacent $R^1$ groups, adjacent $R^2$ groups and/or adjacent $R^3$ groups are linked together to each other to form an aryl group, the ring may be, for example, a benzene ring, as a result, naphthalene, phenanthrene or the like may be formed together with the benzene ring to which they are bonded.

$L^1$ is selected from the group consisting of a $C_6$-$C_{60}$ arylene group, a fluorenylene group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, and an aliphatic hydrocarbon group.

When $L^1$ is an arylene group, $L^1$ may be preferably a $C_6$-$C_{30}$ arylene group, more preferably a $C_6$-$C_1$ arylene group, for example, phenylene, biphenyl, terphenyl, naphthalene, anthrancene, phenanthrene or the like; when $L^1$ is a heterocyclic group, $L^1$ may be preferably a $C_2$-$C_{30}$ heterocyclic group, more preferably a $C_2$-$C_{18}$ heterocyclic group, for example, dibenzofuran, dibenzothiophene, benzonaphthothiophene or the like; when $L^1$ is a fluorenyl group, $L^1$ may be, for example, 9,9-dimethyl-9H-fluorene.

The aryl group, arylene group, fluorenyl group, fluorenylene group, heterocyclic group, fused ring group, alkyl group, alkenyl group, alkynyl group, alkoxyl group and aryloxyl group of $Ar^1$ to $Ar^4$, $R^1$ to $R^3$, $R^6$, $R^7$ and $L^1$ are each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group, wherein adjacent substituents may optionally be linked together to form a ring where the substituents are adjacent, with the proviso that where $Ar^2$ to $Ar^4$ is the aryl group, the aryl group can be substituted with the heterocyclic group wherein the heterocyclic group excludes a carbazole group, a dibenzothienyl group and a dibenzofuryl group.

Preferably, the Formula 1 is represented by one of the following Formulas 2 to 4:

<Formula 2>

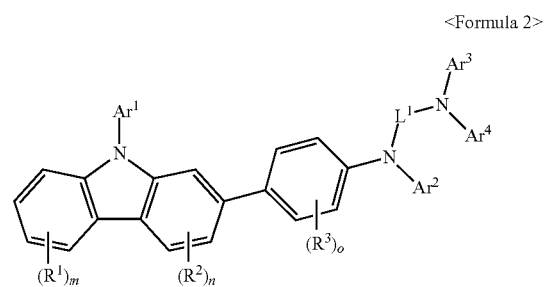

<Formula 3>

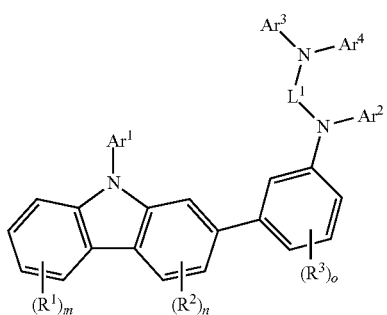

<Formula 4>

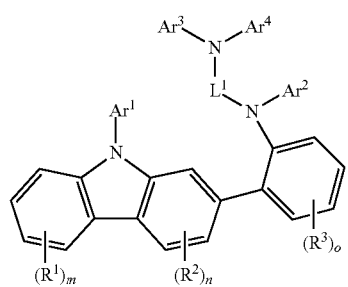

wherein each of symbols is the same as defined in the Formula 1. That is, $Ar^1$ to $Ar^4$, $R^1$ to $R^3$, $L^1$, m, n and o are the same as defined in the Formula 1.

Preferably, $L^1$ is represented by one of the following Formulas L1-1 to L1-7 in Formulas 1 to 4:

<Formula L1-1>

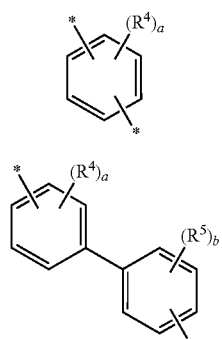

<Formula L1-2>

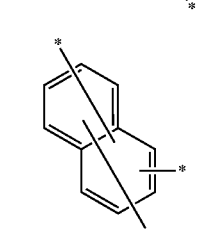

<Formula L1-3>

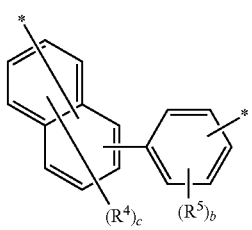

<Formula L1-4>

<Formula L1-5>

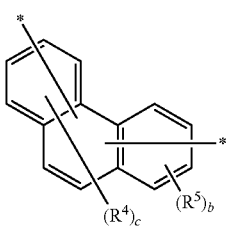

<Formula L1-6>

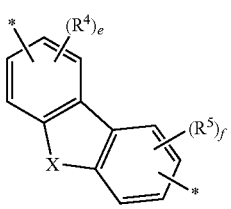

<Formula L1-7>

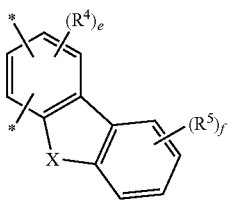

In the formulas L1-1 to L1-7, each of symbols may be defined as follows, and "*" indicates the bonding position.

X is S, O, $C(R^a)(R^b)$ or $N(R^c)$. Here, $R^a$, $R^b$ and $R^c$ are each independently selected from the group consisting of a $C_6$-$C_{20}$ aryl group, a fluorenyl group, a $C_2$-$C_{20}$ heterocyclic group containing at least one heteroatom selected from the group consisting of O, N, S, Si, and P, a fused ring group of a $C_3$-$C_{20}$ aliphatic ring and a $C_6$-$C_{60}$ aromatic ring, a $C_1$-$C_{20}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, and $R^a$ and $R^b$ may optionally be linked together to form a spiro compound together with a carbon to which they are bonded. Where $R^a$ and $R^b$ are each alkyl group, $R^a$ and $R^b$ may be preferably a $C_1$-$C_{10}$ alkyl group, for example, methyl group.

$R^4$ and $R^5$ are each independently selected from the group consisting of a $C_6$-$C_{20}$ aryl group, a fluorenyl group, a $C_2$-$C_{20}$ heterocyclic group containing at least one heteroatom selected from the group consisting of O, N, S, Si, and P, a fused ring group of a $C_3$-$C_{20}$ aliphatic ring and a $C_6$-$C_{60}$ aromatic ring, a $C_1$-$C_{20}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group. a and b are each an integer of 0 to 4, c is an integer of 0 to 6, d is an integer of 0 to 5, e and f are each an integer of 0 to 3, and each of the plurality of $R^4$s and each of the plurality of $R^5$s are the same or different from each other where a, b, c, d, e and f are each an integer of 2 or more.

Preferably, the Formula L1-1 is one of the following structures.

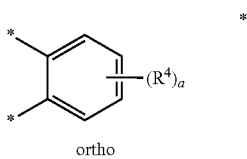

ortho

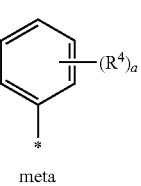

meta

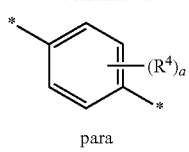
para
Specifically, the compound represented by formula 1 may be any one of the following compounds.
P-1
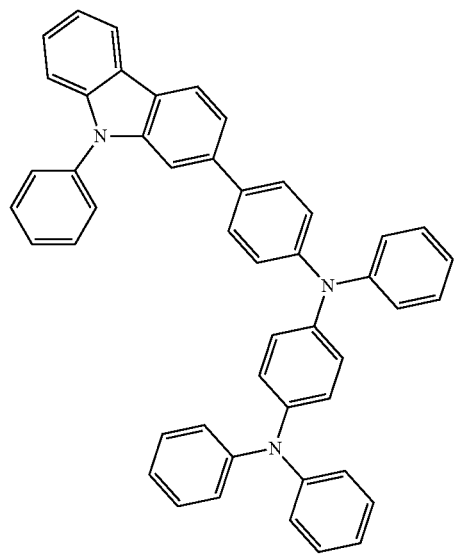
P-2
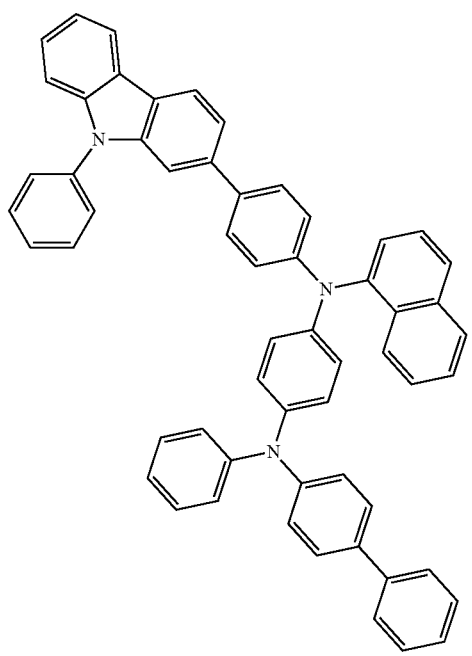
P-3
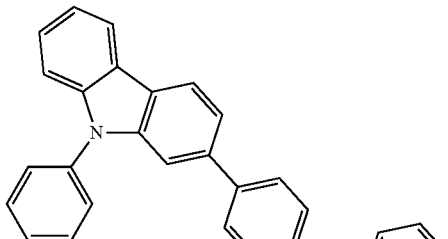
P-4
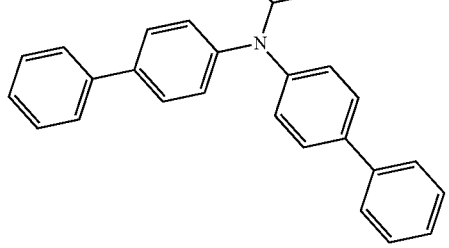

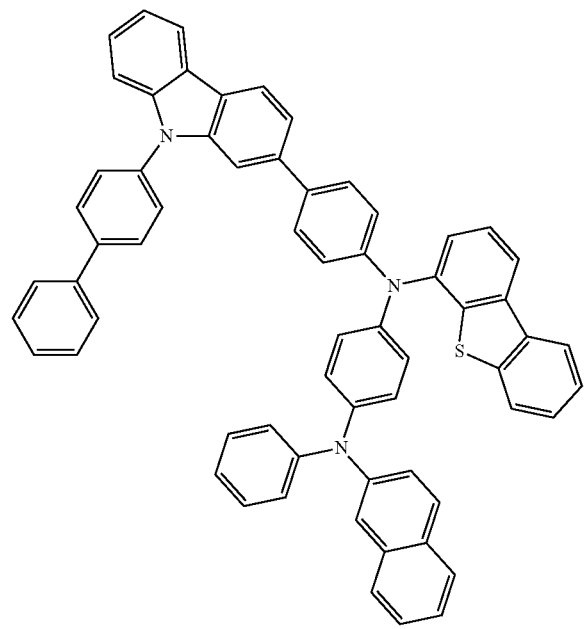
P-5
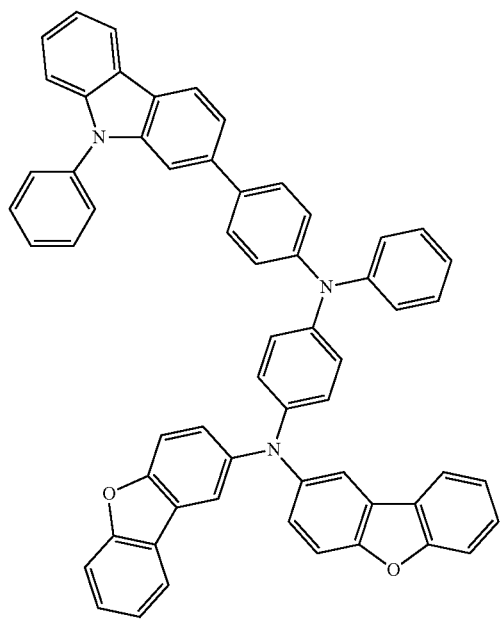
P-7
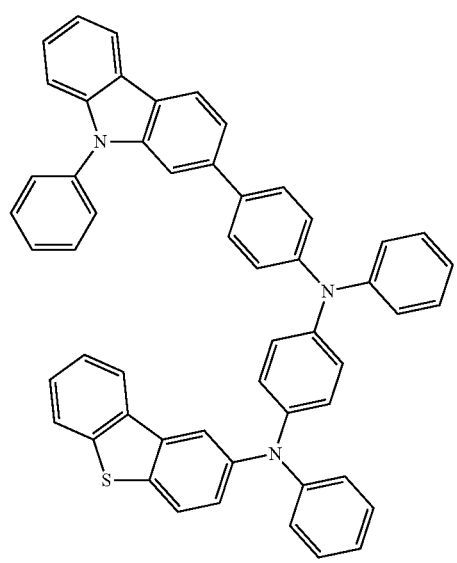
P-6
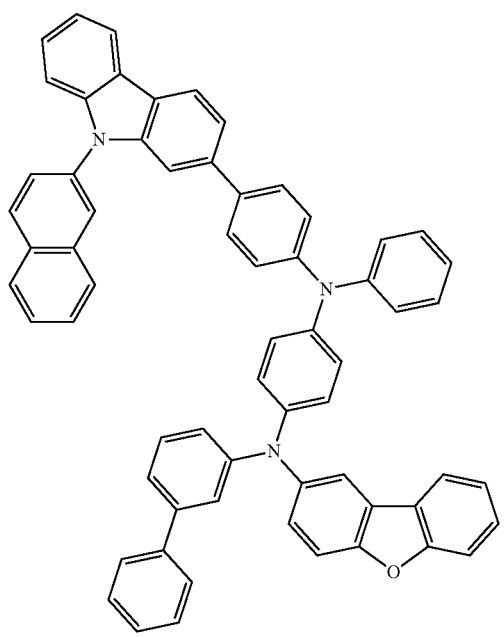
P-8

-continued
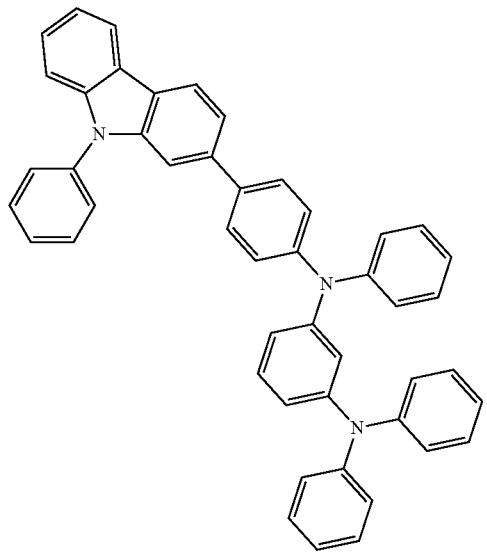
P-9
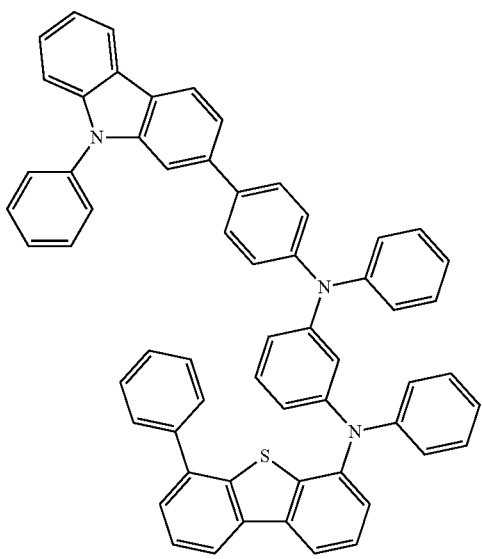
P-11
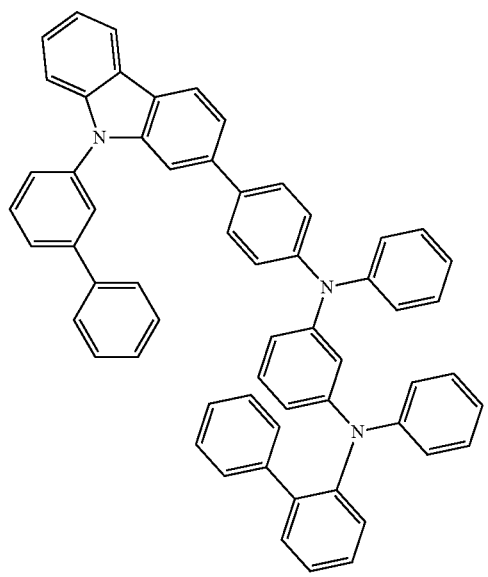
P-10
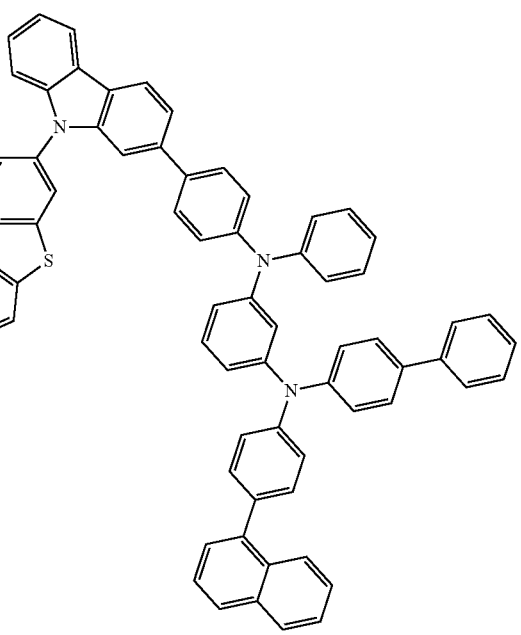
P-12

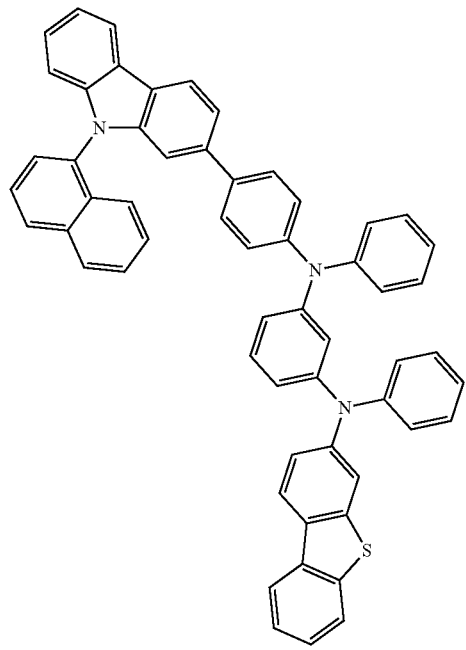
P-13
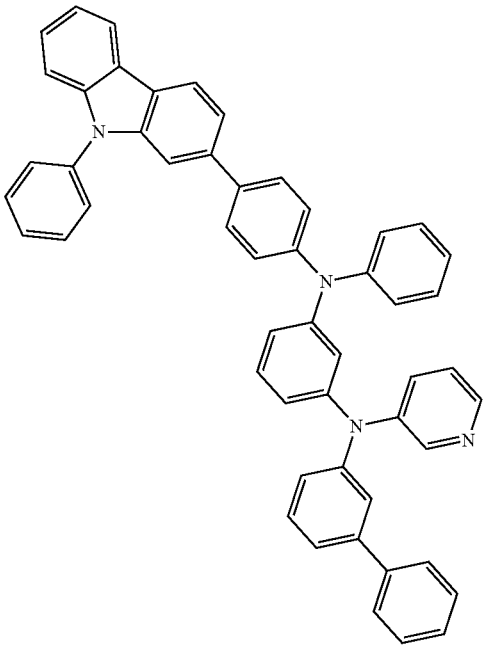
P-15
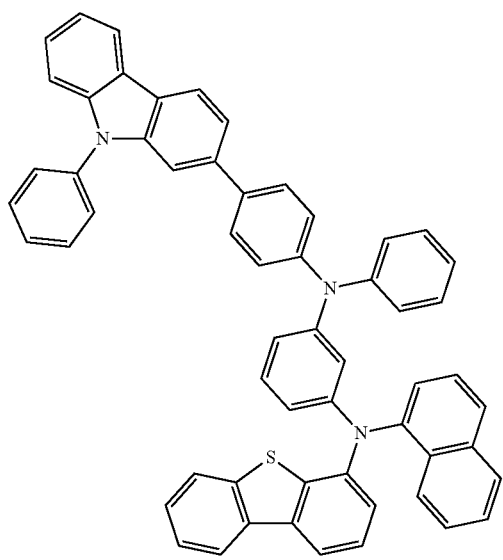
P-14
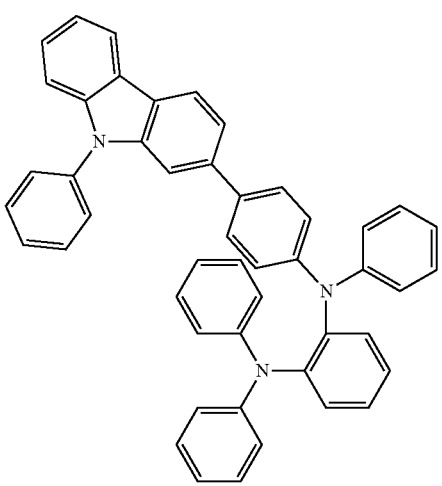
P-16

P-17
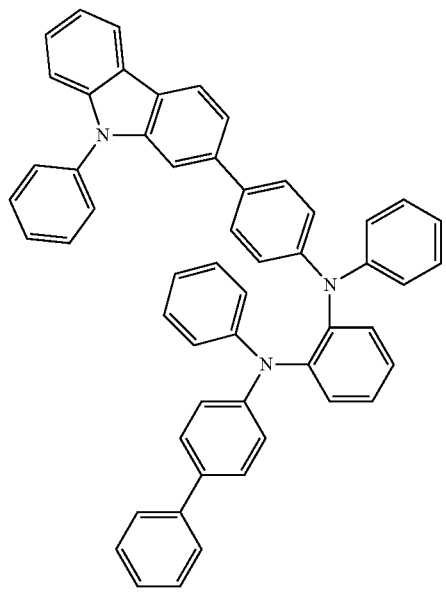
P-18
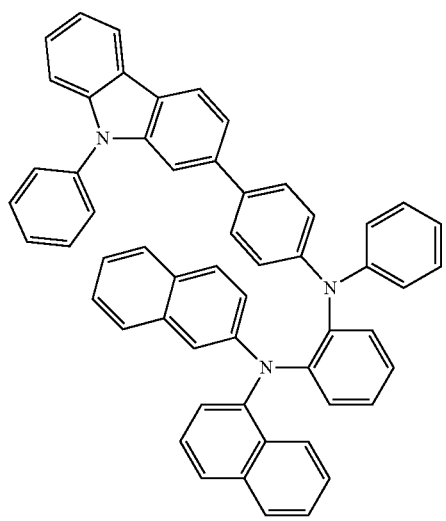
P-19
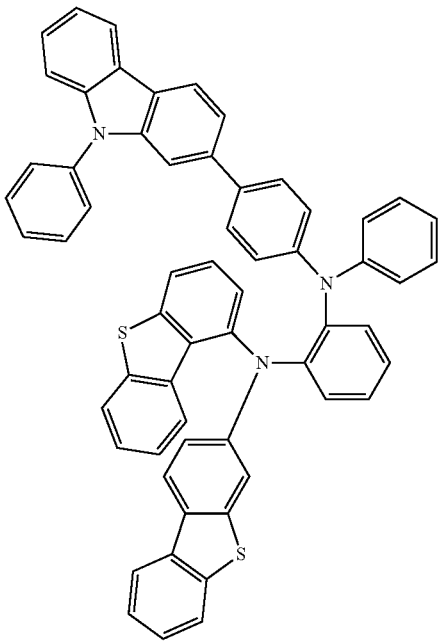
P-20
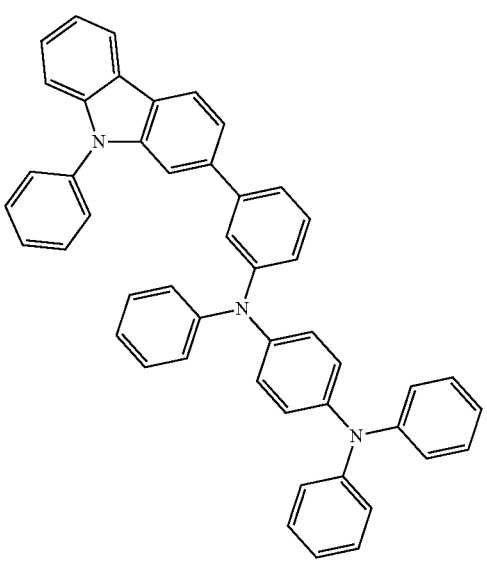

P-21
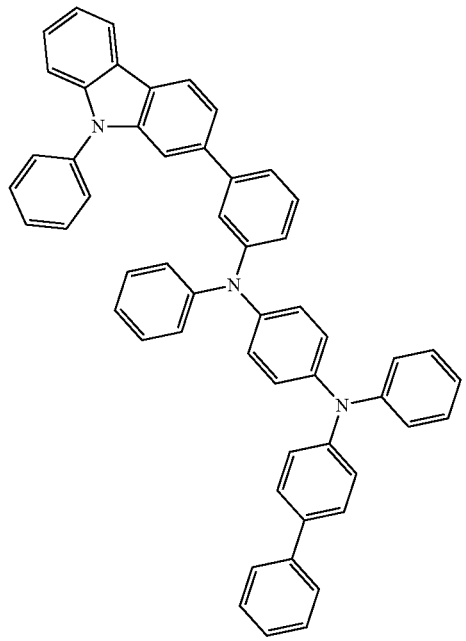
P-23
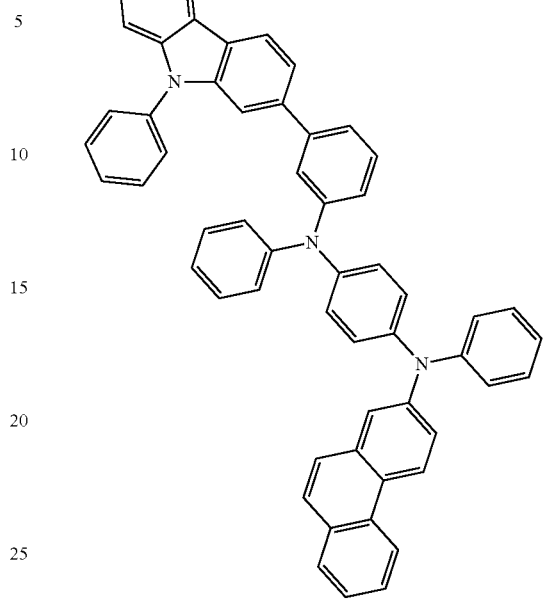
P-22
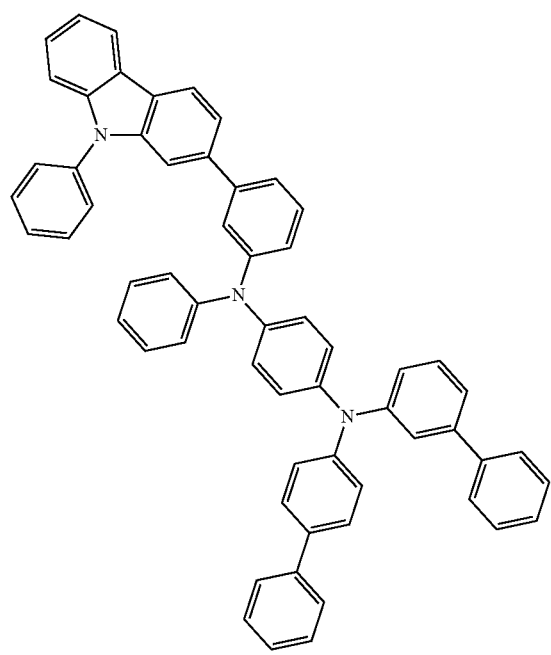
P-24
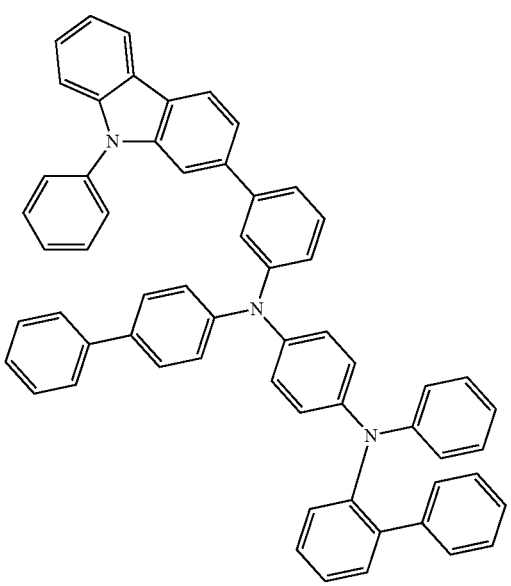

P-25
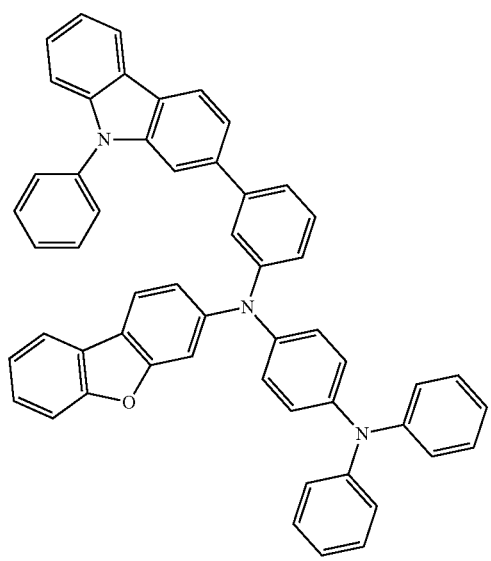
P-26
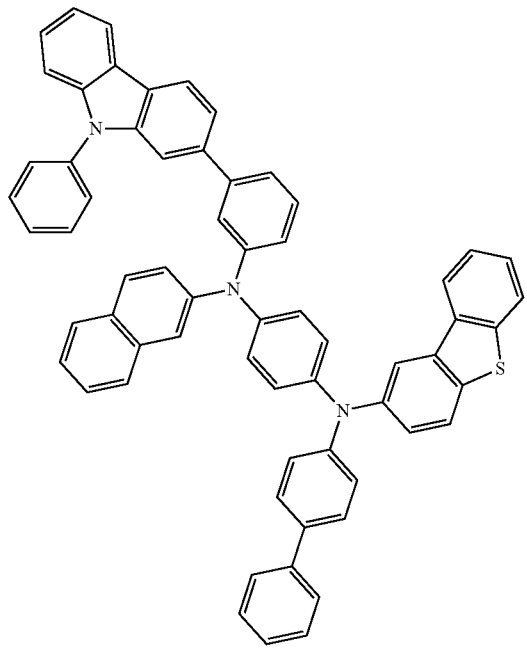
P-27
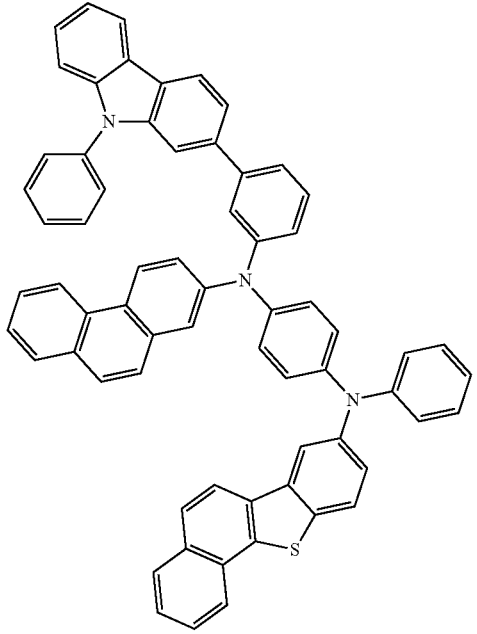
P-28
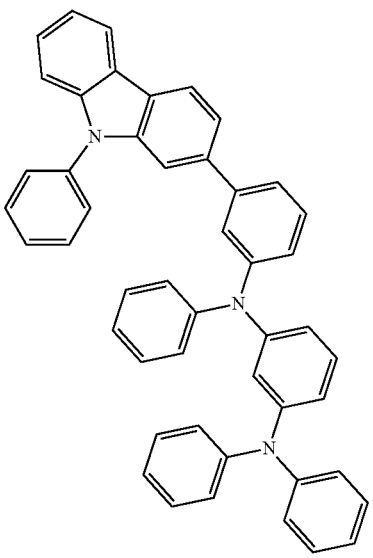

P-29
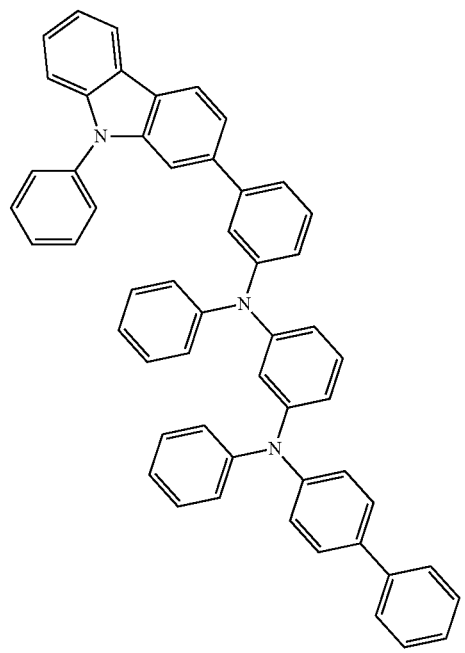
P-30
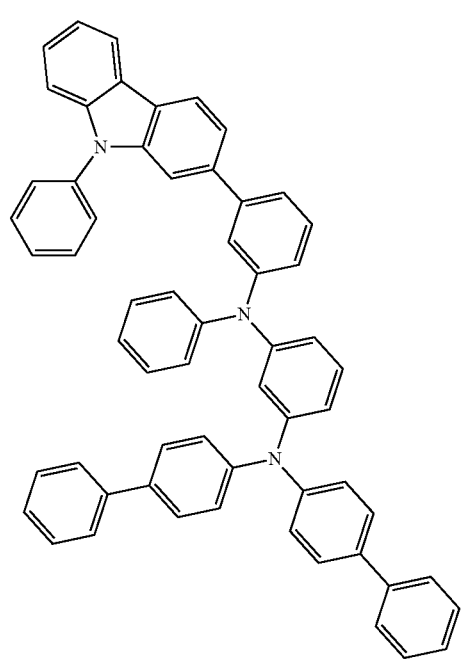
P-31
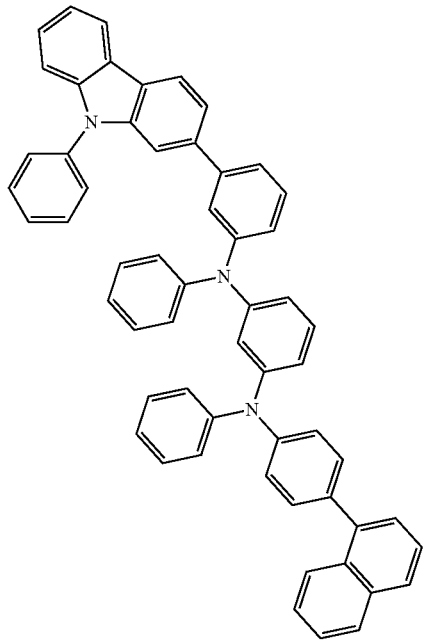
P-32
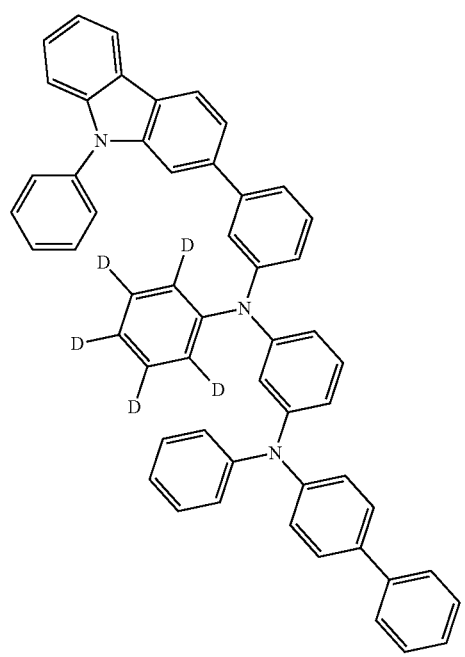

P-33
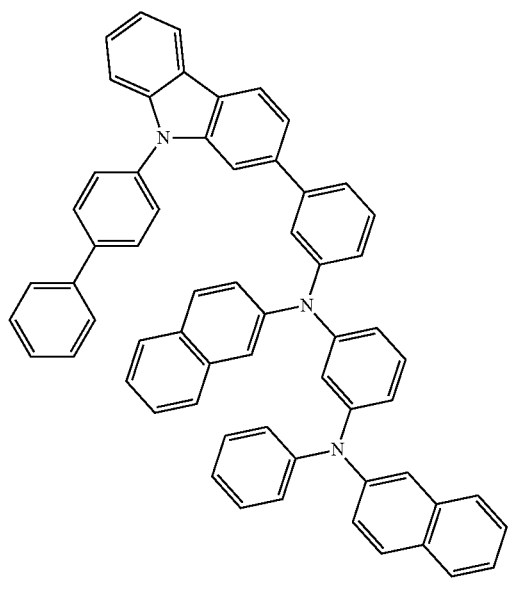
P-34
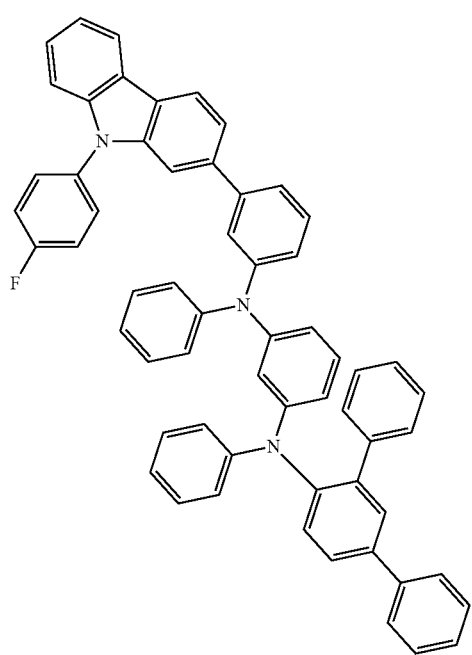
P-35
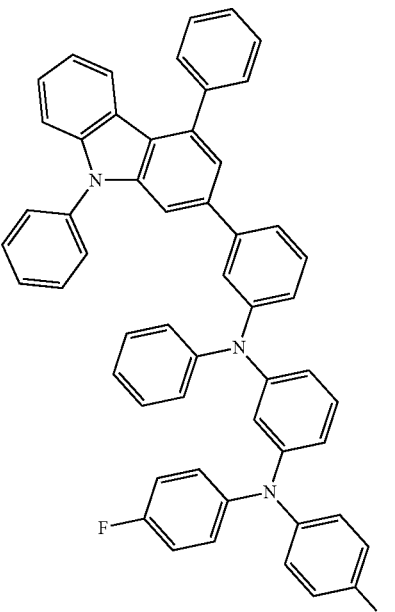
P-36
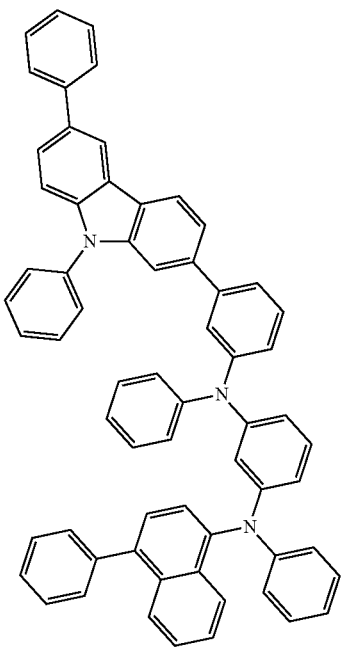

P-37
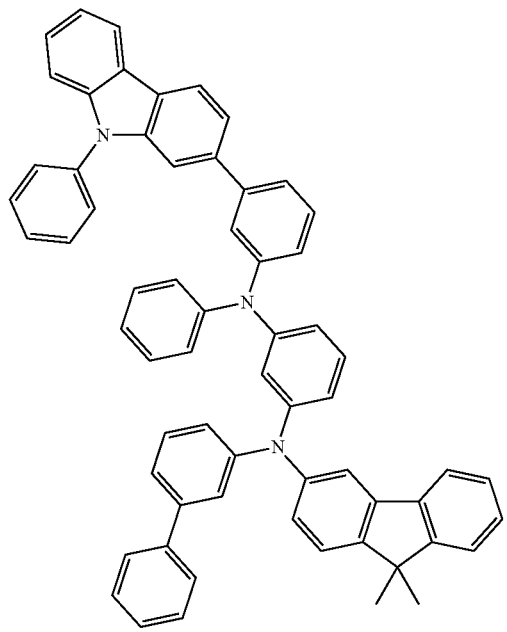
P-38
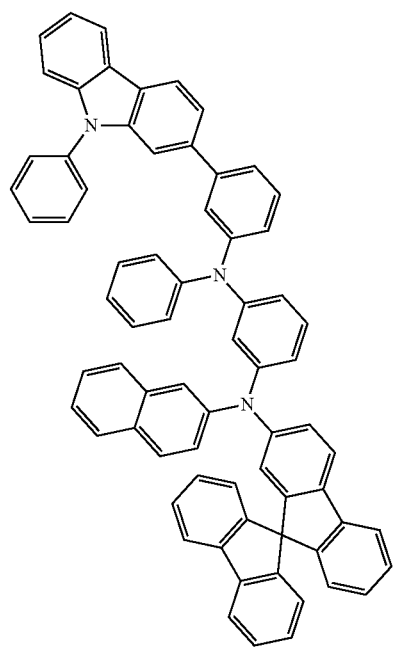
P-39
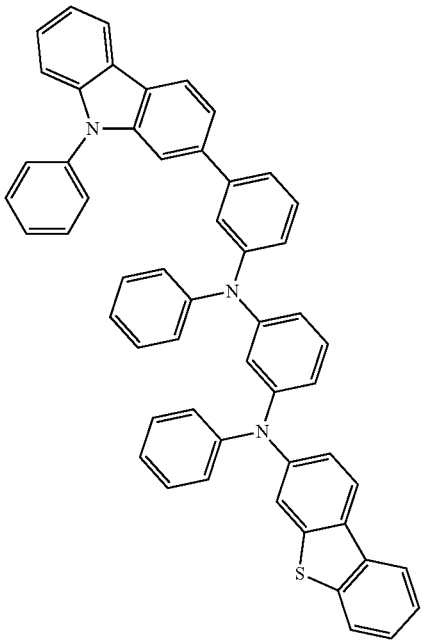
P-40
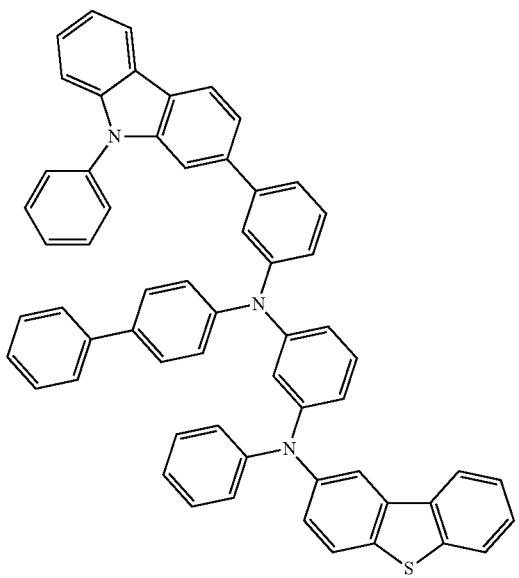

P-41
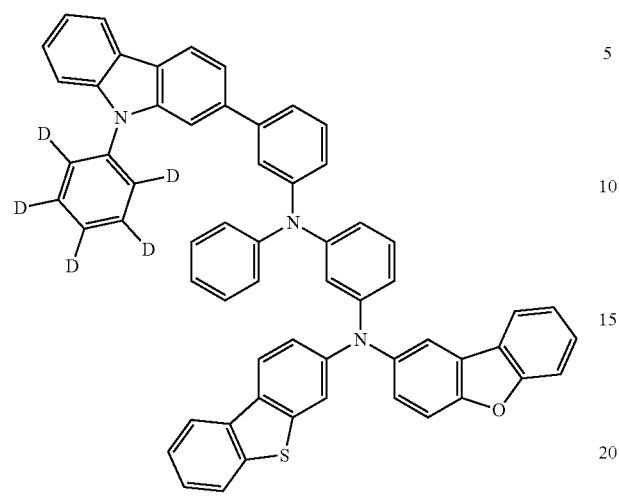
P-43
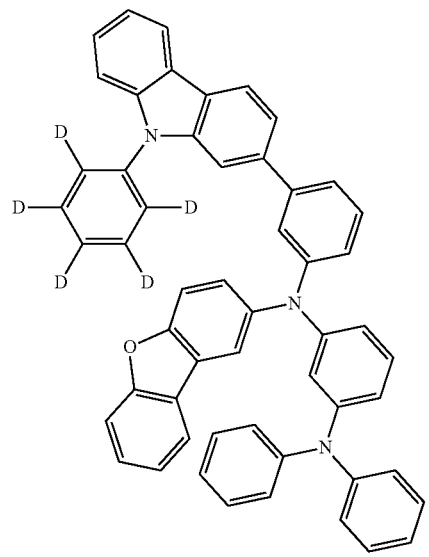
P-42
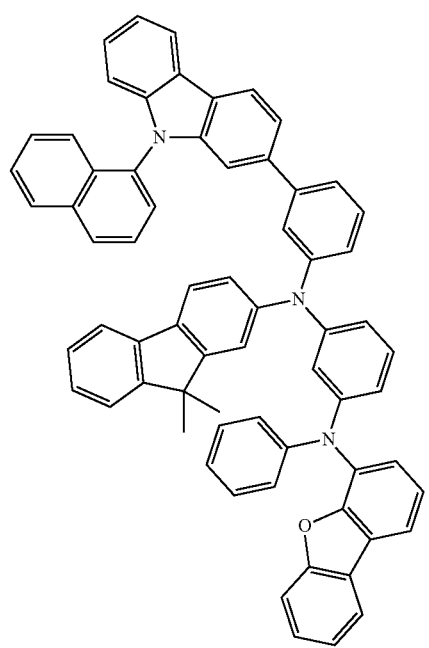
P-44
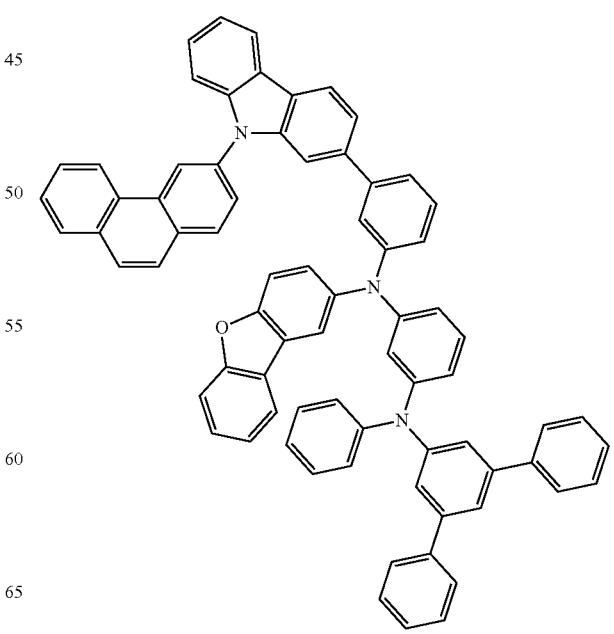

P-45
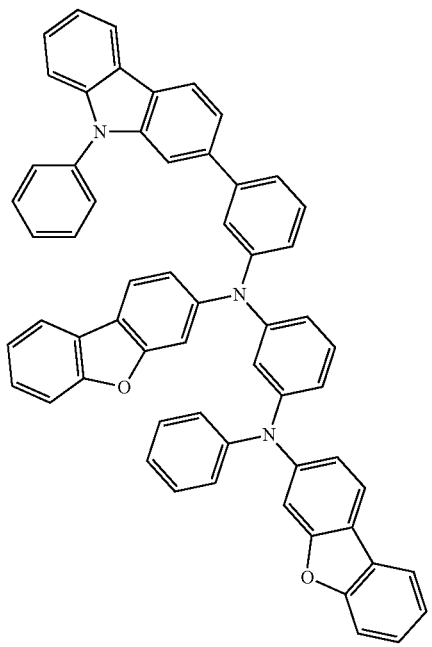
P-47
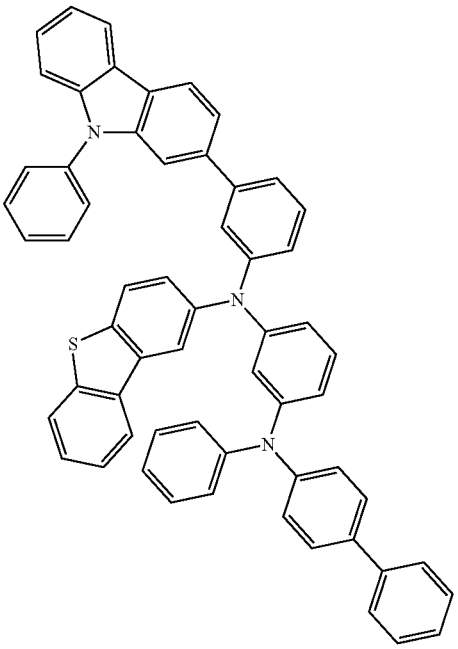
P-46
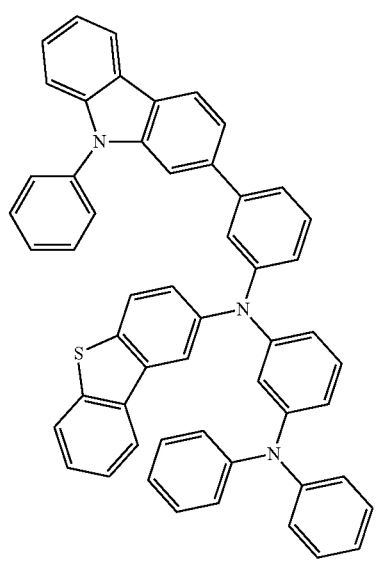
P-48
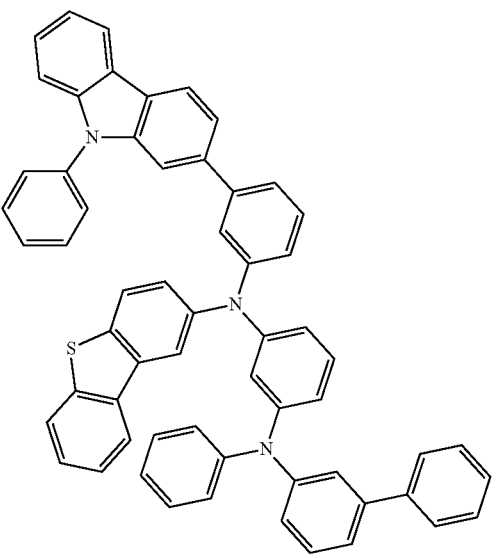

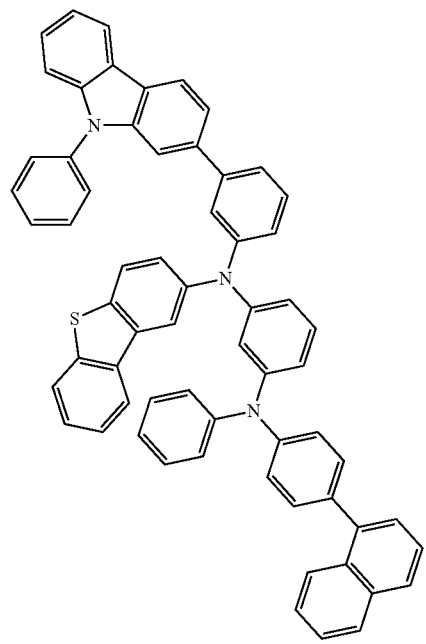
P-49
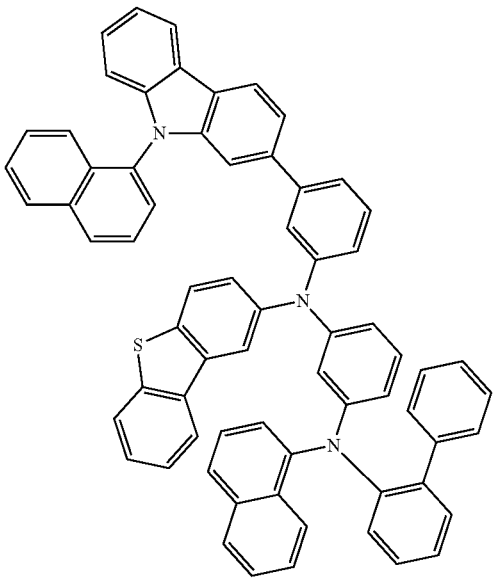
P-51
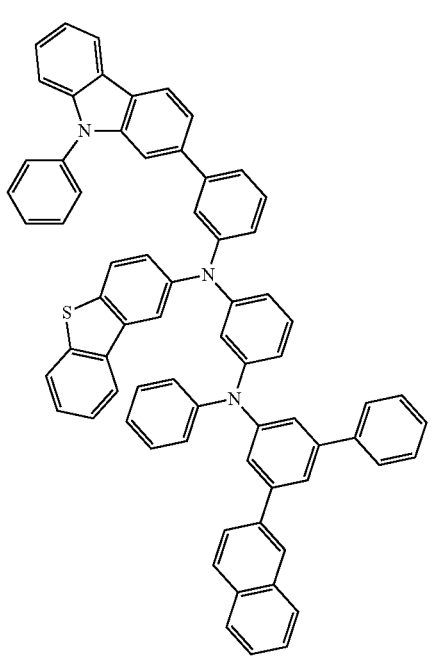
P-50
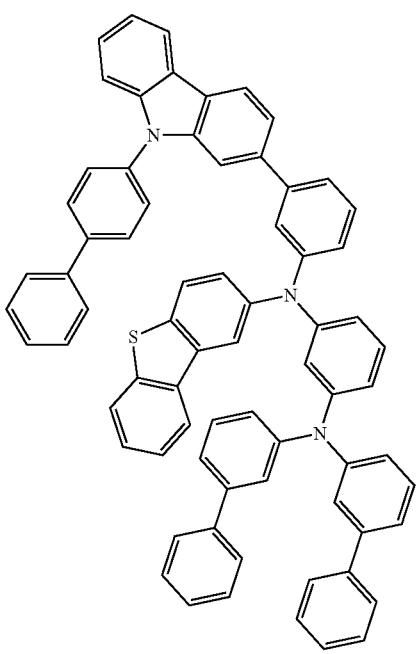
P-52

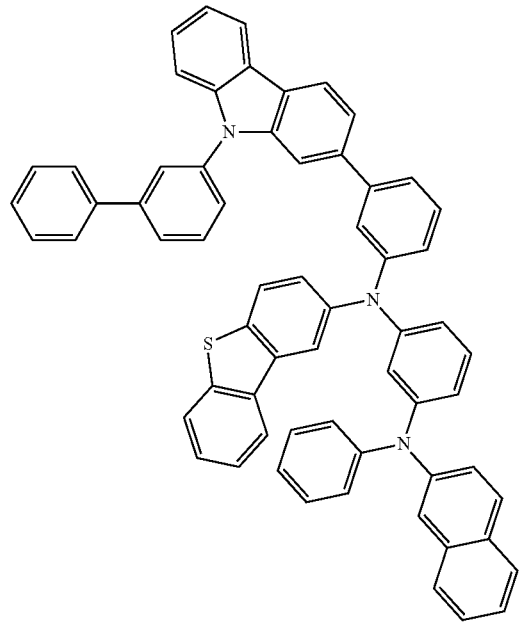
P-53
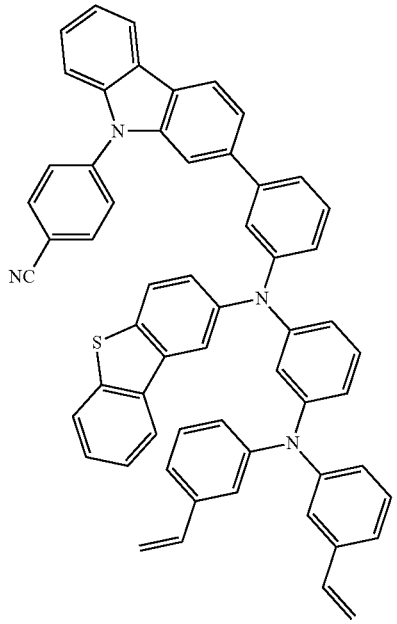
P-55
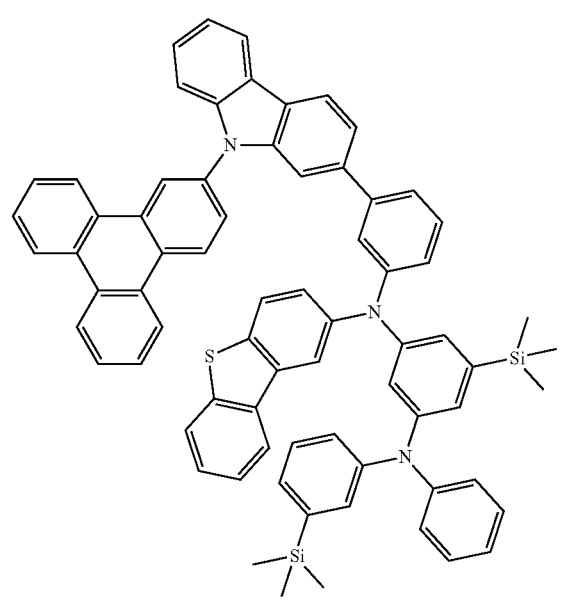
P-54
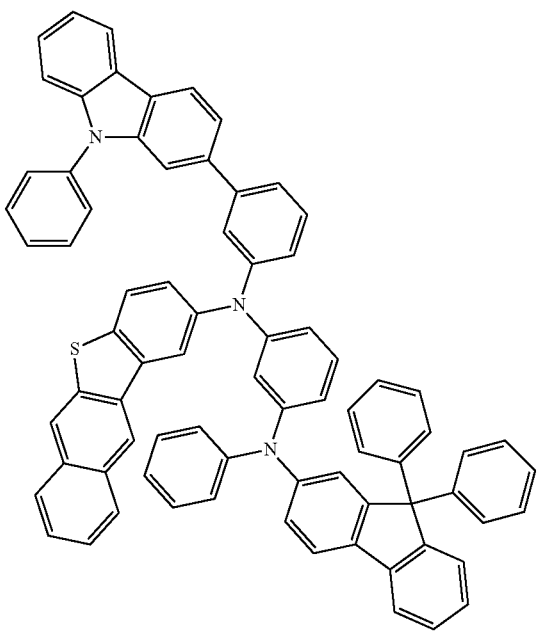
P-56

P-57
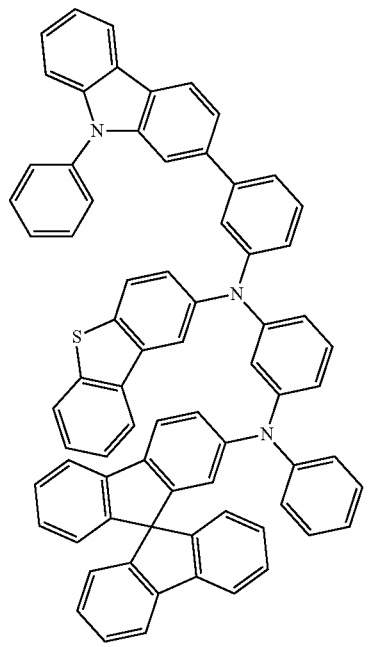
P-58
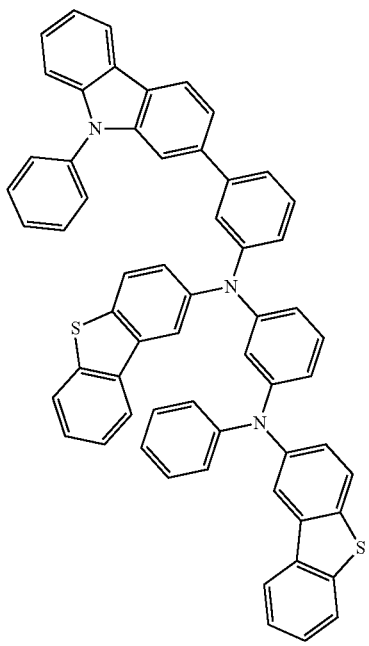
P-59
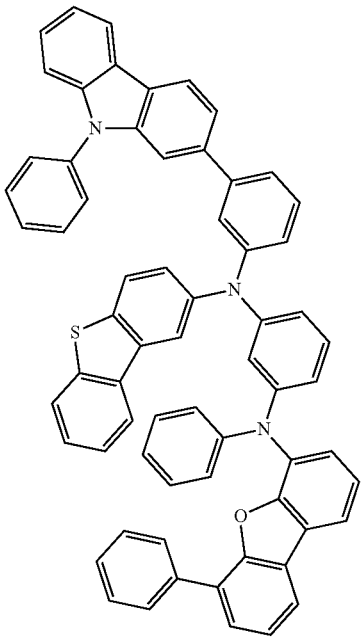
P-60
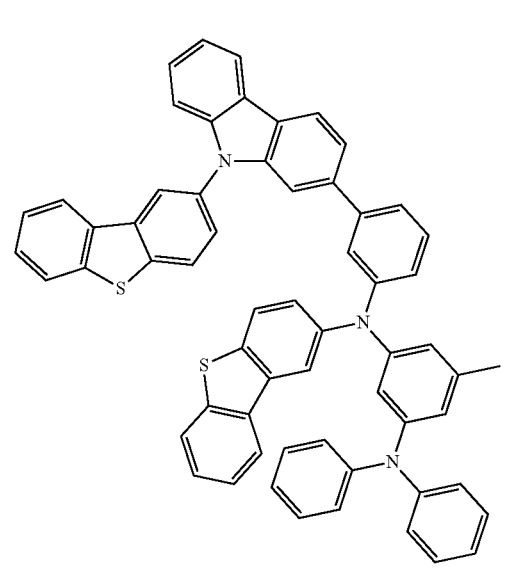

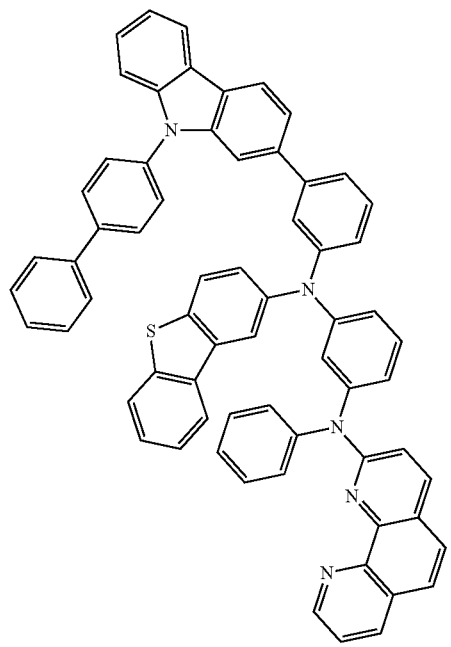
P-61
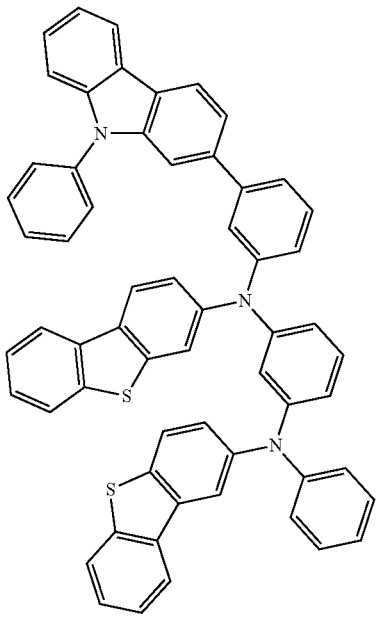
P-63
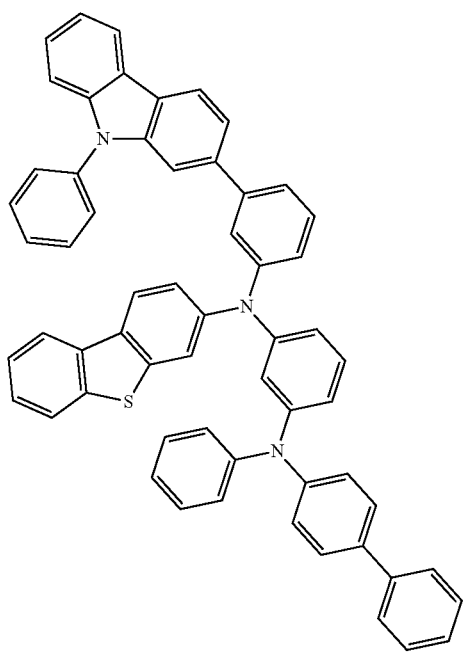
P-62
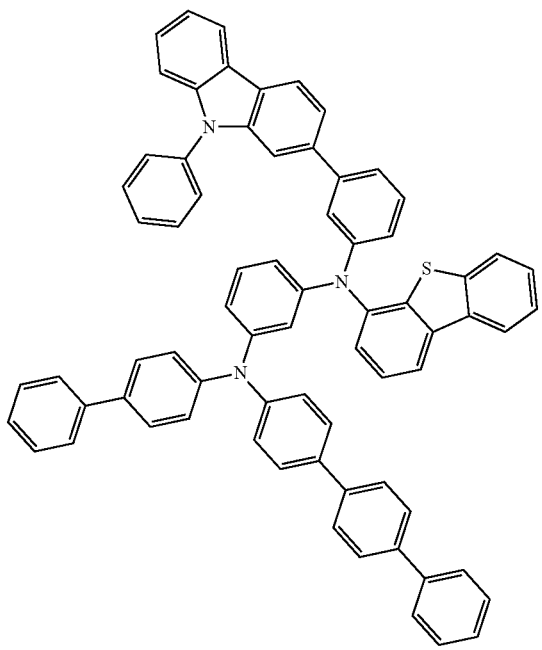
P-64

P-65
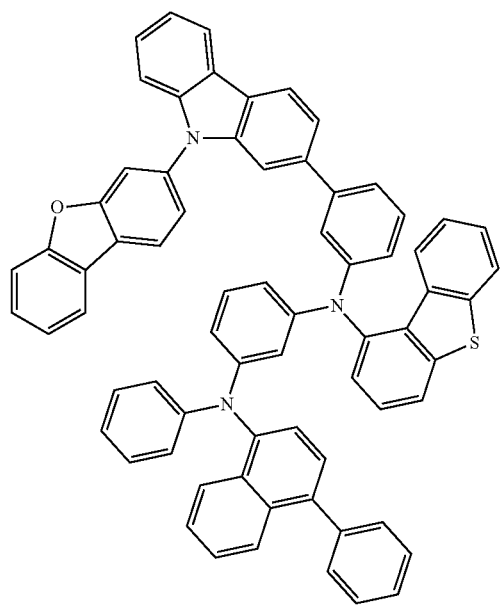
P-66
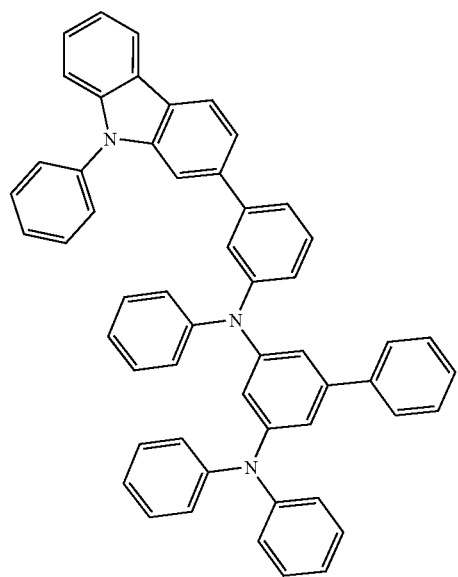
P-67
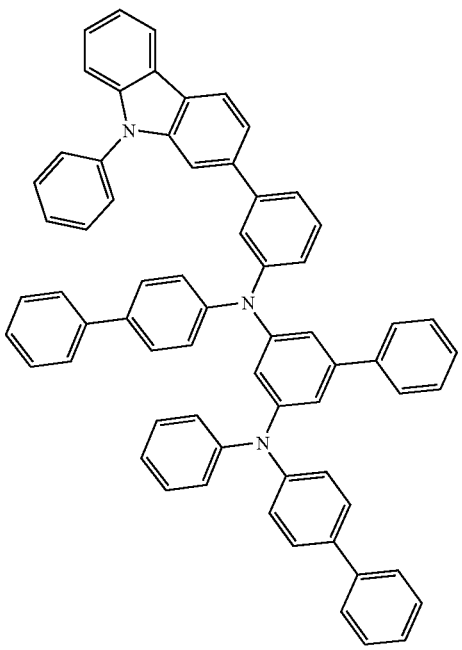
P-68
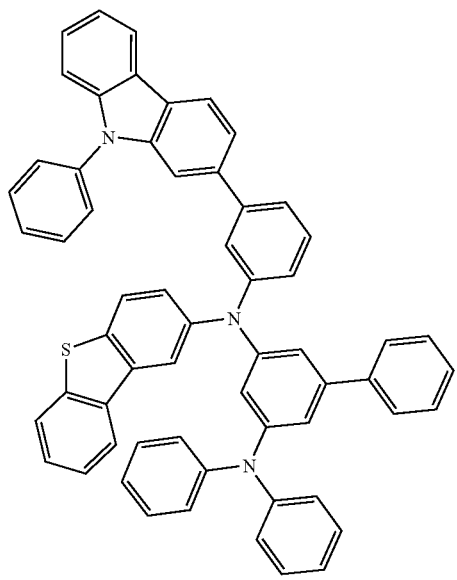

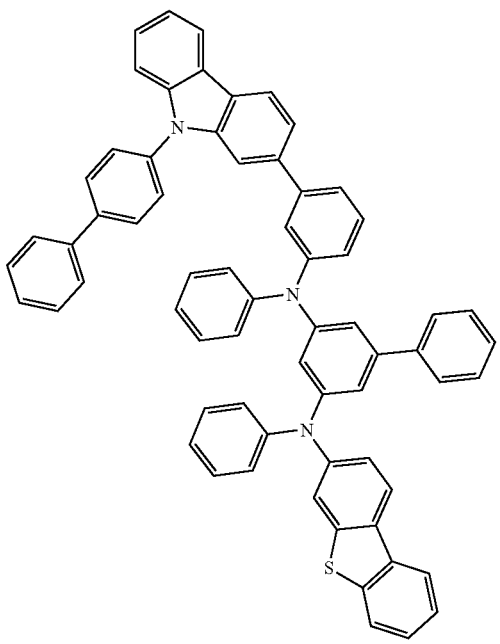
P-69
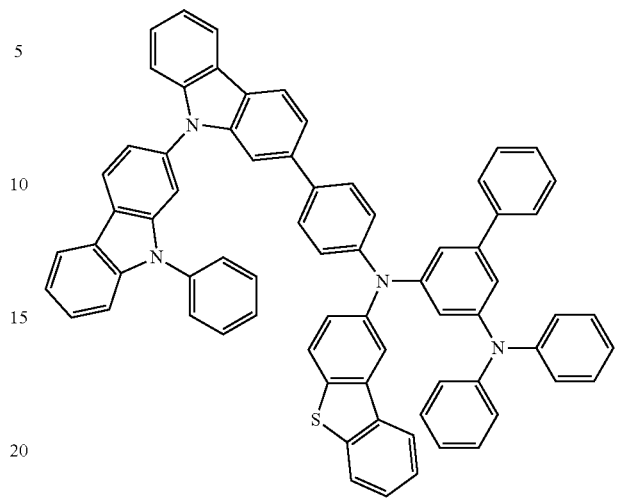
P-71
P-70
P-72
P-73
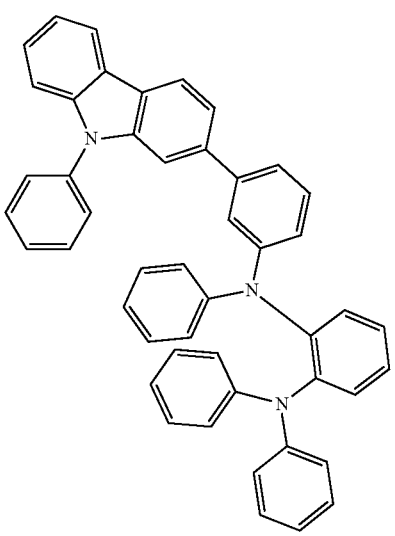

-continued
P-74
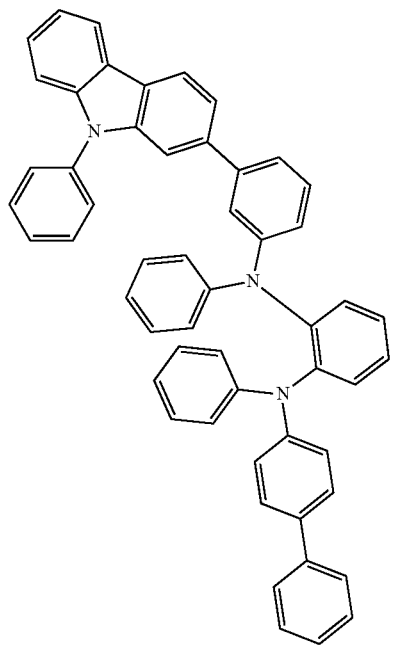
P-75
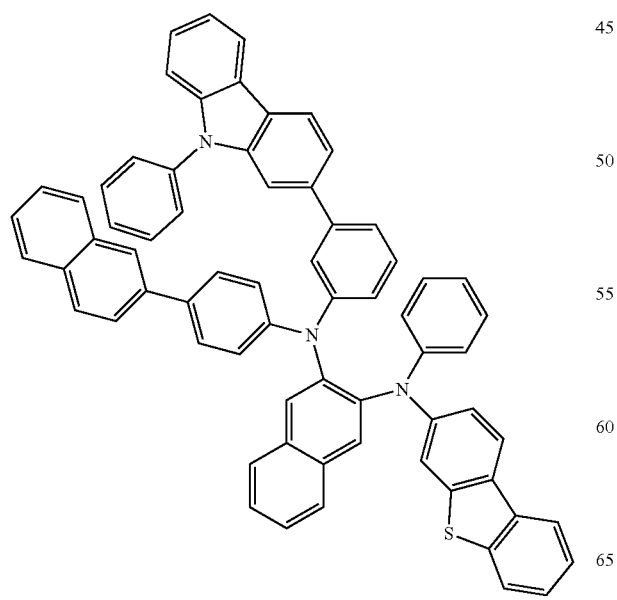
-continued
P-76
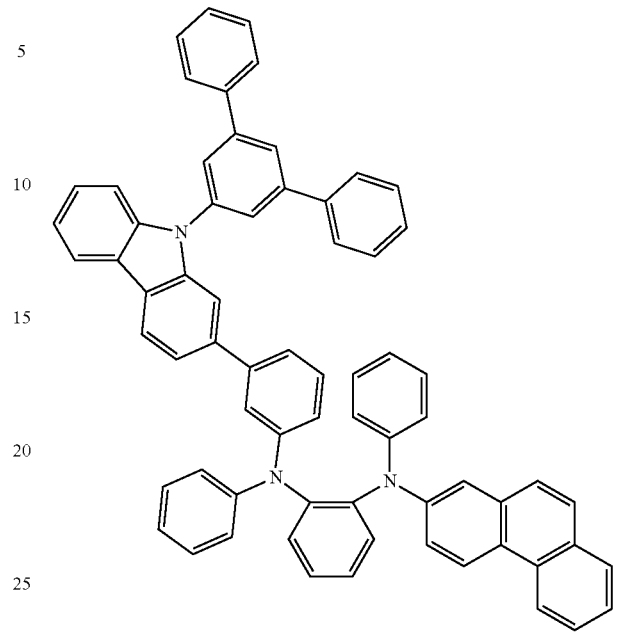
P-77
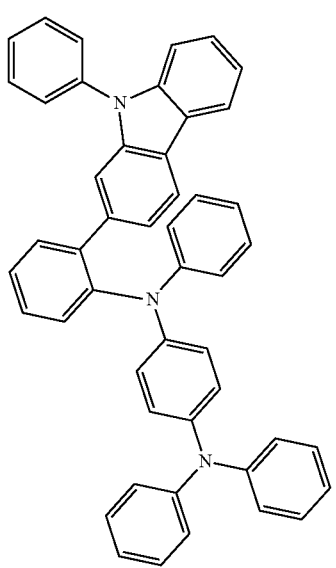

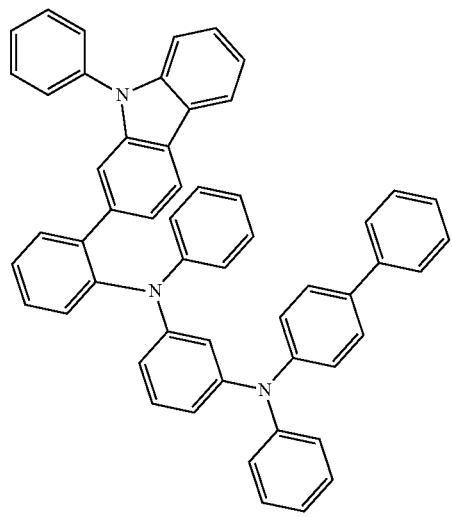
P-78
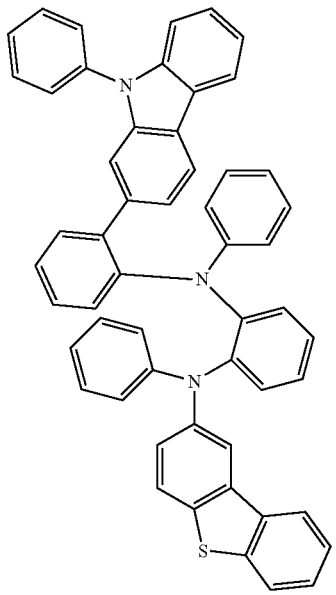
P-80
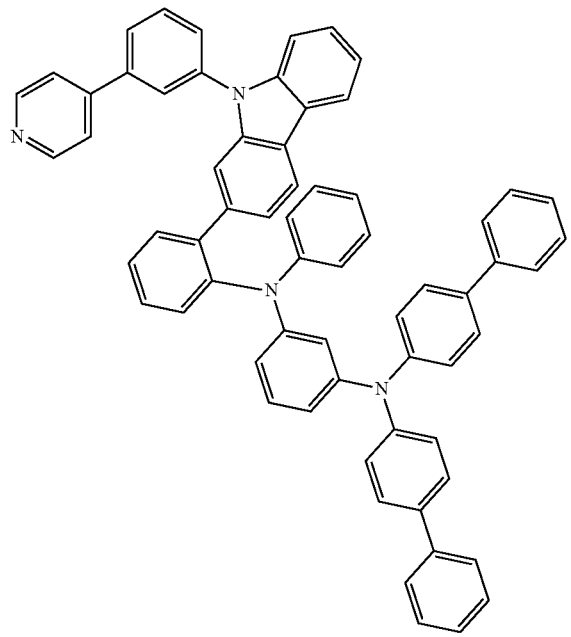
P-79
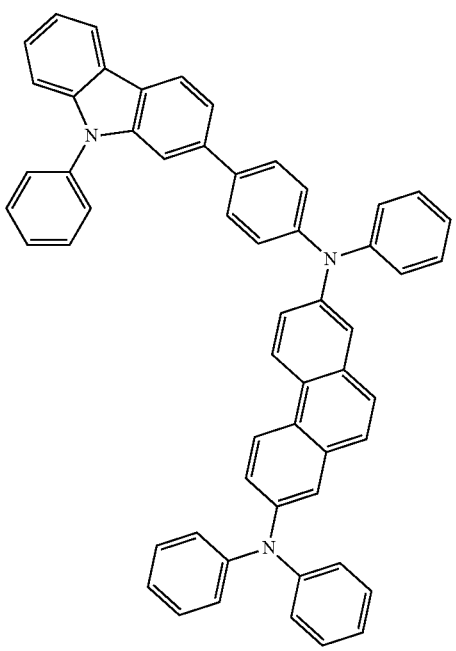
P-81

P-82
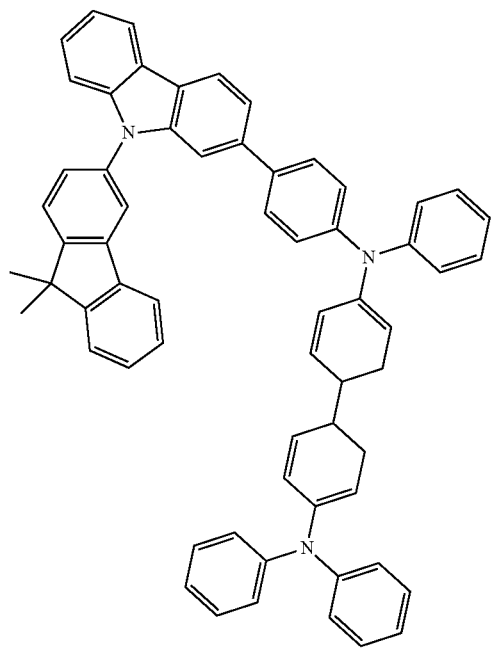
P-83
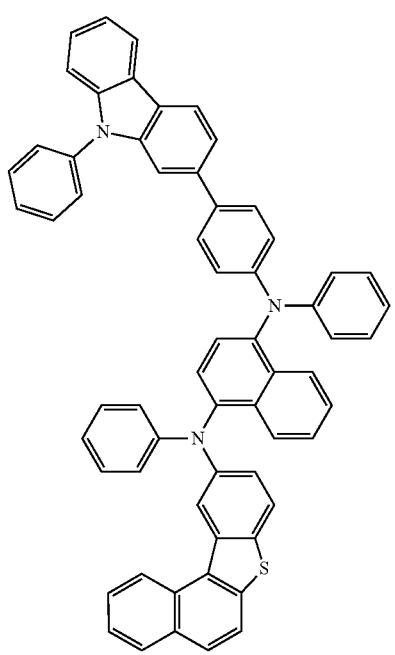
P-84
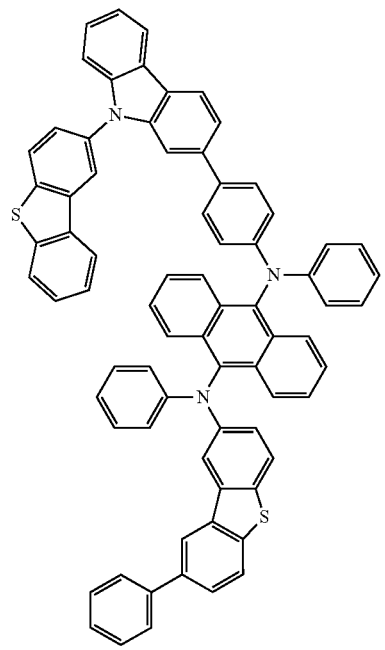
P-85
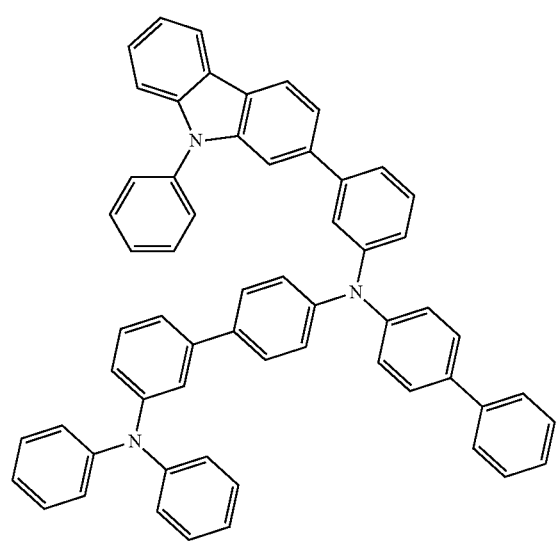

P-86
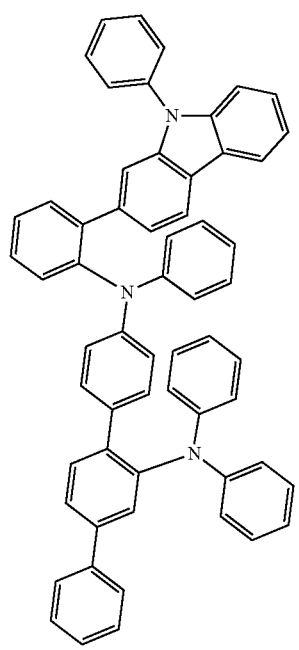
P-88
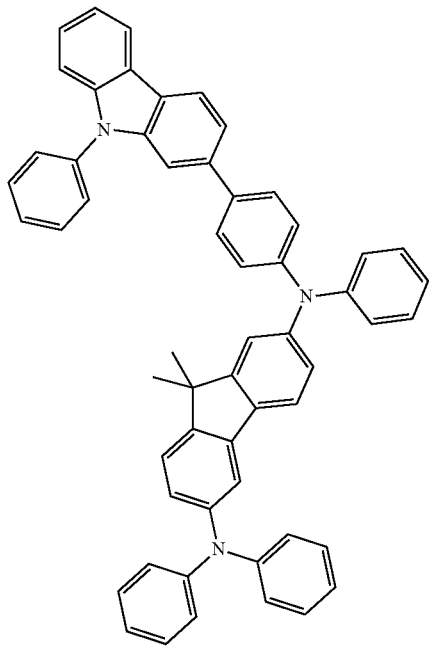
P-87
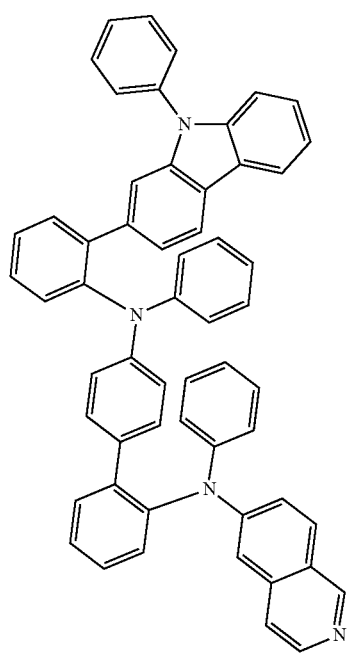
P-89
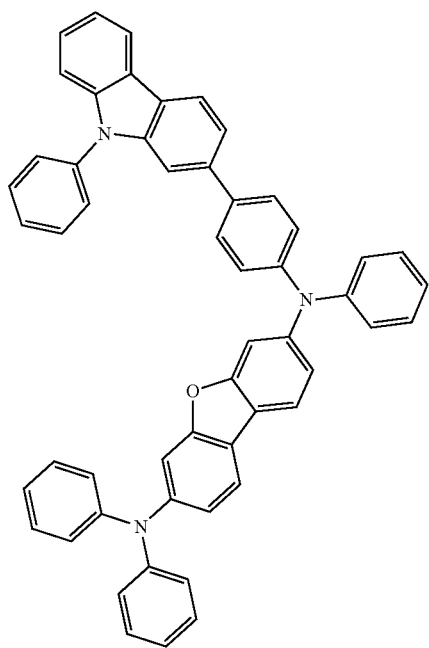

P-90
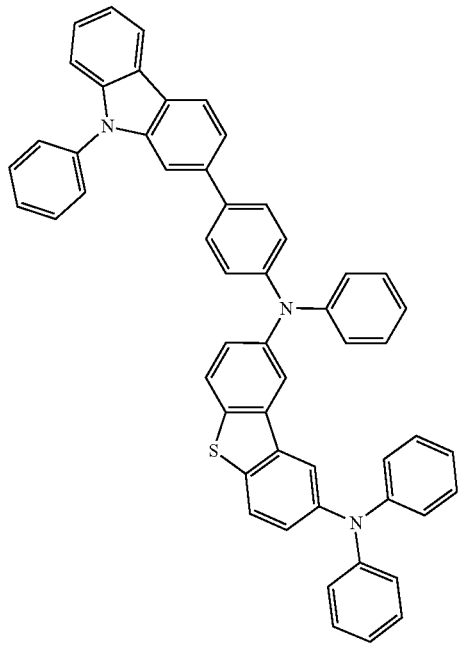
P-91
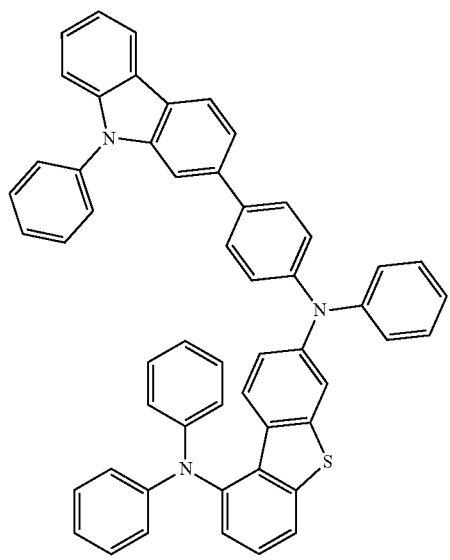
P-92
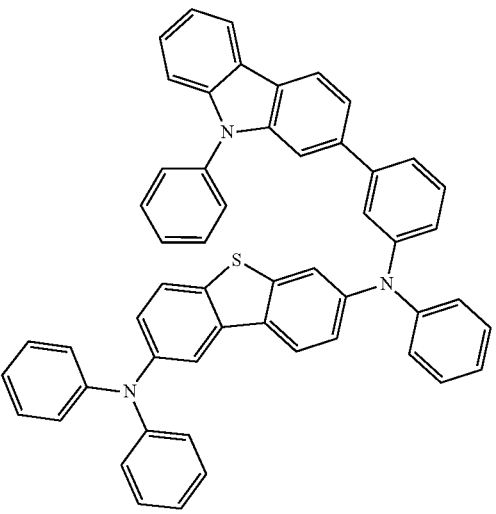
P-93
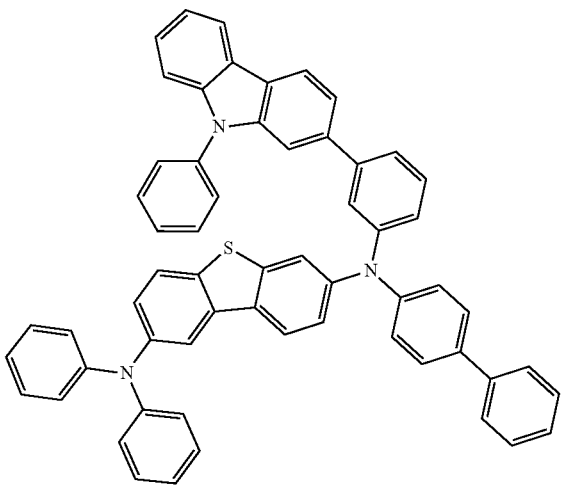
P-94
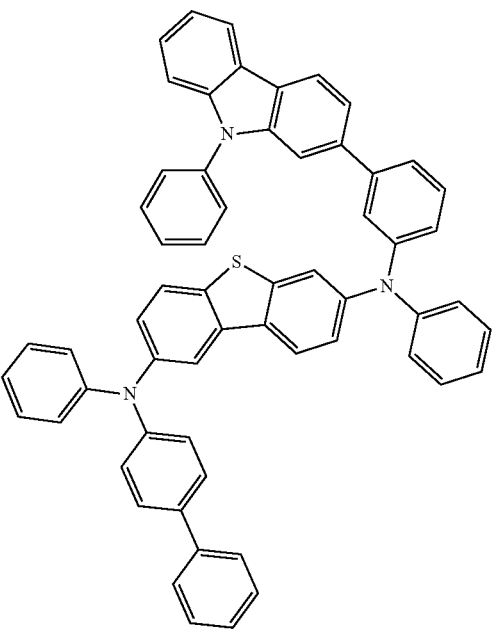

P-95
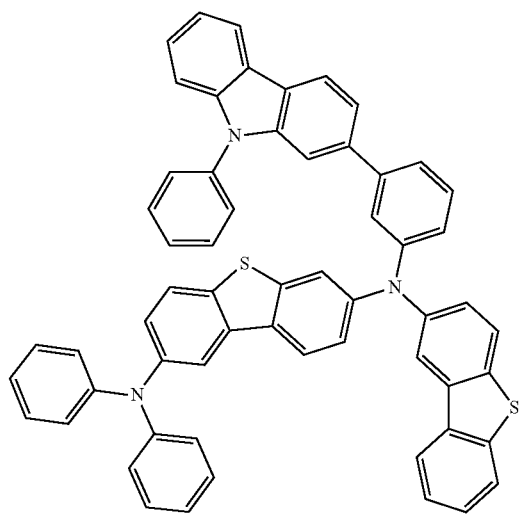
P-96
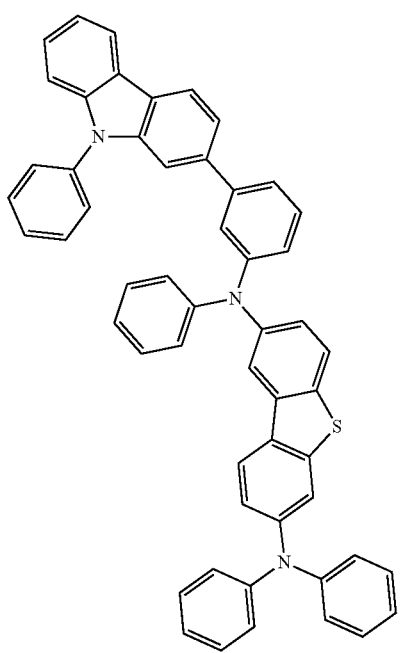
P-97
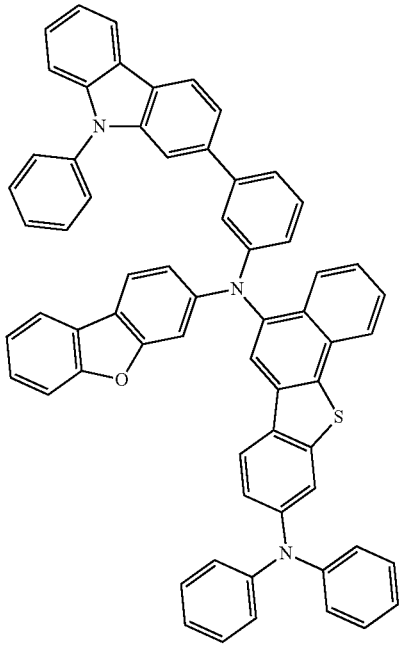
P-98
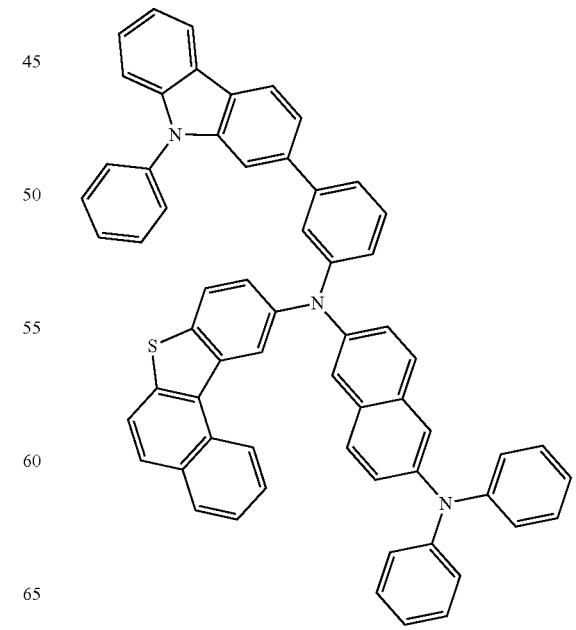

P-99
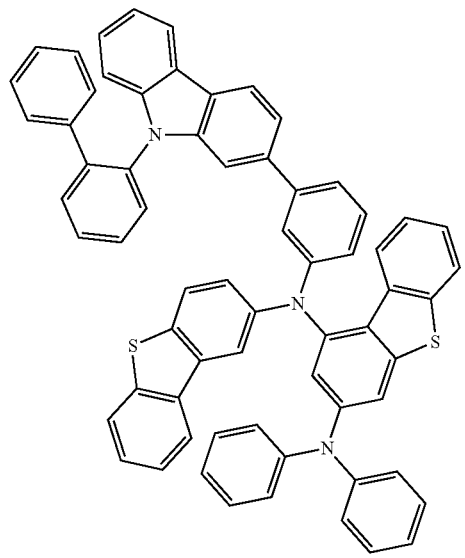
P-100
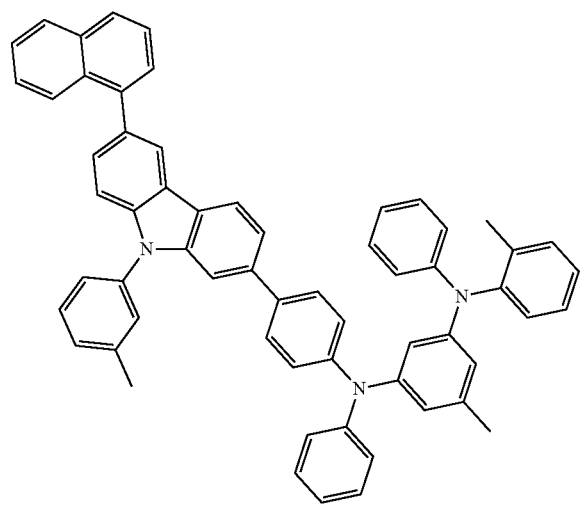
P-101
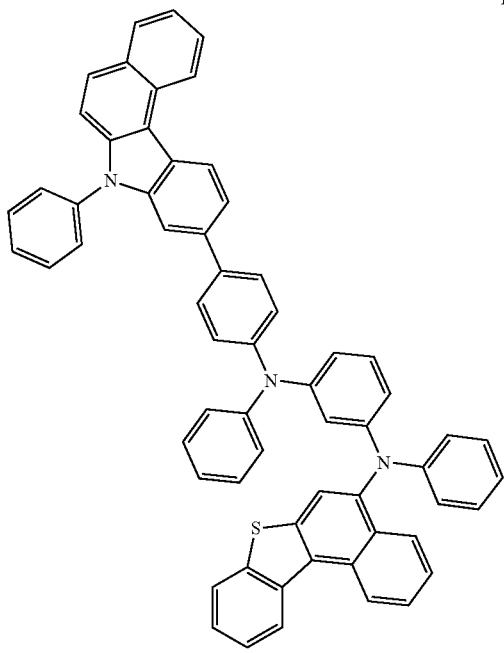
P-102
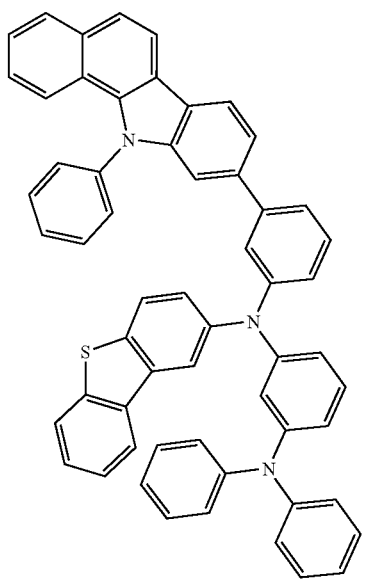

-continued

P-103
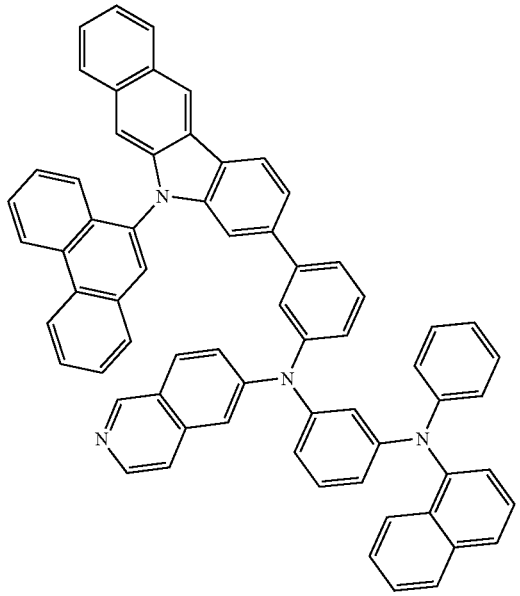

P-105
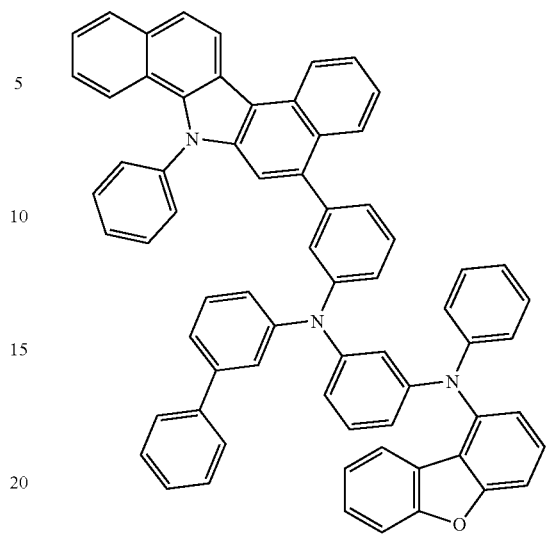

P-104
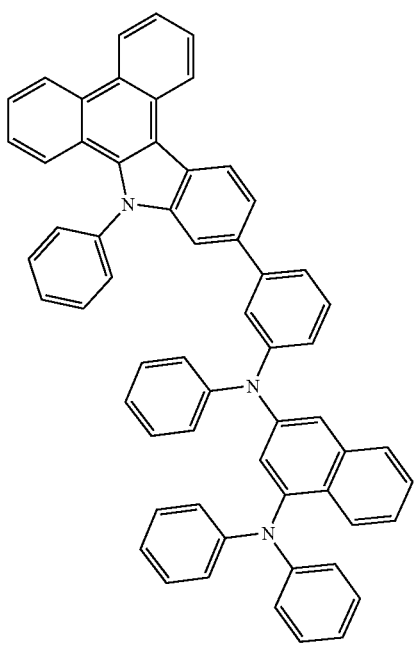

In another aspect of the present invention, the present invention provides an organic electric element comprising a first electrode, a second electrode, and an organic material layer formed between the first electrode and the second electrode, wherein the organic material layer comprises the compound represented by the formula 1.

The organic material layer comprises at least one of a hole injection layer, one or more hole transport layers, an emission-auxiliary layer, a light emitting layer, an electron transport auxiliary layer, one or more electron transport layers and an electron injection layer. At least one layer of the above layers may comprise the compound represented by the formulas 1 to 4 as a single compound or as a mixture of two or more kinds. Preferably, the compound represented by the formulas 1 to 4 may be material of one or more hole transport layers or/and the emission-auxiliary layer.

In addition, the present invention, the present invention provides an organic electric element further comprising a layer for improving luminous efficiency formed on at least one side of sides of the first electrode and the second electrode, wherein at least one side is not facing the organic material layer, and the organic material layer may be formed by any one of the processes of spin coating, nozzle printing, inkjet printing, slot coating, dip coating or roll-to-roll.

Hereinafter, synthesis example of the compound represented by Formula 1, wherein the compound is used as material of the organic material layer, and preparation method of an organic electric element according to one embodiment of the present invention will be described in detail by way of examples. However, the present invention is not limited to the following examples.

SYNTHESIS EXAMPLE

As shown in Reaction Scheme 1 below, the compounds (final products) represented by Formula 1 according to the present invention can be synthesized by reacting Sub 1 with Sub 2, but there is no limitation thereto. The symbols of $Ar^1$ to $Ar^4$, $R^1$ to $R^3$, $L^1$, m, n and o and the like are the same as defined in Formula 1.

<Reaction Scheme 1>

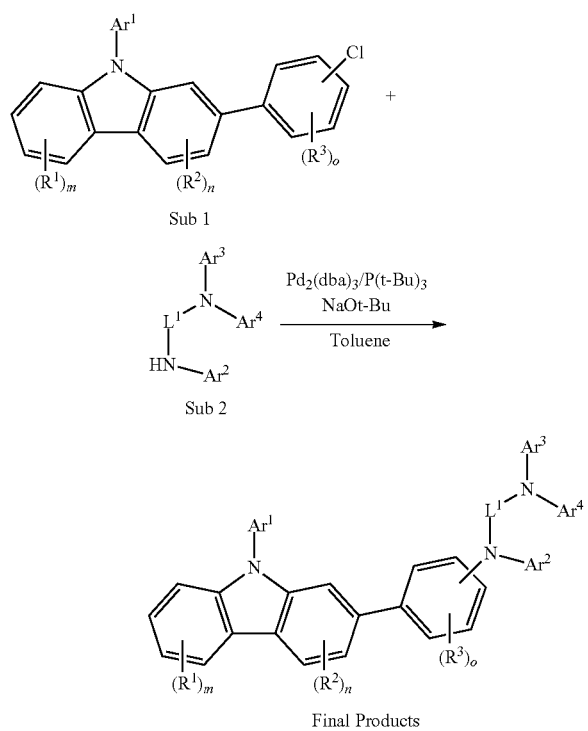

I. Synthesis of Sub 1

Sub 1 of the Reaction Scheme 1 can be synthesized according to the reaction routes of the following Reaction Schemes 2 and 3, but it is not limited thereto.

<Reaction Scheme 2>

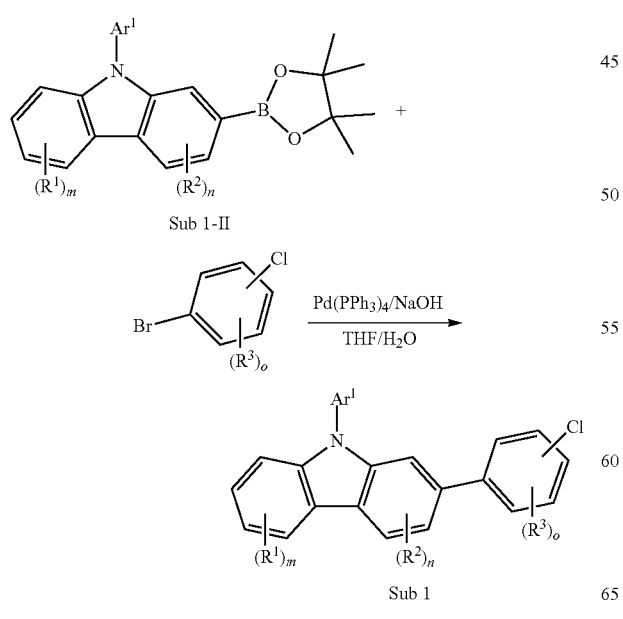

<Reaction Scheme 3>

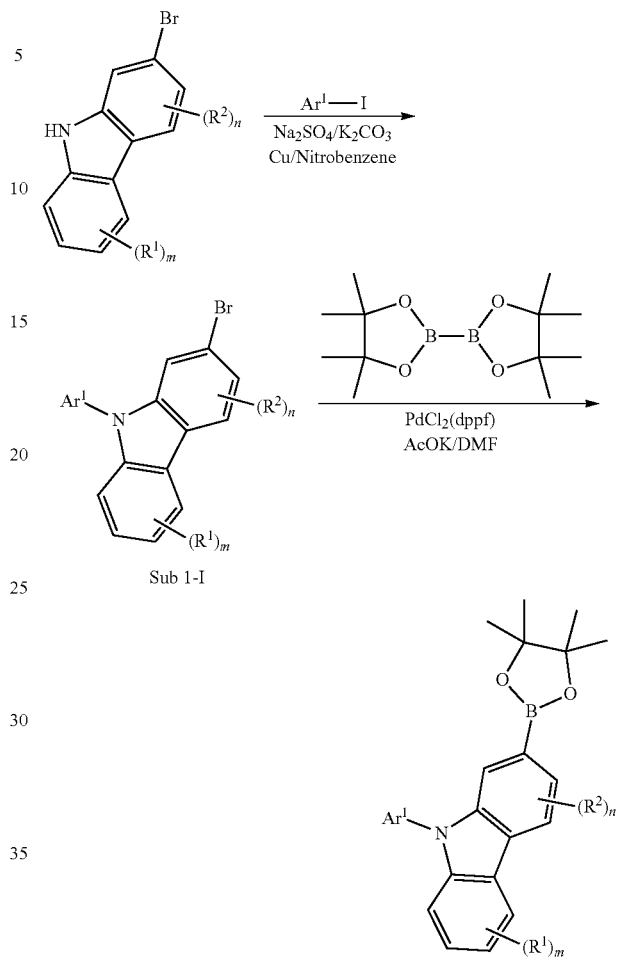

The synthesis method disclosed in Korean Patent No. 10-1535606 (registered on Jul. 23, 2015) owned by the applicant of the present invention was used for the synthesis of Sub 1-II (Reaction Scheme 3).

Synthesis examples of the compounds belonging to Sub 1 are as follows.

1. Synthesis Example of Sub 1-1

<Reaction Scheme 4>

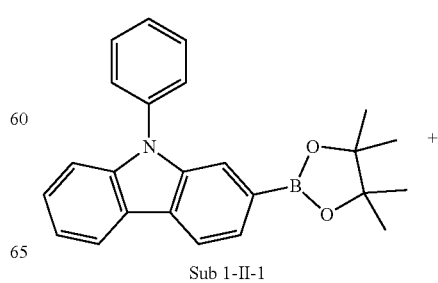

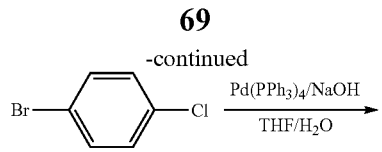

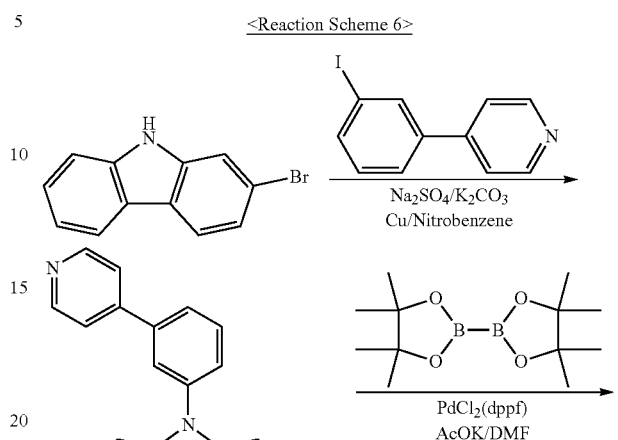

3. Synthesis Example of Sub 1-9

<Reaction Scheme 6>

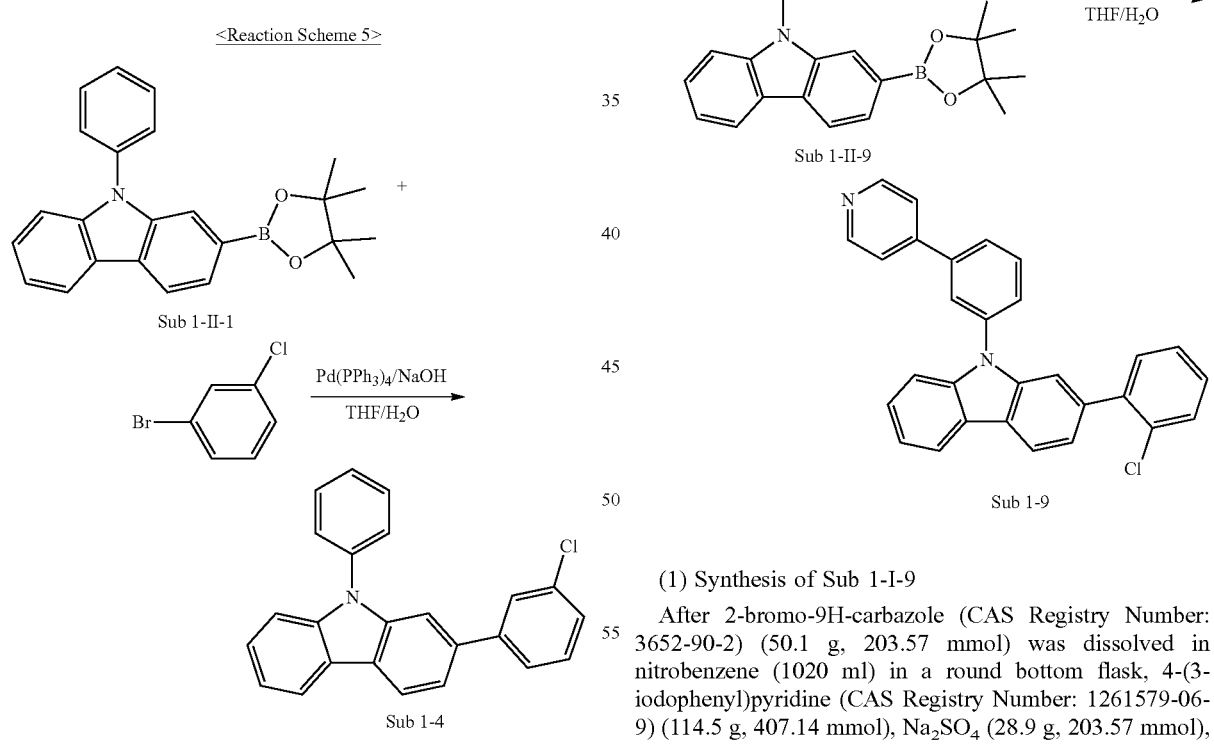

After Sub 1-II-1 (CAS Registry Number: 1246669-45-3) (64.3 g, 174.13 mmol) was dissolved in THF (640 ml) in a round bottom flask, 1-bromo-4-chlorobenzene (CAS Registry Number: 106-39-8) (40 g, 208.95 mmol), Pd(PPh$_3$)$_4$ (6 g, 5.22 mmol), NaOH (20.9 g, 522.38 mmol), water (320 ml) were added to the solution, and then the mixture was stirred at 80° C. When the reaction was completed, the reaction product was extracted with CH$_2$Cl$_2$ and water, and then the organic layer was dried with MgSO$_4$ and concentrated. Then, the concentrate was applied to silica gel column and recrystallized to obtain 49.9 g (yield: 81%) of the product.

2. Synthesis Example of Sub 1-4

<Reaction Scheme 5>

1-bromo-3-chlorobenzene (CAS Registry Number: 108-37-2) (42.6 g, 222.60 mmol), Pd(PPh$_3$)$_4$ (6.4 g, 5.57 mmol), NaOH (22.3 g, 556.50 mmol), THF (680 ml), and water (340 ml) were added to Sub 1-II-1 (CAS Registry Number: 1246669-45-3) (68.5 g, 185.50 mmol), and then the same method as in synthesis of Sub 1-1 were proceeded to obtain 54.5 g (yield: 83%) of the product.

(1) Synthesis of Sub 1-I-9

After 2-bromo-9H-carbazole (CAS Registry Number: 3652-90-2) (50.1 g, 203.57 mmol) was dissolved in nitrobenzene (1020 ml) in a round bottom flask, 4-(3-iodophenyl)pyridine (CAS Registry Number: 1261579-06-9) (114.5 g, 407.14 mmol), Na$_2$SO$_4$ (28.9 g, 203.57 mmol), K$_2$CO$_3$ (28.1 g, 203.57 mmol), Cu (3.9 g, 61.1 mmol) were added to the solution and the mixture was stirred at 200° C. When the reaction was completed, nitrobenzene was removed by distillation and the resultant was extracted with CH$_2$Cl$_2$ and water. Then, the organic layer was dried with MgSO$_4$ and concentrated. The concentrate was applied to silica gel column and recrystallized to obtain 50.4 g (yield: 62%) of the product.

(2) Synthesis of Sub 1-II-9

After Sub 1-I-9 (50.4 g, 126.22 mmol) obtained in the above synthesis was dissolved in DMF (630 ml) in a round bottom flask, bis(pinacolato)diboron (35.3 g, 138.85 mmol), Pd(dppf)Cl$_2$ (3.1 g, 3.79 mmol), KOAc (37.2 g, 378.67 mmol) were added to the solution and the mixture was stirred at 90° C. When the reaction was completed, DMF was removed by distillation and the resultant was extracted with ether and water. Then the organic layer was dried with MgSO$_4$ and concentrated. The concentrate was applied to silica gel column and recrystallized to obtain 42.8 g (yield: 76%) of the product.

(3) Synthesis of Sub 1-9

After 1-bromo-2-chlorobenzene (CAS Registry Number: 694-80-4) (18.4 g, 95.89 mmol), Pd(PPh$_3$)$_4$ (3.3 g, 2.88 mmol), NaOH (11.5 g, 287.66 mmol), THF (320 ml), water (160 ml) were added to Sub 1-II-9 (42.8 g, 95.89 mmol) obtained in the above synthesis, 34.3 g (yield: 83%) of the product was obtained by proceeding with the same method as in synthesis of Sub 1-1.

4. Synthesis Example of Sub 1-16

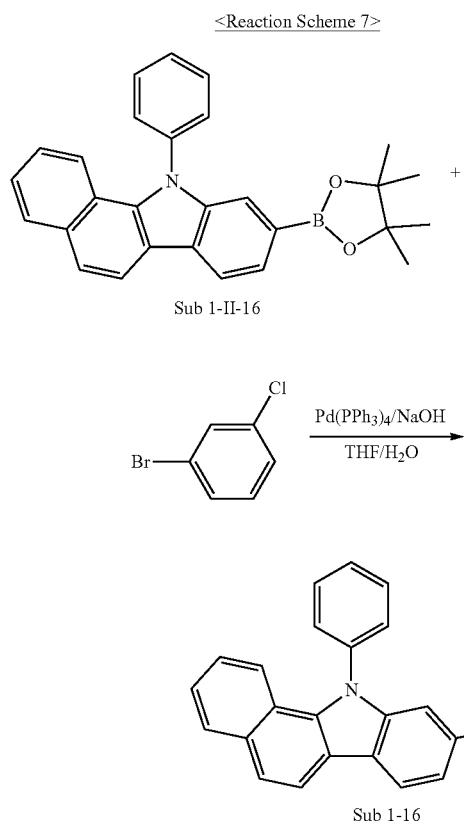

After 1-bromo-3-chlorobenzene (CAS Registry Number: 108-37-2) (8.1 g, 42.35 mmol), Pd(PPh$_3$)$_4$ (1.2 g, 1.06 mmol), NaOH (4.2 g, 105.88 mmol), THF (130 ml), water (65 ml) were added to Sub 1-II-16 (CAS Registry Number: 1646271-66-0) (14.8 g, 35.29 mmol), 11 g (yield: 77%) of the product was obtained by proceeding with the same method as in synthesis of Sub 1-1.

5. Synthesis Example of Sub 1-29

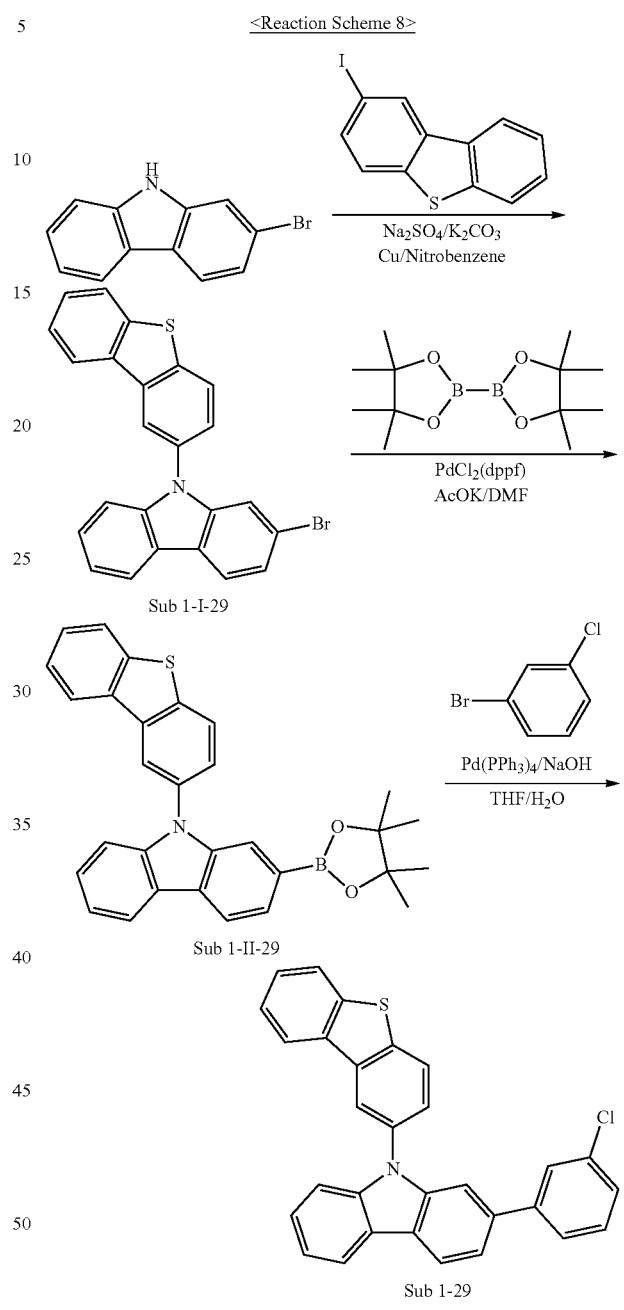

(1) Synthesis of Sub 1-I-29

After 2-iododibenzo[b,d]thiophene (CAS Registry Number: 177586-41-3) (45.4 g, 146.28 mmol), Na$_2$SO$_4$ (10.4 g, 73.14 mmol), K$_2$CO$_3$ (10.1 g, 73.14 mmol), Cu (1.4 g, 21.94 mmol), nitrobenzene (365 ml) were added to 2-bromo-9H-carbazole (CAS Registry Number: 3652-90-2) (18 g, 73.14 mmol), 18.8 g (yield: 60%) of the product was obtained by proceeding with the same method as in synthesis of Sub 1-I-9.

(2) Synthesis of Sub 1-II-29

After bis(pinacolato)diboron (12.3 g, 48.28 mmol), Pd(dppf)Cl$_2$ (1.1 g, 1.32 mmol), KOAc (12.9 g, 131.67 mmol), DMF (220 ml) were added to Sub 1-I-9 (18.8 g, 43.89 mmol) obtained in the above synthesis, 16.9 g (yield: 81%) of the product was obtained by proceeding with the same method as in synthesis of Sub 1-11-9.

(3) Synthesis of Sub 1-29

After 1-bromo-3-chlorobenzene (CAS Registry Number: 108-37-2) (6.81 g, 35.55 mmol), Pd(PPh$_3$)$_4$ (1.2 g, 1.07 mmol), NaOH (4.3 g, 106.64 mmol), THF (120 ml), water (60 ml) were added to Sub 1-II-29 (16.9 g, 35.55 mmol) obtained in the above synthesis, 14.2 g (yield: 87%) of the product was obtained by proceeding with the same method as in synthesis of Sub 1-1.

The compounds belonging to Sub 1 may be, but not limited to, the following compounds, and Table 1 shows FD-MS (Field Desorption-Mass Spectrometry) values of them.

Sub 1-1

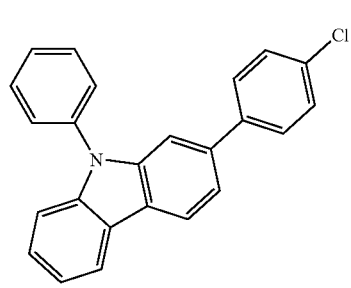

Sub 1-2

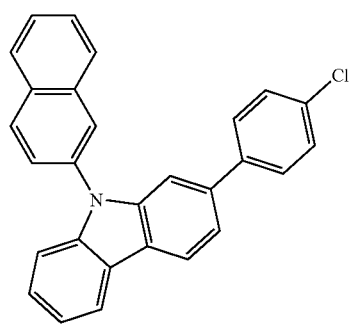

Sub 1-3

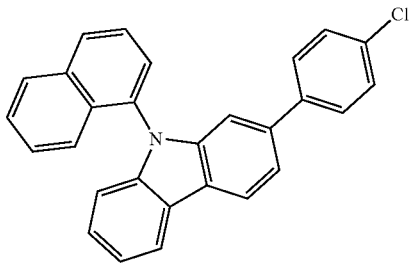

Sub 1-4

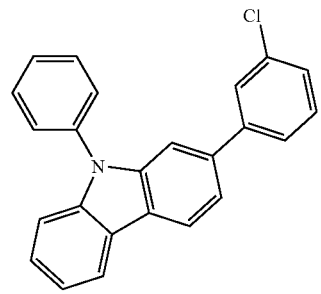

Sub 1-5

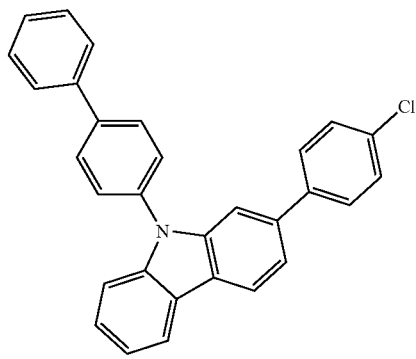

Sub 1-6

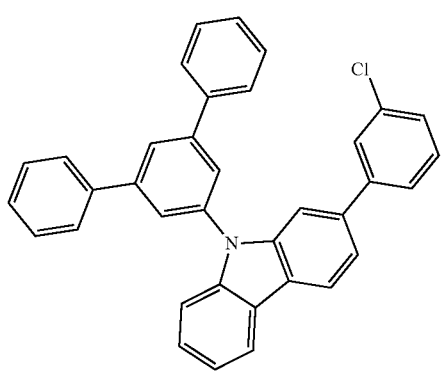

Sub 1-7

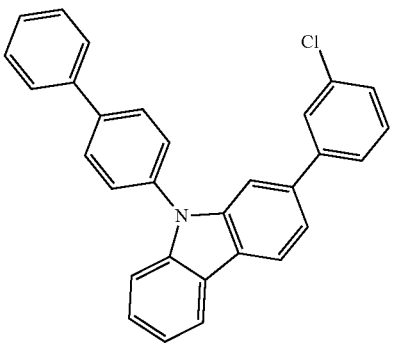

Sub 1-8

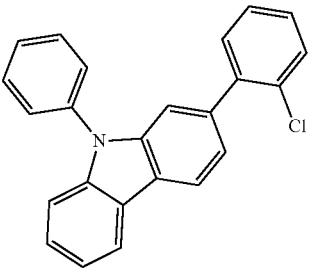

Sub 1-9
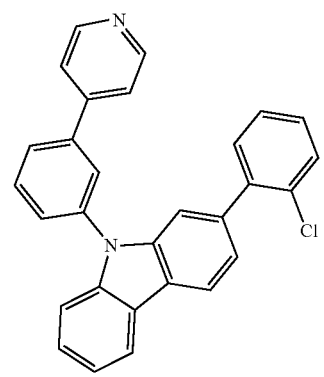
Sub 1-10
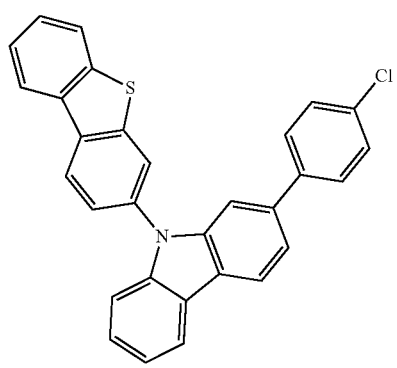
Sub 1-11
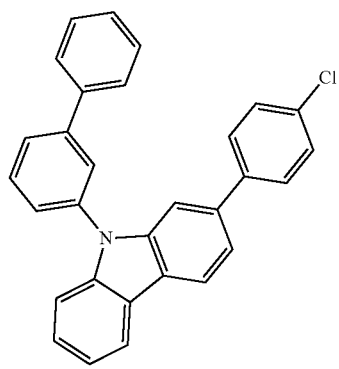
Sub 1-12
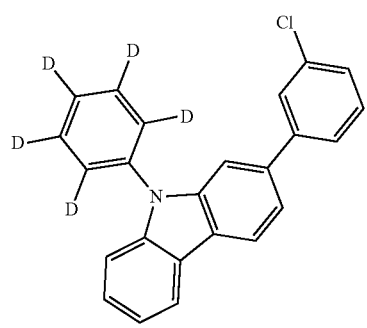
Sub 1-13
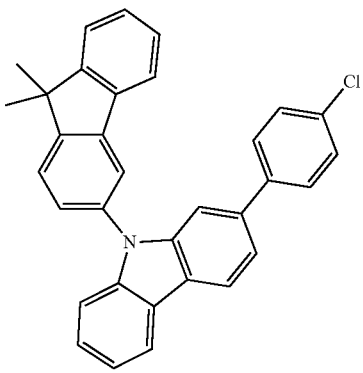
Sub 1-14
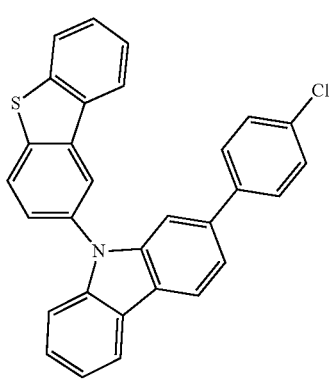
Sub 1-15
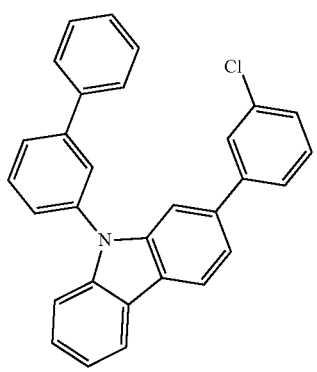
Sub 1-16
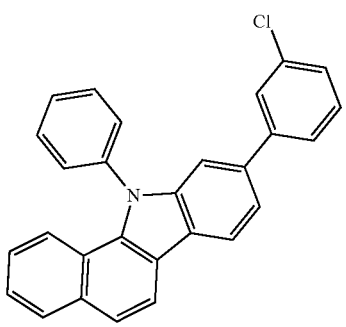

| | |
|---|---|
| Sub 1-17 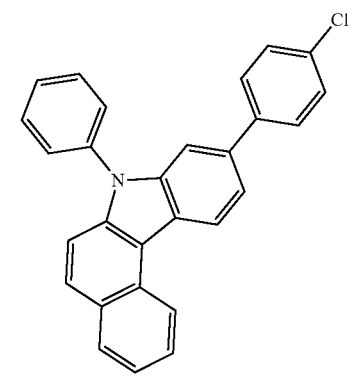 | Sub 1-21 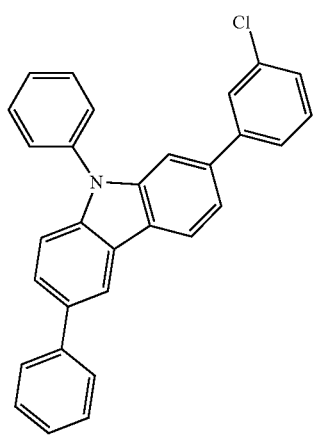 |
| Sub 1-18 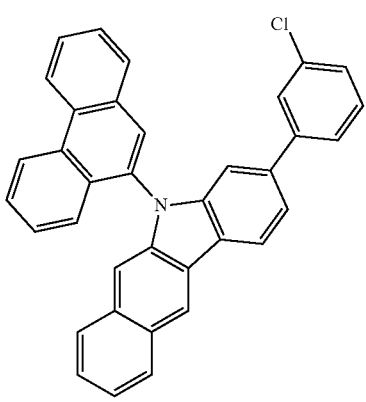 | Sub 1-22 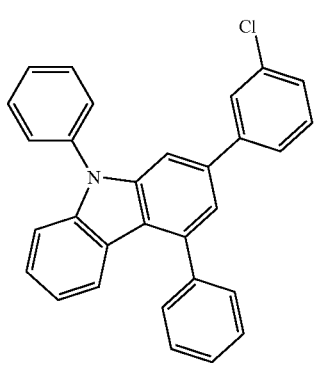 |
| Sub 1-19 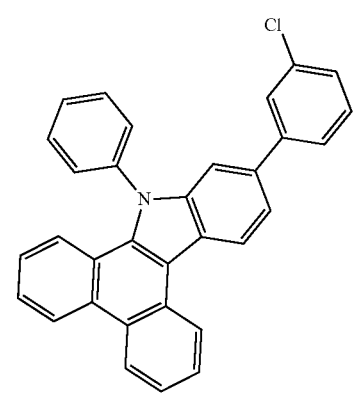 | Sub 1-23 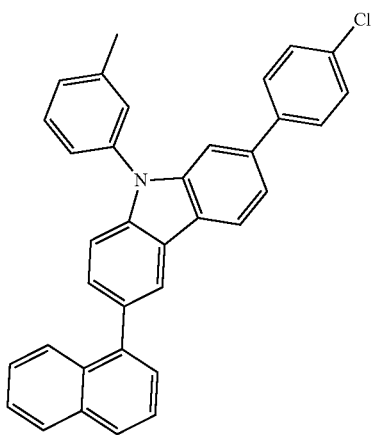 |
| Sub 1-20 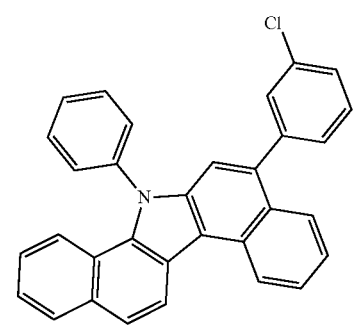 | Sub 1-24 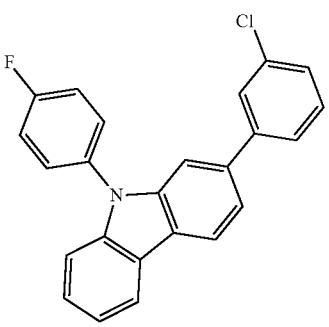 |

Sub 1-25
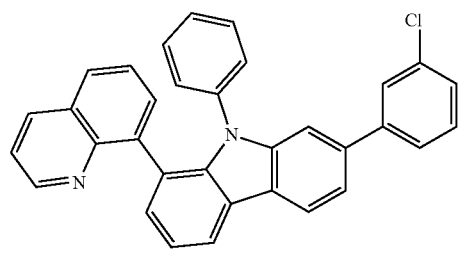
Sub 1-26
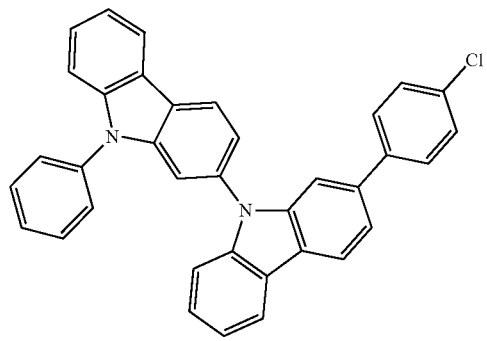
Sub 1-27
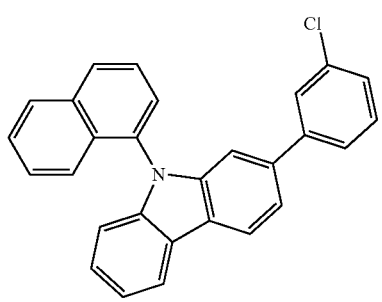
Sub 1-28
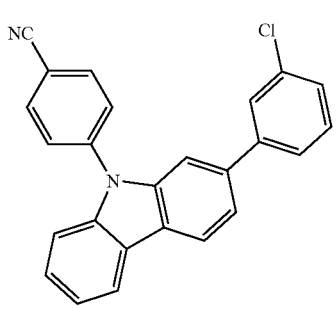
Sub 1-29
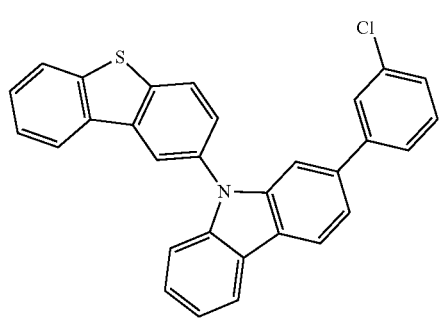
Sub 1-30
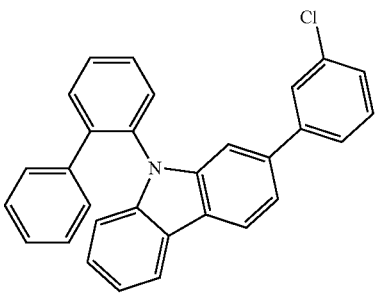
Sub 1-31
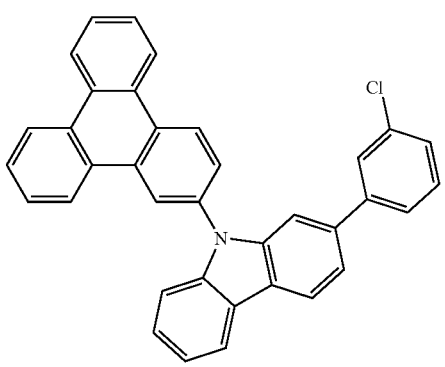
Sub 1-32
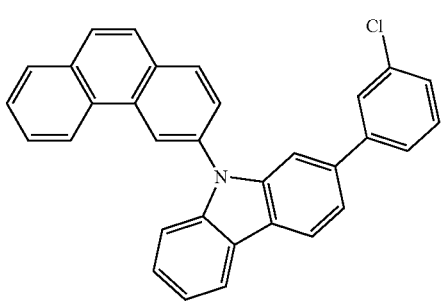
Sub 1-33
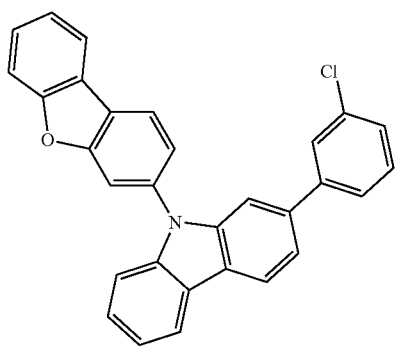

TABLE 1

| Compound | FD-MS | Compound | FD-MS |
| --- | --- | --- | --- |
| Sub 1-1 | m/z = 353.10($C_{24}H_{16}ClN$ = 353.85) | Sub 1-2 | m/z = 403.11($C_{28}H_{18}ClN$ = 403.91) |
| Sub 1-3 | m/z = 403.11($C_{28}H_{18}ClN$ = 403.91) | Sub 1-4 | m/z = 353.10($C_{24}H_{16}ClN$ = 353.85) |
| Sub 1-5 | m/z = 429.13($C_{30}H_{20}ClN$ = 429.95) | Sub 1-6 | m/z = 505.16($C_{36}H_{24}ClN$ = 506.05) |
| Sub 1-7 | m/z = 429.13($C_{30}H_{20}ClN$ = 429.95) | Sub 1-8 | m/z = 353.10($C_{24}H_{16}ClN$ = 353.85) |
| Sub 1-9 | m/z = 430.12($C_{29}H_{19}ClN_2$ = 430.94) | Sub 1-10 | m/z = 459.08($C_{30}H_{18}ClNS$ = 459.99) |
| Sub 1-11 | m/z = 429.13($C_{30}H_{20}ClN$ = 429.95) | Sub 1-12 | m/z = 358.13($C_{24}H_{11}D_5ClN$ = 358.88) |
| Sub 1-13 | m/z = 469.16($C_{33}H_{24}ClN$ = 470.01) | Sub 1-14 | m/z = 459.08($C_{30}H_{18}ClNS$ = 459.99) |
| Sub 1-15 | m/z = 429.13($C_{30}H_{20}ClN$ = 429.95) | Sub 1-16 | m/z = 403.11($C_{28}H_{18}ClN$ = 403.91) |
| Sub 1-17 | m/z = 403.11($C_{28}H_{18}ClN$ = 403.91) | Sub 1-18 | m/z = 503.14($C_{36}H_{22}ClN$ = 504.03) |
| Sub 1-19 | m/z = 453.13($C_{32}H_{20}ClN$ = 453.97) | Sub 1-20 | m/z = 453.13($C_{32}H_{20}ClN$ = 453.97) |
| Sub 1-21 | m/z = 429.13($C_{30}H_{20}ClN$ = 429.95) | Sub 1-22 | m/z = 429.13($C_{30}H_{20}ClN$ = 429.95) |
| Sub 1-23 | m/z = 493.16($C_{35}H_{24}ClN$ = 494.03) | Sub 1-24 | m/z = 371.09($C_{24}H_{15}ClFN$ = 371.84) |
| Sub 1-25 | m/z = 480.14($C_{33}H_{21}ClN_2$ = 481.00) | Sub 1-26 | m/z = 518.15($C_{36}H_{23}ClN_2$ = 519.04) |
| Sub 1-27 | m/z = 403.11($C_{28}H_{18}ClN$ = 403.91) | Sub 1-28 | m/z = 378.09($C_{25}H_{15}ClN_2$ = 378.86) |
| Sub 1-29 | m/z = 459.08($C_{30}H_{18}ClNS$ = 459.99) | Sub 1-30 | m/z = 429.13($C_{30}H_{20}ClN$ = 429.95) |
| Sub 1-31 | m/z = 503.14($C_{36}H_{22}ClN$ = 504.03) | Sub 1-32 | m/z = 453.13($C_{32}H_{20}ClN$ = 453.97) |
| Sub 1-33 | m/z = 443.11($C_{30}H_{18}ClNO$ = 443.93) | | |

II. Synthesis of Sub 2

Sub 2 of the Reaction Scheme 1 can be synthesized according to the reaction route of the following Reaction Scheme 9, but there is no limitation thereto.

Synthesis examples of the compounds belonging to Sub 2 are as follows.

1. Synthesis Example of Sub 2-7

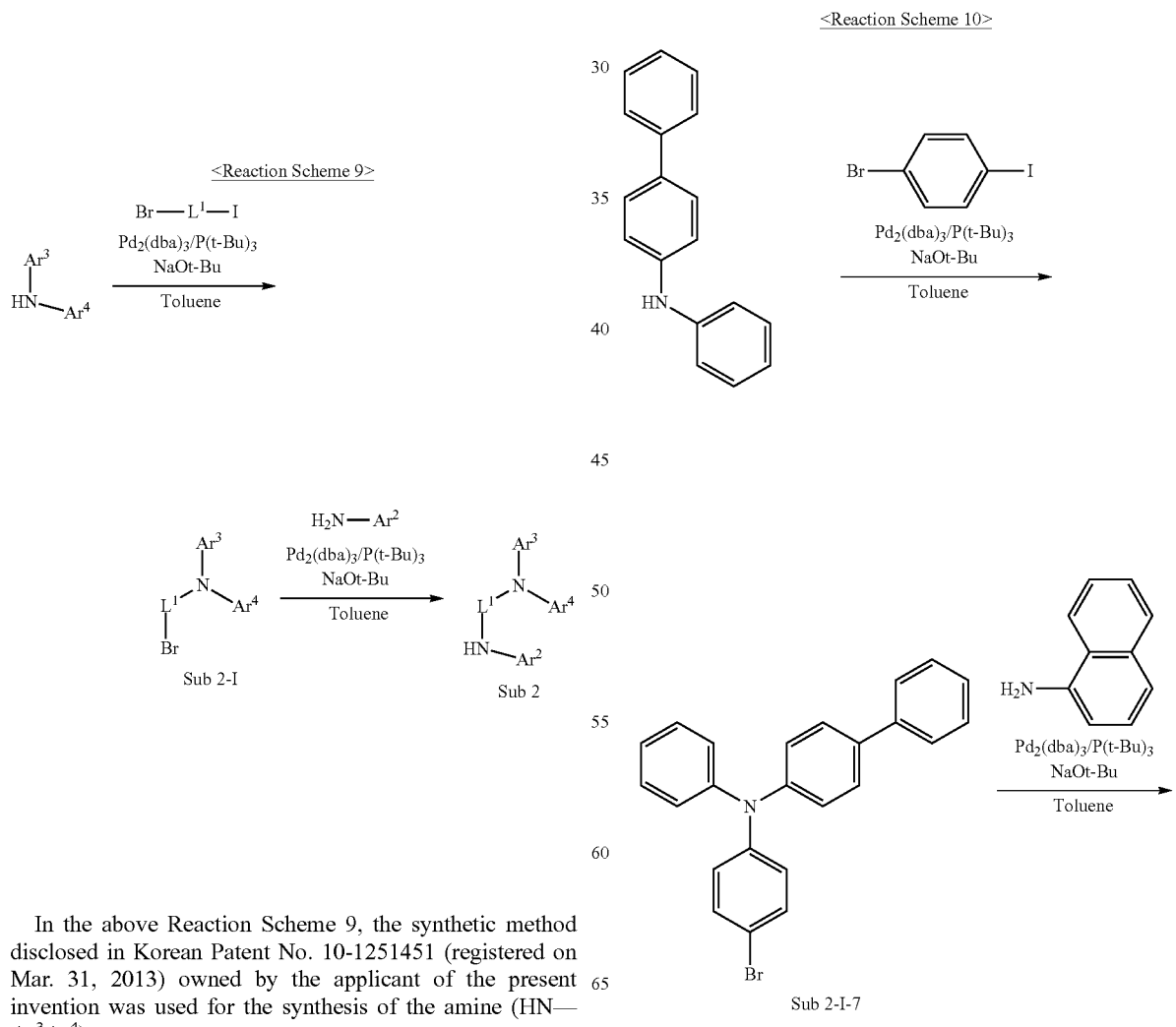

In the above Reaction Scheme 9, the synthetic method disclosed in Korean Patent No. 10-1251451 (registered on Mar. 31, 2013) owned by the applicant of the present invention was used for the synthesis of the amine (HN—$Ar^3Ar^4$) reactant.

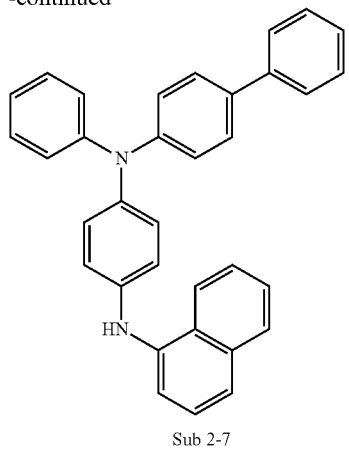

Sub 2-7

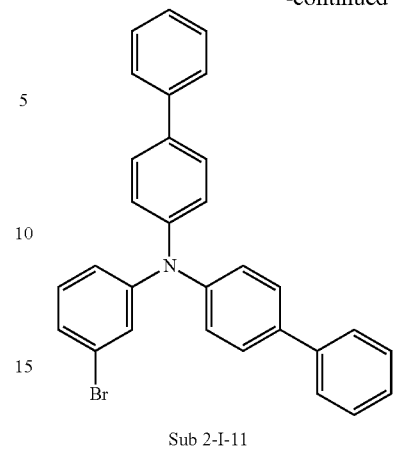

Sub 2-I-11

(1) Synthesis of Sub 2-I-7

After N-phenyl-[1,1'-biphenyl]-4-amine (CAS Registry Number: 32228-99-2) (13.1 g, 53.40 mmol) was dissolved in toluene (445 ml) in a round bottom flask, 1-bromo-4-iodobenzene (CAS Registry Number: 589-87-7) (22.7 g, 80.10 mmol), $Pd_2(dba)_3$ (1.5 g, 1.60 mmol), 50% P(t-Bu)$_3$ (2.1 ml, 4.27 mmol), NaOt-Bu (15.4 g, 160.19 mmol) were added to the solution and the mixture was stirred at 70° C. When the reaction was completed, the reaction product was extracted with $CH_2Cl_2$ and water, and then the organic layer was dried with $MgSO_4$ and concentrated. Then, the concentrate was applied to silica gel column and recrystallized to obtain 15.6 g (yield: 73%) of the product.

(2) Synthesis of Sub 2-7

After Sub 2-I-7 (15.6 g, 38.97 mmol) was dissolved in toluene (325 ml) in a round bottom flask, naphthalen-1-amine (CAS Registry Number: 134-32-7) (8.4 g, 58.45 mmol), $Pd_2(dba)_3$ (1.1 g, 1.17 mmol), 50% P(t-Bu)$_3$ (1.5 ml, 3.12 mmol), NaOt-Bu (11.2 g, 116.91 mmol) were added the solution and the mixture was stirred at 100° C. When the reaction was completed, the reaction product was extracted with $CH_2Cl_2$ and water, and then the organic layer was dried with $MgSO_4$ and concentrated. Then, the concentrate was applied to silica gel column and recrystallized to obtain 14.1 g (yield: 78%) of the product.

2. Synthesis Example of Sub 2-11

<Reaction Scheme 11>

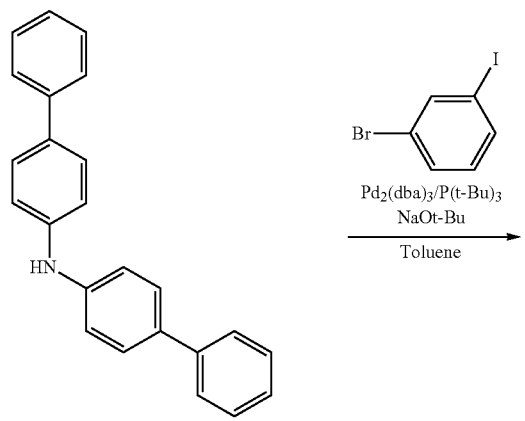

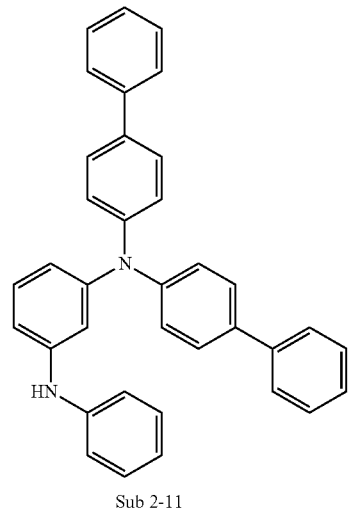

Sub 2-11

(1) Synthesis of Sub 2-I-11

After 1-bromo-3-iodobenzene (CAS Registry Number: 591-18-4) (45.29 g, 160.07 mmol), $Pd_2(dba)_3$ (2.9 g, 3.2 mmol), 50% P(t-Bu)$_3$ (4.2 ml, 8.54 mmol), NaOt-Bu (30.8 g, 320.14 mmol), toluene (890 ml) were added to di([1,1'-biphenyl]-4-yl)amine (CAS Registry Number: 102113-98-4) (34.3 g, 106.71 mmol), 36.1 g (yield: 71%) of the product was obtained by proceeding with the same method as in synthesis of Sub 2-I-7.

(2) Synthesis of Sub 2-11

After aniline (CAS Registry Number: 62-53-3) (10.6 g, 113.66 mmol), $Pd_2(dba)_3$ (2.1 g, 2.27 mmol), 50% P(t-Bu)$_3$ (3 ml, 6.06 mmol), NaOt-Bu (21.9 g, 227.32 mmol), toluene (630 ml) were added to Sub 2-I-11 (36.1 g, 75.77 mmol) obtained in the above synthesis, 29.6 g (yield: 80%) of the product was obtained by proceeding with the same method as in synthesis of Sub 2-I-7.

3. Synthesis Example of Sub 2-14

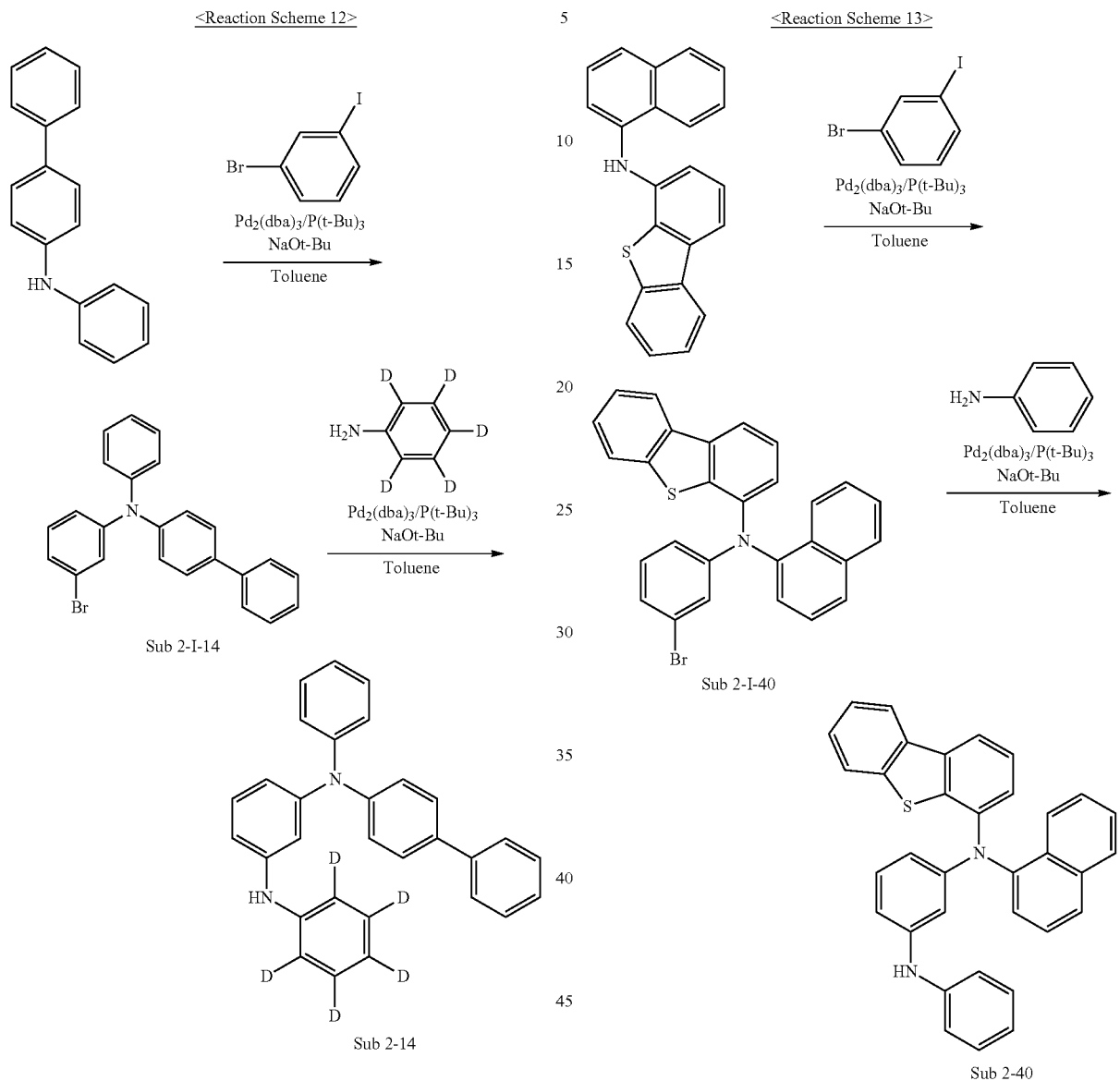

(2) Synthesis of Sub 2-I-14

After 1-bromo-3-iodobenzene (CAS Registry Number: 591-18-4) (21.6 g, 76.43 mmol), $Pd_2(dba)_3$ (1.4 g, 1.53 mmol), 50% P(t-Bu) ((2 ml, 4.08 mmol), NaOt-Bu (14.7 g, 152.86 mmol), toluene (425 ml) were added to N-phenyl-[1,1-biphenyl]-4-amine (CAS Registry Number: 32228-99-2) (12.5 g, 50.95 mmol), 15.3 g (yield: 75%) of the product was obtained by proceeding with the same method as in synthesis of Sub 2-I-7.

(2) Synthesis of Sub 2-14

After benzen-$d_5$-amine (CAS Registry Number: 4165-61-1) (5.6 g, 57.33 mmol), $Pd_2(dba)_3$ (1.1 g, 1.15 mmol), 50% $P(t-Bu)_3$ (1.5 ml, 3.06 mmol), NaOt-Bu (11.02 g, 114.66 mmol), toluene (320 ml) were added to Sub 2-I-14 (15.3 g, 38.22 mmol) obtained in the above synthesis, 12.3 g (yield: 77%) of the product was obtained by proceeding with the same method as in synthesis of Sub 2-I-7.

4. Synthesis Example of Sub 2-40

(1) Synthesis of Sub 2-I-40

After 1-bromo-3-iodobenzene (CAS Registry Number: 591-18-4) (27.8 g, 98.18 mmol), $Pd_2(dba)_3$ (1.8 g, 1.96 mmol), 50% $P(t-Bu)_3$ (2.6 ml, 5.24 mmol), NaOt-Bu (18.87 g, 196.36 mmol), toluene (545 ml) were added to N-(naphthalen-1-yl)dibenzo[b,d]thiophen-4-amine (CAS Registry Number: 1464825-38-4) (21.3 g, 65.45 mmol), 21.7 g (yield: 69%) of the product was obtained by proceeding with the same method as in synthesis of Sub 2-I-7.

(2) Synthesis of Sub 2-40

After aniline (CAS Registry Number: 62-53-3) (6.31 g, 67.75 mmol), $Pd_2(dba)_3$ (1.24 g, 1.36 mmol), 50% $P(t-Bu)_3$ (1.8 ml, 3.61 mmol), NaOt-Bu (13 g, 135.51 mmol), toluene (375 ml) were added to Sub 2-I-40 (21.7 g, 45.17 mmol) obtained in the above synthesis, 18 g (yield: 81%) of the product was obtained by proceeding with the same method as in synthesis of Sub 2-I-7.

5. Synthesis Example of Sub 2-45

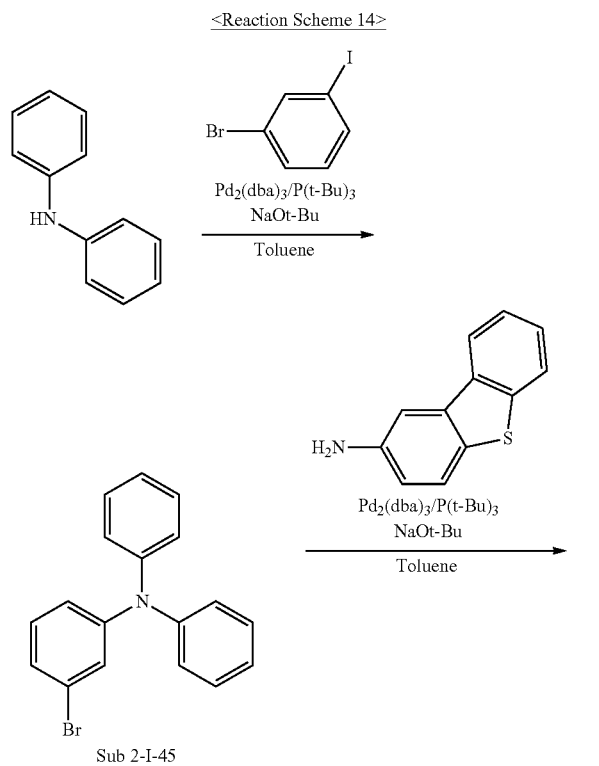

(1) Synthesis of Sub 2-I-45

After 1-bromo-3-iodobenzene (CAS Registry Number: 591-18-4) (45.6 g, 161.32 mmol), Pd$_2$(dba)$_3$ (3 g, 3.23 mmol), 50% P(t-Bu)$_3$ (4.2 ml, 8.60 mmol), NaOt-Bu (31 g, 322.64 mmol), toluene (895 ml) were added to diphenylamine (CAS Registry Number: 122-39-4) (18.2 g, 107.55 mmol), 23.7 g (yield: 68%) of the product was obtained by proceeding with the same method as in synthesis of Sub 2-I-7.

(2) Synthesis of Sub 2-45

After dibenzo[b,d]thiophen-2-amine (CAS Registry Number: 7428-91-3) (21.9 g, 109.65 mmol), Pd$_2$(dba)$_3$ (2 g, 2.19 mmol), 50% P(t-Bu)$_3$ (2.9 ml, 5.85 mmol), NaOt-Bu (21.1 g, 219.3 mmol), toluene (610 ml) were added to Sub 2-I-45 (23.7 g, 73.1 mmol) obtained in the above synthesis, 25.6 g (yield: 79%) of the product was obtained by proceeding with the same method as in synthesis of Sub 2-I-7.

6. Synthesis Example of Sub 2-58

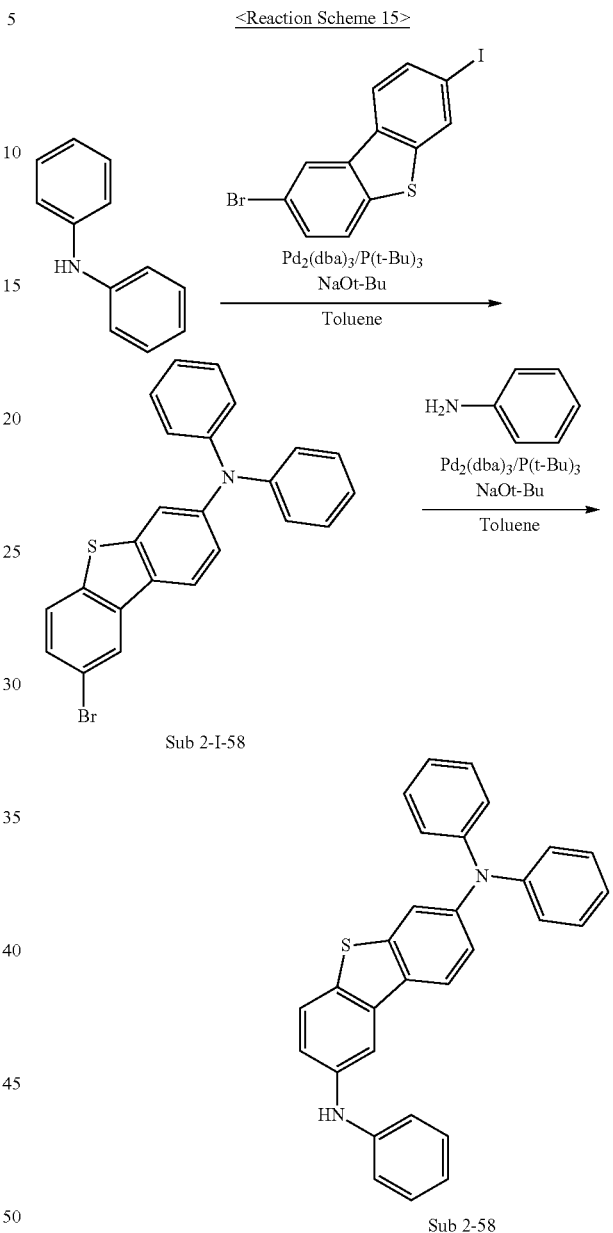

(1) Synthesis of Sub 2-I-58

After 2-bromo-7-iododibenzo[b,d]thiophene (CAS Registry Number: 1910080-84-0) (34.5 g, 88.64 mmol), Pd$_2$(dba)$_3$ (1.6 g, 1.77 mmol), 50% P(t-Bu)$_3$ (2.3 ml, 4.73 mmol), NaOt-Bu (17 g, 177.27 mmol), toluene (490 ml) were added to diphenylamine (CAS Registry Number: 122-39-4) (10 g, 59.09 mmol), 21.1 g (yield: 83%) of the product was obtained by proceeding with the same method as in synthesis of Sub 2-1-7.

(2) Synthesis of Sub 2-58

After aniline (CAS Registry Number: 62-53-3) (6.9 g, 73.54 mmol), Pd$_2$(dba)$_3$ (1.4 g, 1.47 mmol), 50% P(t-Bu)$_3$ (1.9 ml, 3.92 mmol), NaOt-Bu (14.1 g, 147.09 mmol), toluene (410 ml) were added to Sub 2-I-58 (21.1 g, 49.03 mmol) obtained in the above synthesis, 18.4 g (yield: 85%)

7. Synthesis Example of Sub 2-66

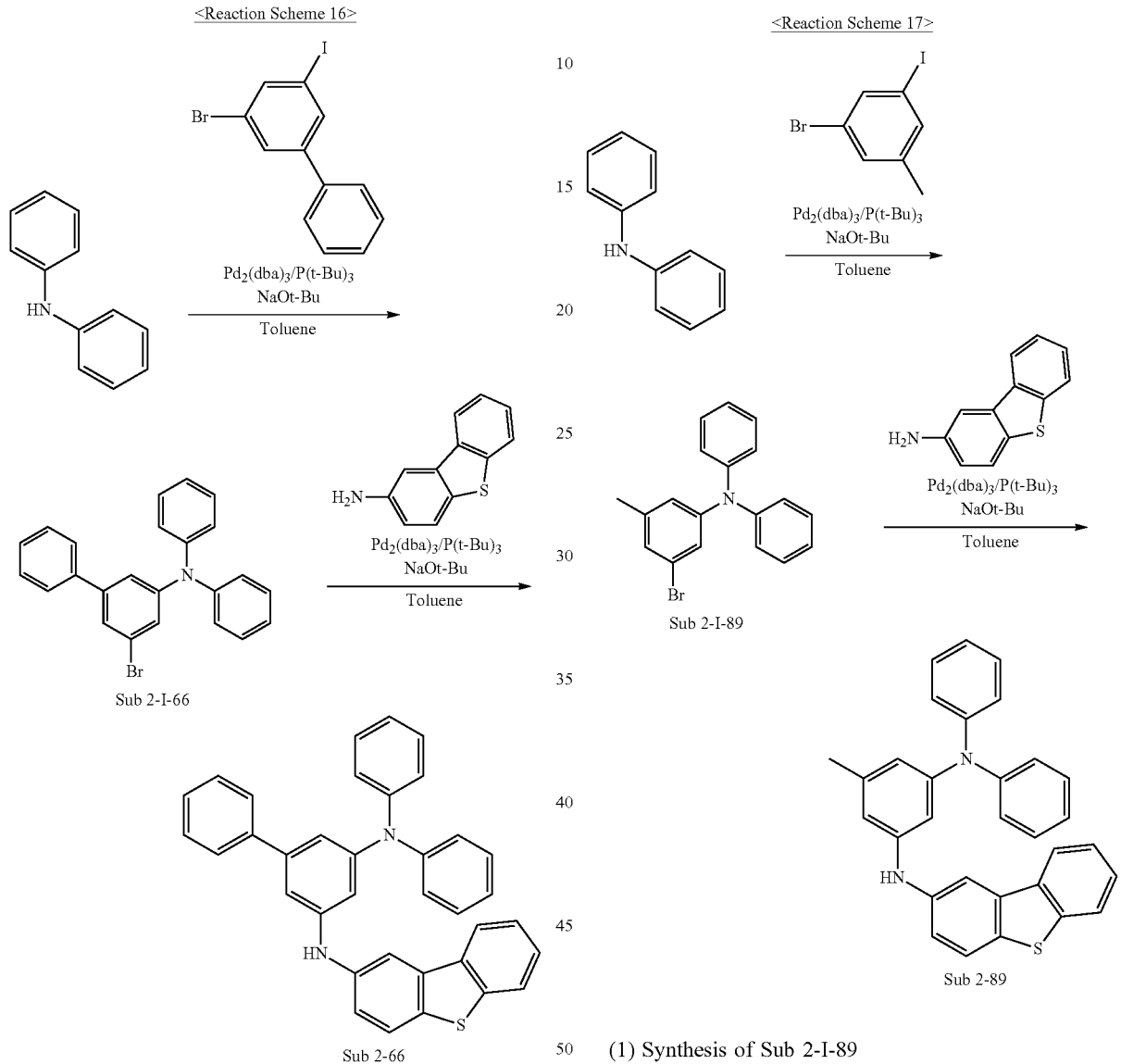

(1) Synthesis of Sub 2-I-66

After 3-bromo-5-iodo-1,1'-biphenyl (CAS Registry Number: 136649-44-0) (35 g, 97.50 mmol), Pd$_2$(dba)$_3$ (1.8 g, 1.95 mmol), 50% P(t-Bu)$_3$ (2.5 ml, 5.2 mmol), NaOt-Bu (18.7 g, 195.00 mmol), toluene (540 ml) were added to diphenylamine (CAS Registry Number: 122-39-4) (11 g, 65.00 mmol), 18.7 g (yield: 72%) of the product was obtained by proceeding with the same method as in synthesis of Sub 2-I-7.

(2) Synthesis of Sub 2-66

After dibenzo[b,d]thiophen-2-amine (CAS Registry Number: 7428-91-3) (14 g, 70.07 mmol), Pd$_2$(dba)$_3$ (1.3 g, 1.40 mmol), 50% P(t-Bu)$_3$ (1.8 ml, 3.74 mmol), NaOt-Bu (13.5 g, 140.14 mmol), toluene (390 ml) were added to Sub 2-I-66 (18.7 g, 46.71 mmol) obtained in the above synthesis, 18.4 g (yield: 76%) of the product was obtained by proceeding with the same method as in synthesis of Sub 2-I-7.

8. Synthesis Example of Sub 2-89

(1) Synthesis of Sub 2-I-89

After 1-bromo-3-iodo-5-methylbenzene (CAS Registry Number: 116632-38-3) (25.3 g, 85.09 mmol), Pd$_2$(dba)$_3$ (1.6 g, 1.70 mmol), 50% P(t-Bu)$_3$ (2.2 ml, 4.54 mmol), NaOt-Bu (16.4 g, 170.18 mmol), toluene (470 ml) were added to diphenylamine (CAS Registry Number: 122-39-4) (9.6 g, 56.73 mmol), 13.4 g (yield: 70%) of the product was obtained by proceeding with the same method as in synthesis of Sub 2-I-7.

(2) Synthesis of Sub 2-89

After dibenzo[b,d]thiophen-2-amine (CAS Registry Number: 7428-91-3) (11.8 g, 59.42 mmol), Pd$_2$(dba)$_3$ (1.1 g, 1.19 mmol), 50% P(t-Bu)$_3$ (1.5 ml, 3.17 mmol), NaOt-Bu (11.4 g, 118.85 mmol), toluene (330 ml) were added to Sub 2-I-89 (13.4 g, 39.62 mmol) obtained in the above synthesis, 12.8 g (yield: 71%) of the product was obtained by proceeding with the same method as in synthesis of Sub 2-I-7.

The compounds belonging to Sub 2 may be, but not limited to, the following compounds, and Table 2 shows FD-MS (Field Desorption-Mass Spectrometry) values of them.
Sub 2-1
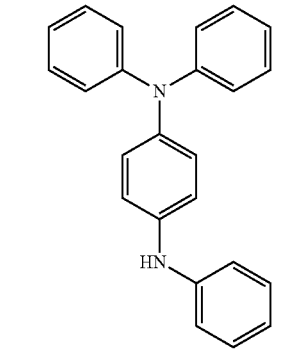
Sub 2-2
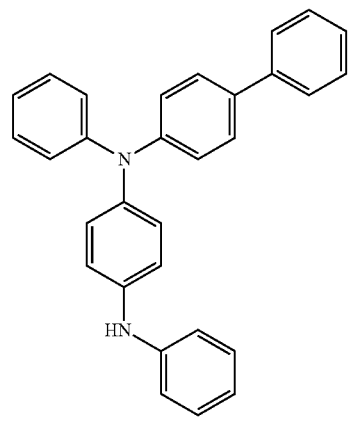
Sub 2-3
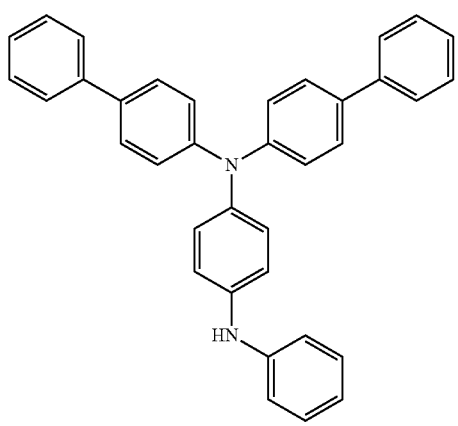
Sub 2-4
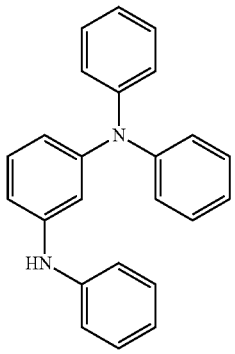
Sub 2-5
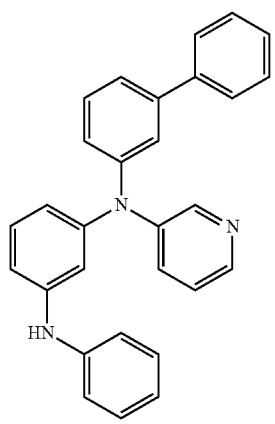
Sub 2-6
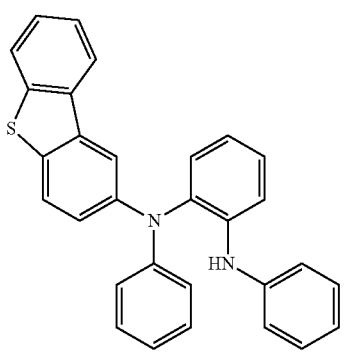
Sub 2-7
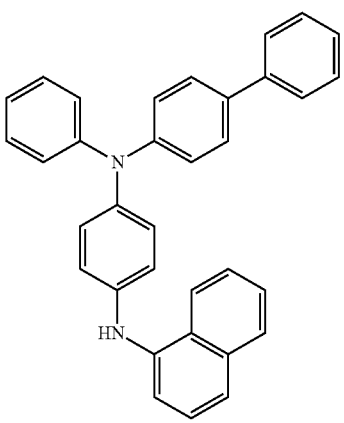

Sub 2-8
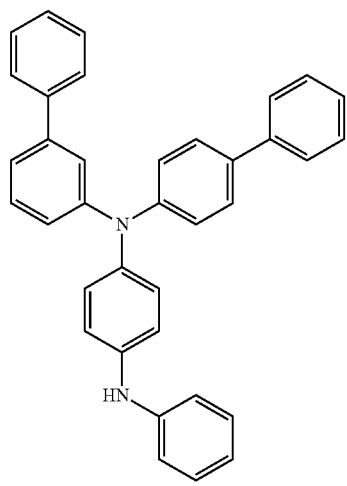
Sub 2-11
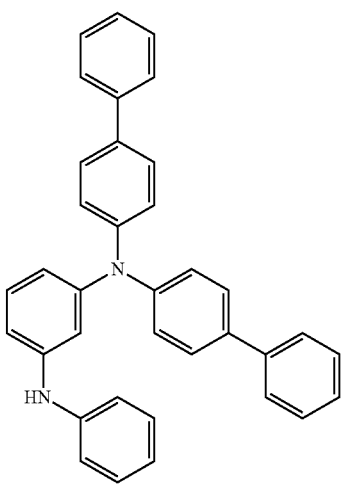
Sub 2-9
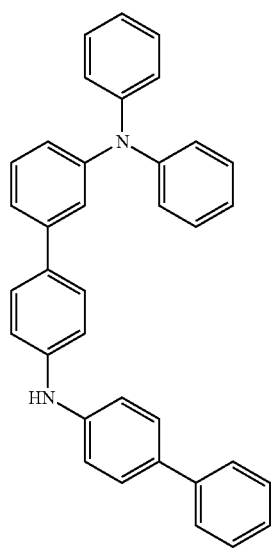
Sub 2-12
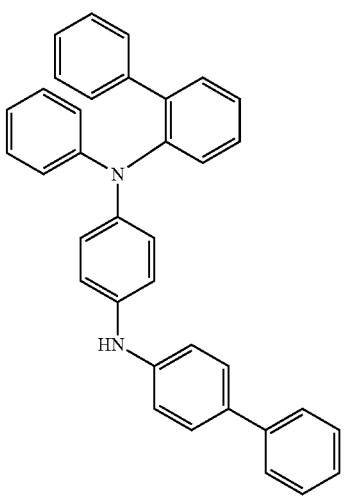
Sub 2-10
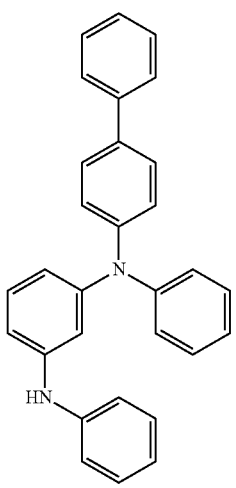
Sub 2-13
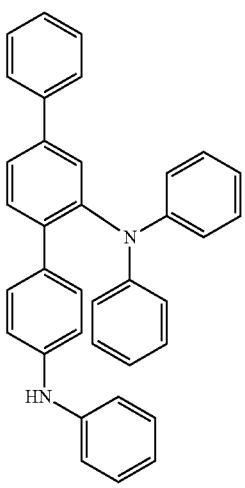

Sub 2-14
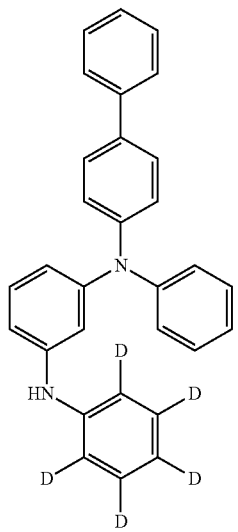
Sub 2-15
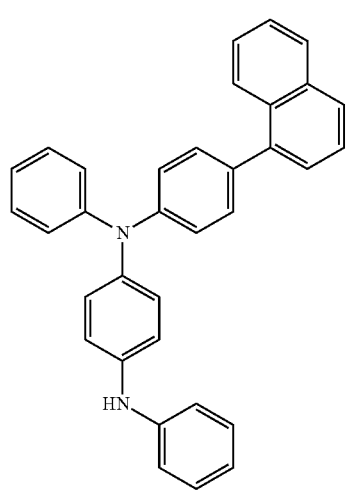
Sub 2-16
Sub 2-17
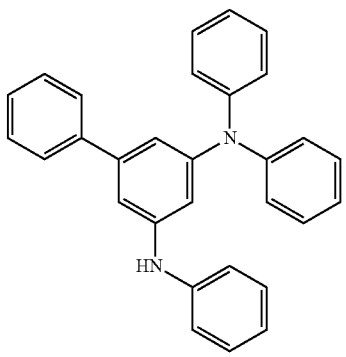
Sub 2-18
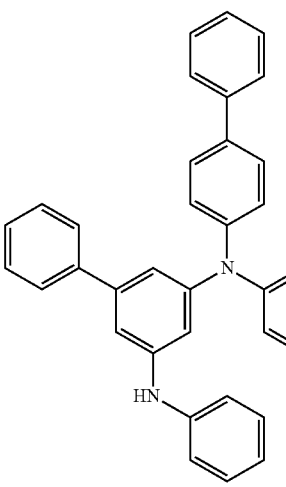
Sub 2-19
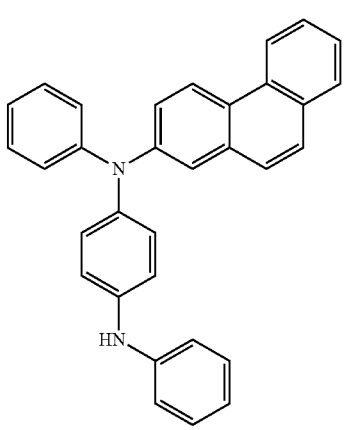

-continued
Sub 2-20
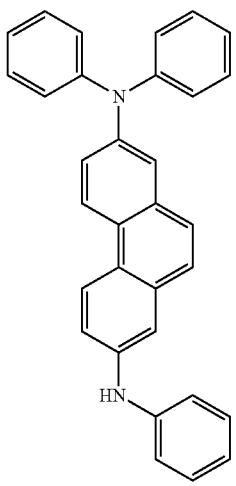
Sub 2-21
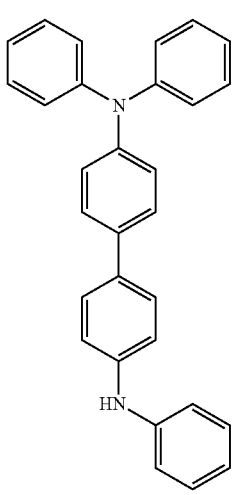
Sub 2-22
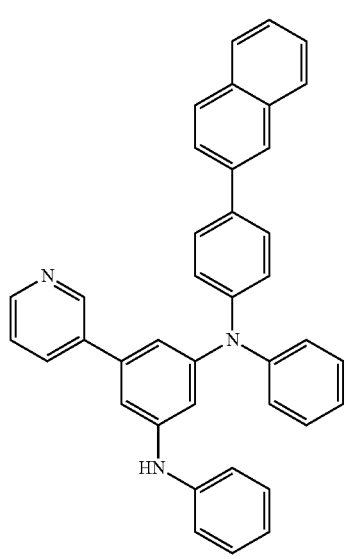
-continued
Sub 2-23
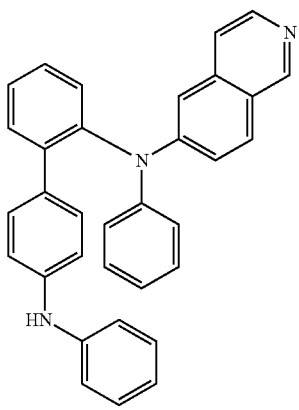
Sub 2-24
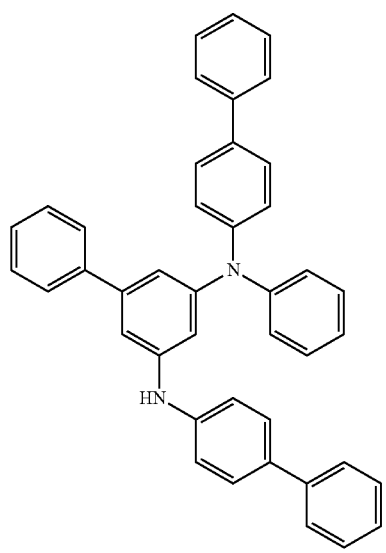
Sub 2-25
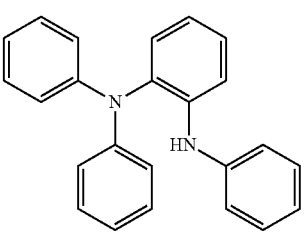
Sub 2-26
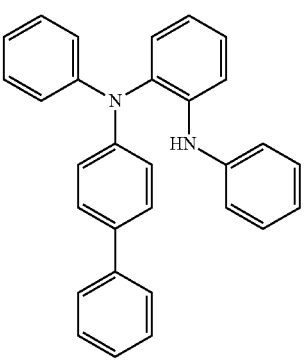

Sub 2-27
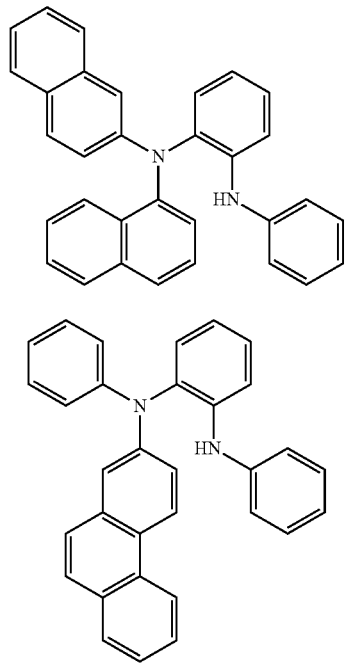
Sub 2-28
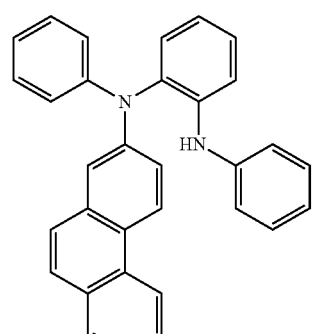
Sub 2-29
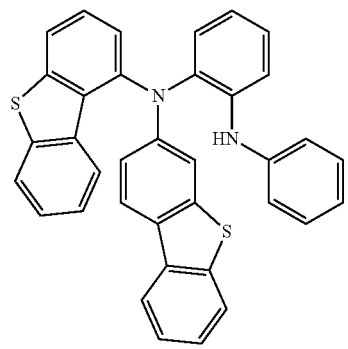
Sub 2-30
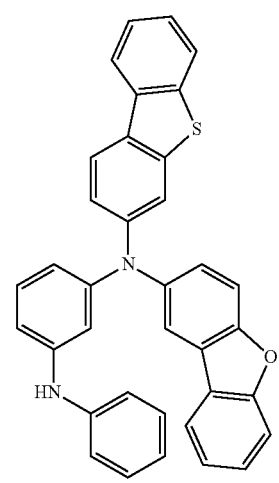
Sub 2-31
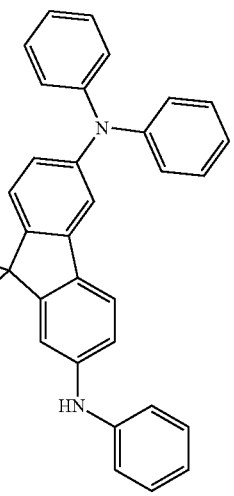
Sub 2-32
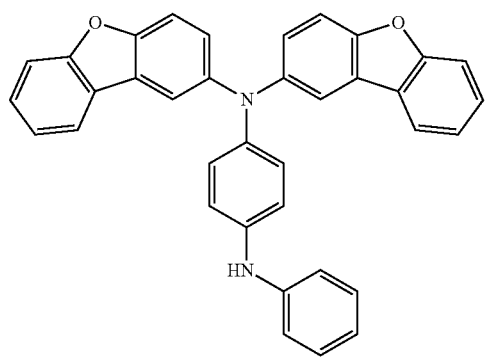
Sub 2-33
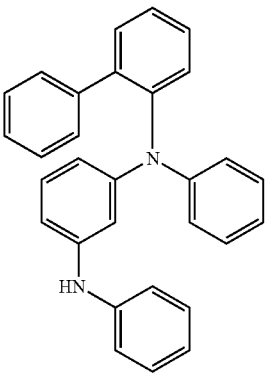

Sub 2-34
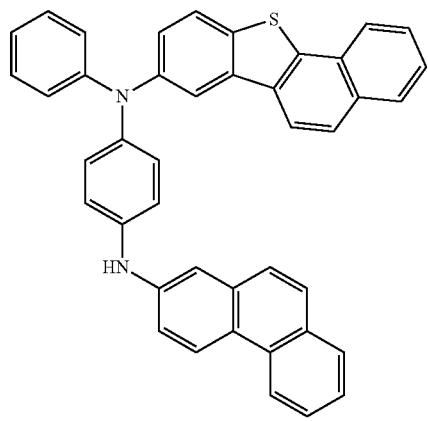
Sub 2-37
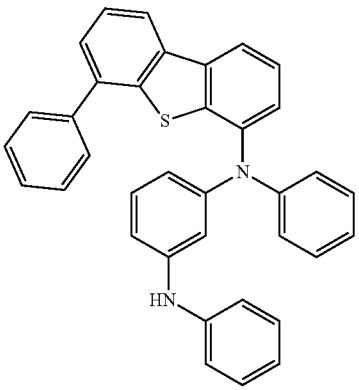
Sub 2-35
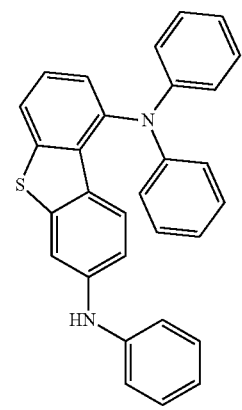
Sub 2-38
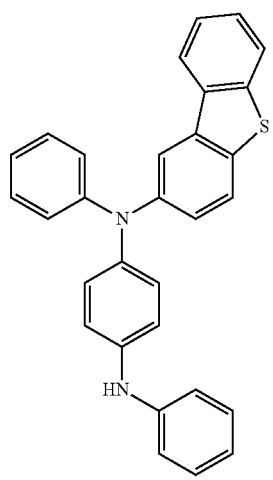
Sub 2-36
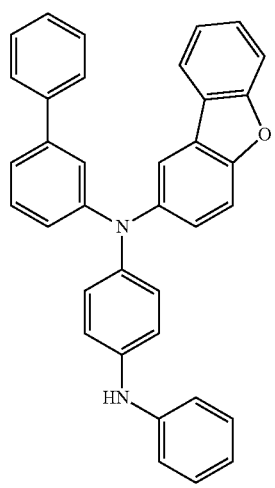
Sub 2-39
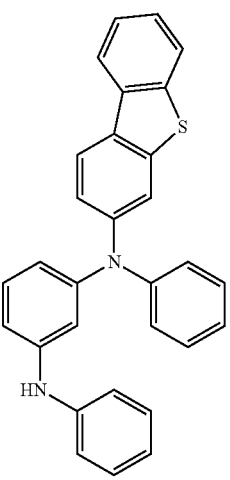

Sub 2-40
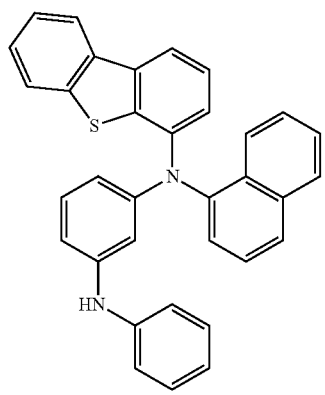
Sub 2-41
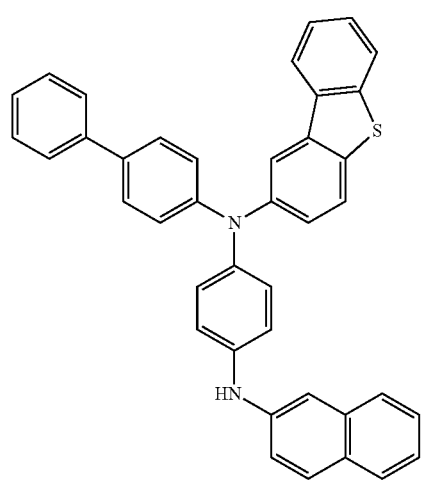
Sub 2-42
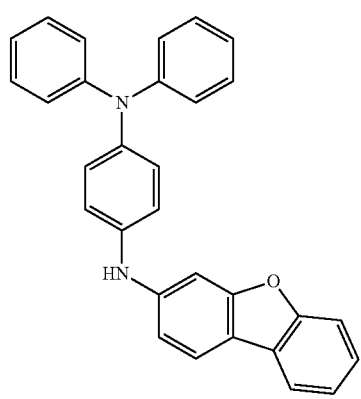
Sub 2-43
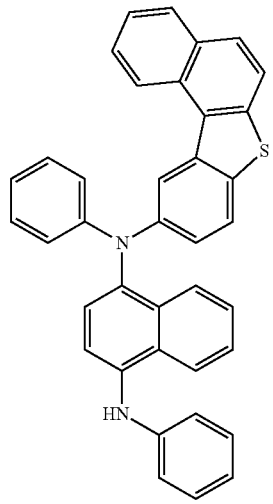
Sub 2-44
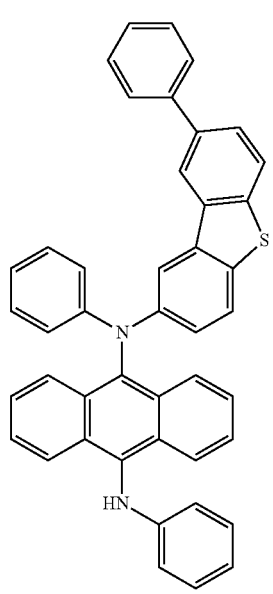
Sub 2-45
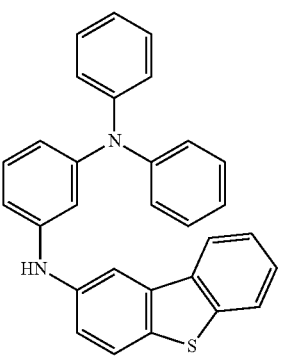

Sub 2-46
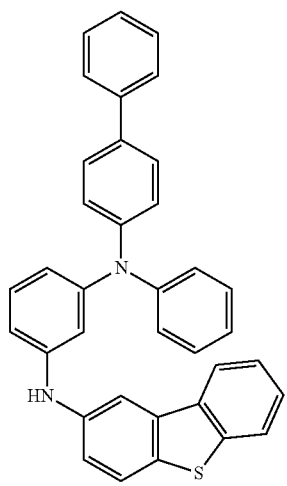
Sub 2-47
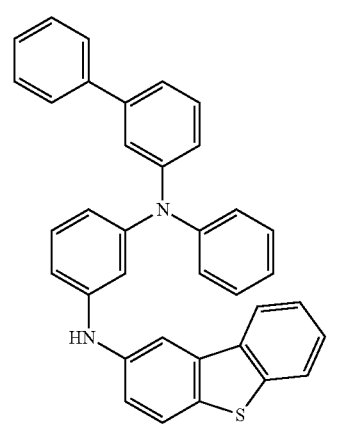
Sub 2-48
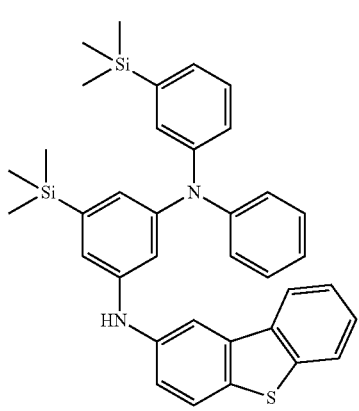
Sub 2-49
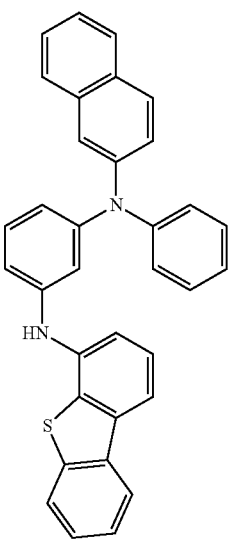
Sub 2-50
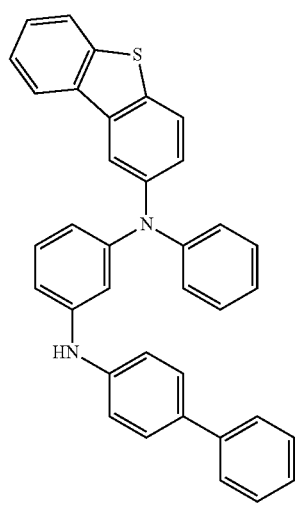
Sub 2-51
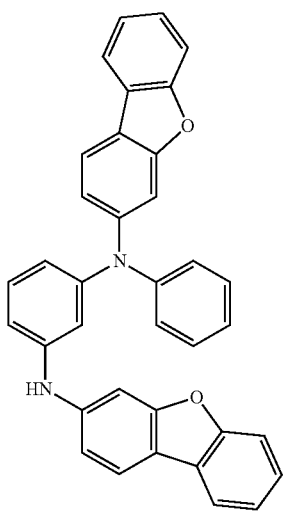

Sub 2-52
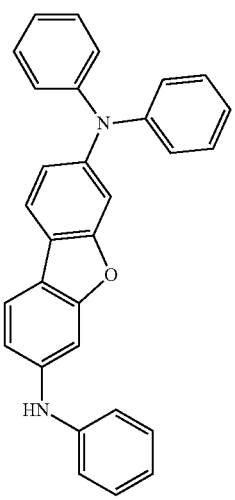
Sub 2-53
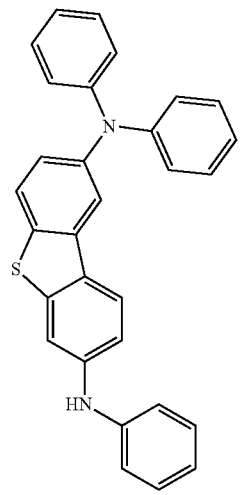
Sub 2-54
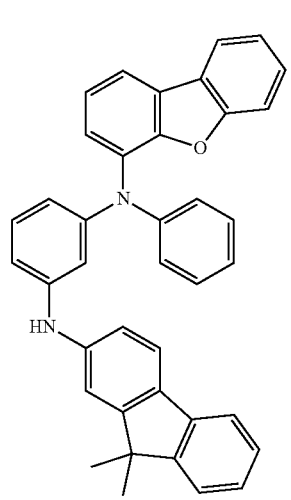
Sub 2-55
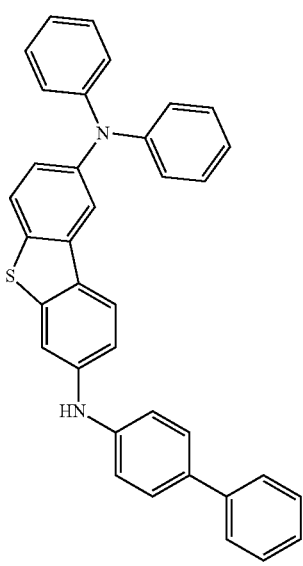
Sub 2-56
Sub 2-57
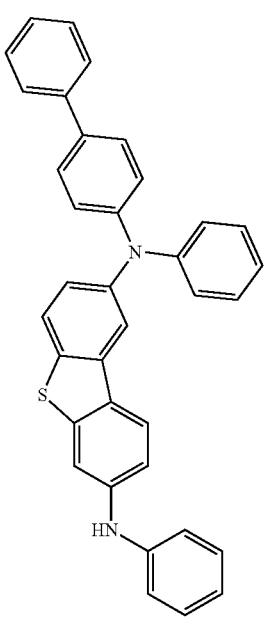

Sub 2-58
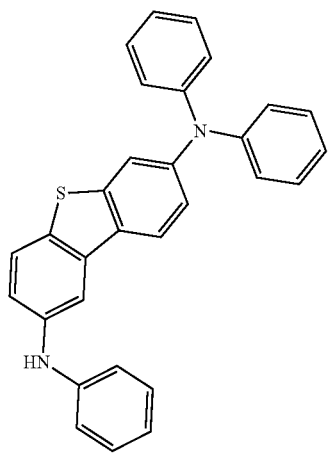
Sub 2-61
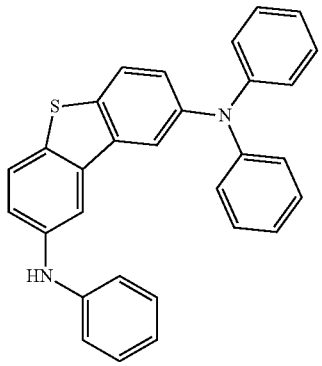
Sub 2-59
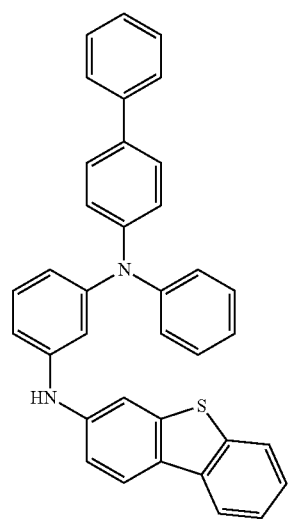
Sub 2-62
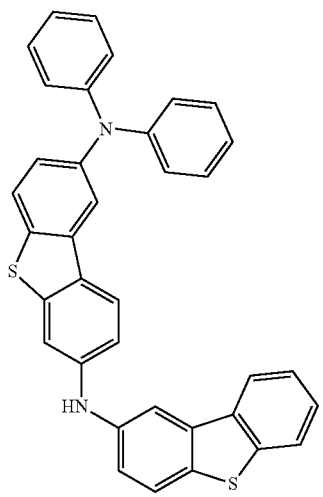
Sub 2-60
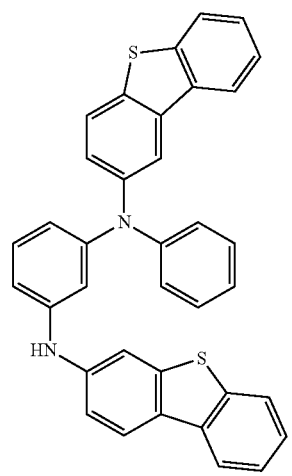
Sub 2-63
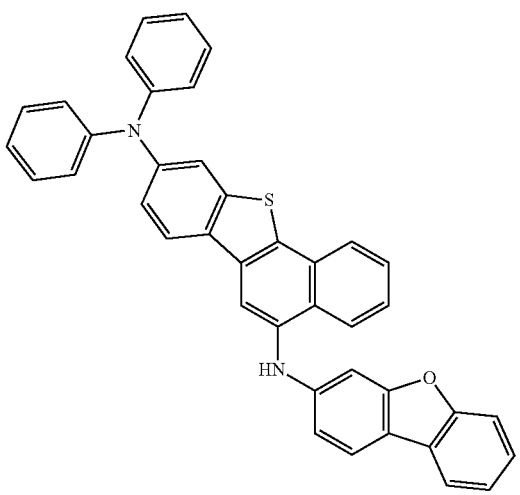

Sub 2-64
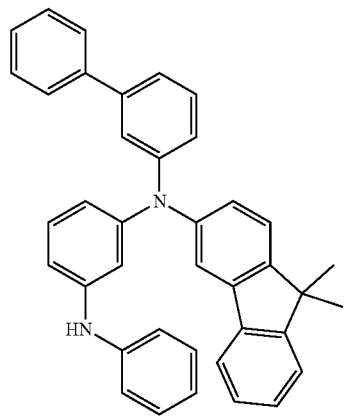
Sub 2-65
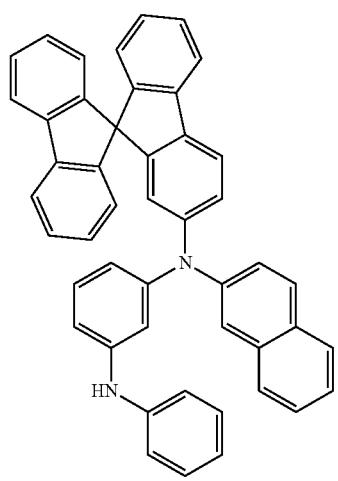
Sub 2-66
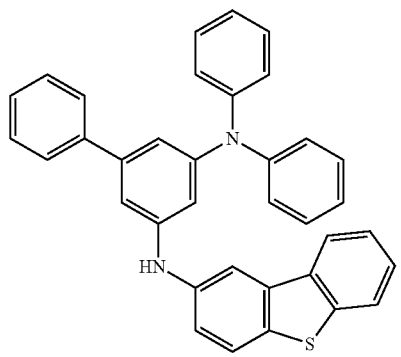
Sub 2-67
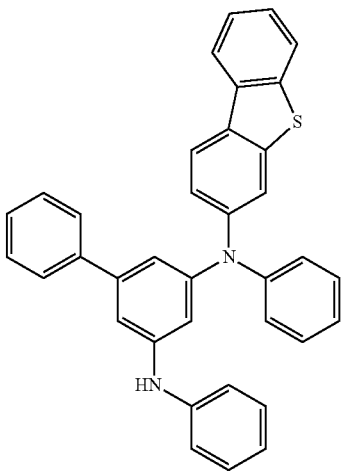
Sub 2-68
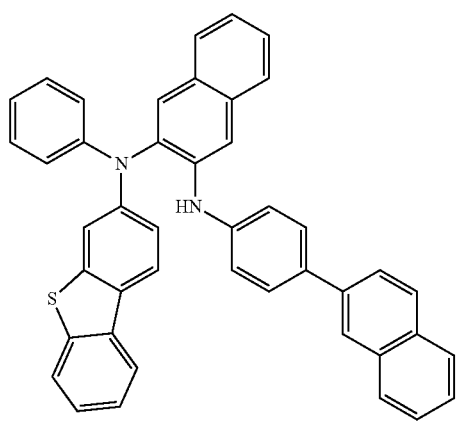
Sub 2-69
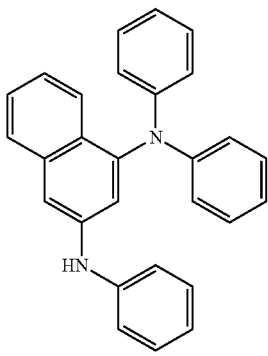

Sub 2-70
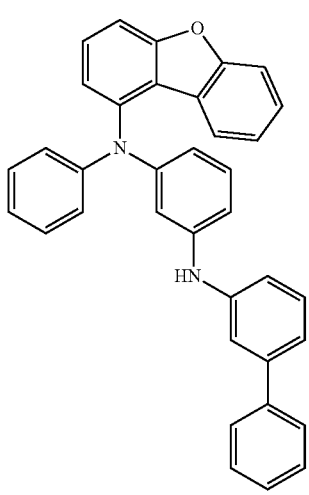
Sub 2-73
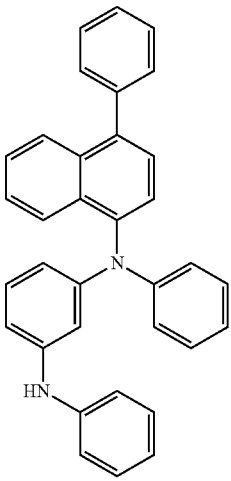
Sub 2-71
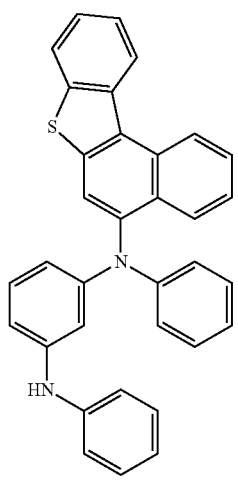
Sub 2-74
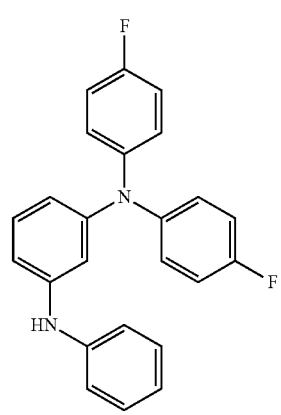
Sub 2-72
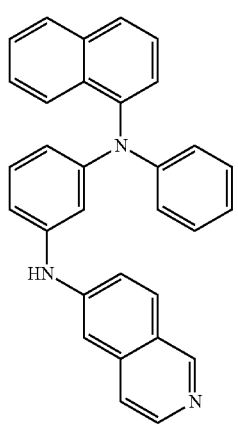
Sub 2-75
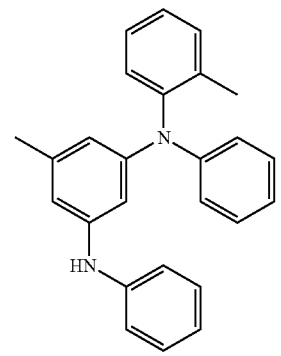

Sub 2-76
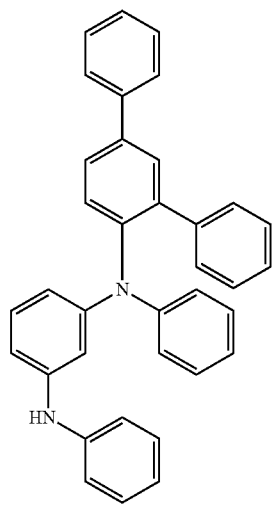
Sub 2-77
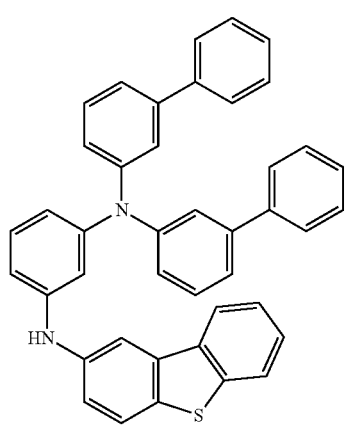
Sub 2-78
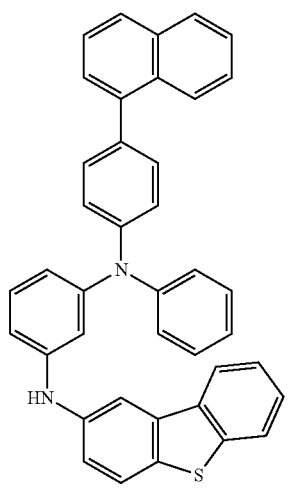
Sub 2-79
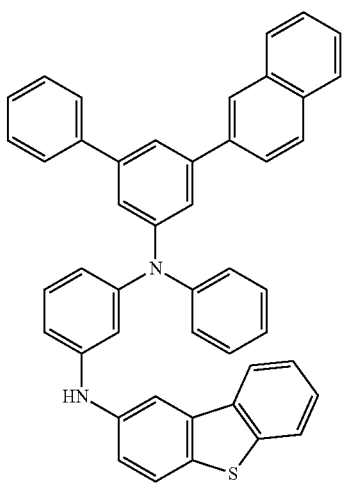
Sub 2-80
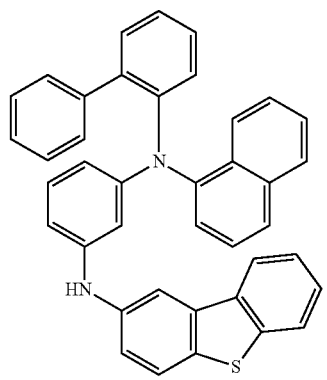
Sub 2-81
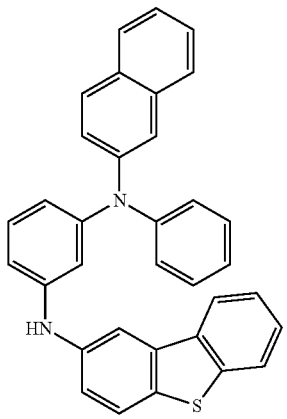

Sub 2-82
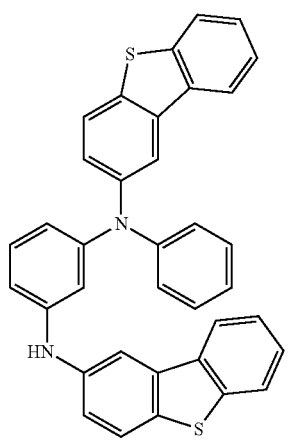
Sub 2-85
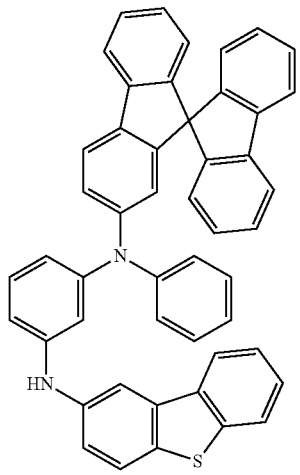
Sub 2-83
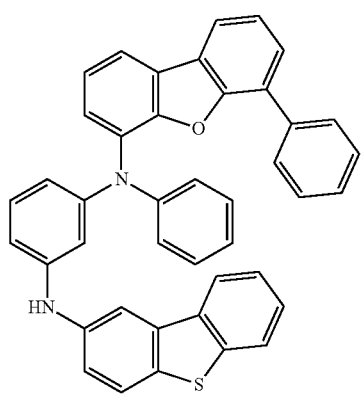
Sub 2-86
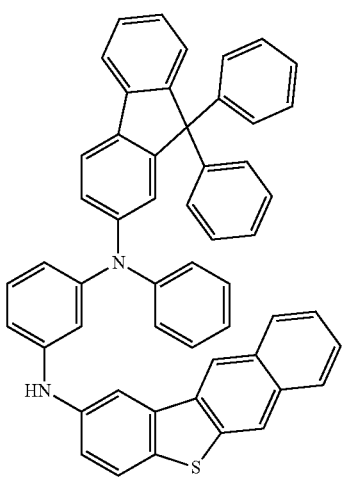
Sub 2-84
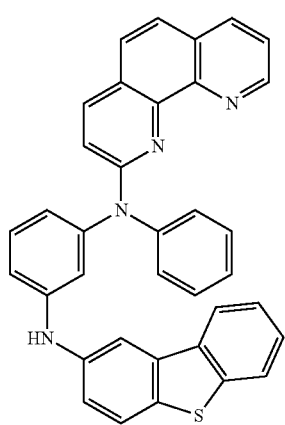
Sub 2-87
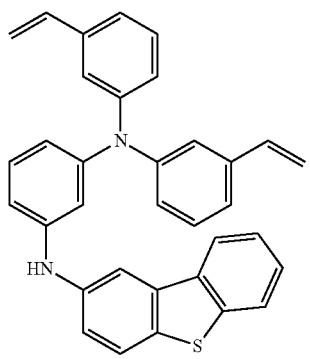

Sub 2-88
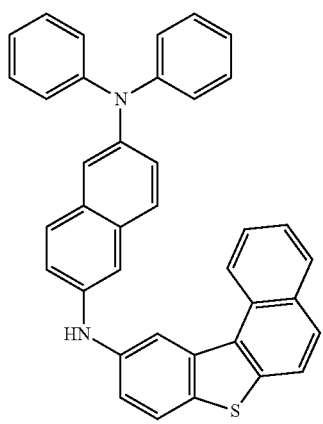
Sub 2-89
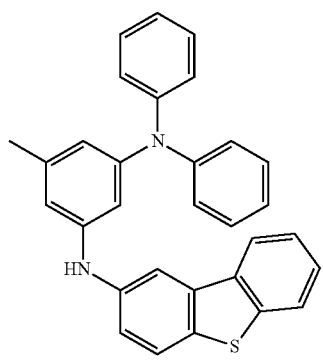
Sub 2-90
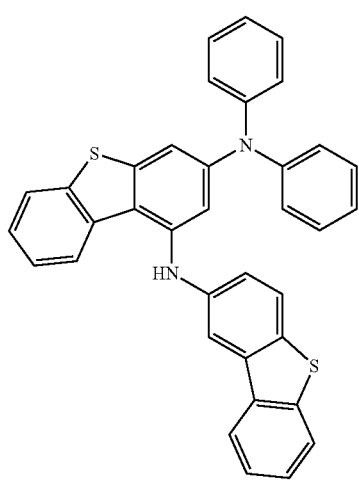
Sub 2-91
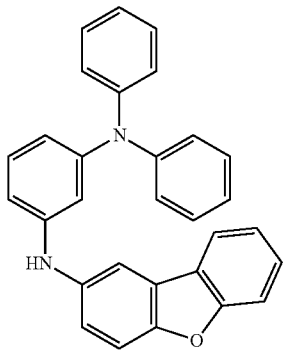
Sub 2-92
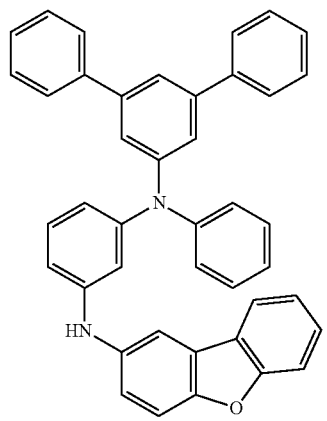
Sub 2-93
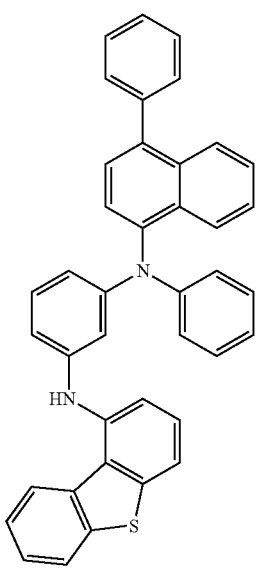

Sub 2-94

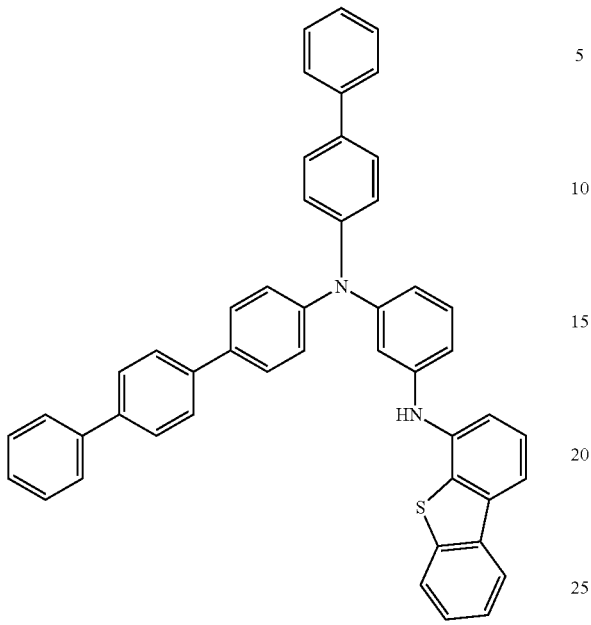

TABLE 2

| Compound | FD-MS | Compound | FD-MS |
|---|---|---|---|
| Sub 2-1 | m/z = 336.16($C_{24}H_{20}N_2$ = 336.44) | Sub 2-2 | m/z = 412.19($C_{30}H_{24}N_2$ = 412.54) |
| Sub 2-3 | m/z = 488.23($C_{36}H_{28}N_2$ = 488.63) | Sub 2-4 | m/z = 336.16($C_{24}H_{20}N_2$ = 336.44) |
| Sub 2-5 | m/z = 413.19($C_{39}H_{23}N_3$ = 413.52) | Sub 2-6 | m/z = 442.15($C_{30}H_{22}N_2S$ = 442.58) |
| Sub 2-7 | m/z = 462.21($C_{34}H_{26}N_2$ = 462.60) | Sub 2-8 | m/z = 488.23($C_{36}H_{28}N_2$ = 488.63) |
| Sub 2-9 | m/z = 488.23($C_{36}H_{28}N_2$ = 488.63) | Sub 2-10 | m/z = 412.19($C_{30}H_{24}N_2$ = 412.54) |
| Sub 2-11 | m/z = 488.23($C_{36}H_{28}N_2$ = 488.63) | Sub 2-12 | m/z = 488.23($C_{36}H_{28}N_2$ = 488.63) |
| Sub 2-13 | m/z = 488.23($C_{36}H_{28}N_2$ = 488.63) | Sub 2-14 | m/z = 417.23($C_{30}H_{19}D_5N_2$ = 417.57) |
| Sub 2-15 | m/z = 462.21($C_{34}H_{26}N_2$ = 462.60) | Sub 2-16 | m/z = 462.21($C_{34}H_{26}N_2$ = 462.60) |
| Sub 2-17 | m/z = 412.19($C_{30}H_{24}N_2$ = 412.54) | Sub 2-18 | m/z = 564.26($C_{42}H_{32}N_2$ = 564.73) |
| Sub 2-19 | m/z = 436.19($C_{32}H_{24}N_2$ = 436.56) | Sub 2-20 | m/z = 436.19($C_{32}H_{24}N_2$ = 436.56) |
| Sub 2-21 | m/z = 412.19($C_{30}H_{24}N_2$ = 412.54) | Sub 2-22 | m/z = 539.24($C_{39}H_{29}N_3$ = 539.68) |
| Sub 2-23 | m/z = 463.20($C_{33}H_{25}N_3$ = 463.58) | Sub 2-24 | m/z = 564.26($C_{42}H_{32}N_2$ = 564.73) |
| Sub 2-25 | m/z = 336.16($C_{24}H_{20}N_2$ = 336.44) | Sub 2-26 | m/z = 412.19($C_{30}H_{24}N_2$ = 412.54) |
| Sub 2-27 | m/z = 436.19($C_{32}H_{24}N_2$ = 436.56) | Sub 2-28 | m/z = 436.19($C_{32}H_{24}N_2$ = 436.56) |
| Sub 2-29 | m/z = 548.14($C_{36}H_{24}N_2S_2$ = 548.72) | Sub 2-30 | m/z = 532.16($C_{36}H_{24}N_2SO$ = 532.66) |
| Sub 2-31 | m/z = 452.23($C_{33}H_{28}N_2$ = 452.60) | Sub 2-32 | m/z = 516.18($C_{36}H_{24}N_2O_2$ = 516.60) |
| Sub 2-33 | m/z = 412.19($C_{30}H_{24}N_2$ = 412.54) | Sub 2-34 | m/z = 592.20($C_{42}H_{28}N_2S$ = 592.76) |
| Sub 2-35 | m/z = 442.15($C_{30}H_{22}N_2S$ = 442.58) | Sub 2-36 | m/z = 502.20($C_{36}H_{26}N_2O$ = 502.62) |
| Sub 2-37 | m/z = 518.18($C_{36}H_{26}N_2S$ = 518.68) | Sub 2-38 | m/z = 442.15($C_{30}H_{22}N_2S$ = 442.58) |
| Sub 2-39 | m/z = 442.15($C_{30}H_{22}N_2S$ = 442.58) | Sub 2-40 | m/z = 492.17($C_{34}H_{24}N_2S$ = 492.64) |
| Sub 2-41 | m/z = 568.20($C_{40}H_{28}N_2S$ = 568.74) | Sub 2-42 | m/z = 426.17($C_{30}H_{22}N_2O$ = 426.52) |
| Sub 2-43 | m/z = 542.18($C_{38}H_{26}N_2S$ = 542.70) | Sub 2-44 | m/z = 618.21($C_{44}H_{30}N_2S$ = 618.80) |
| Sub 2-45 | m/z = 442.15($C_{30}H_{22}N_2S$ = 442.58) | Sub 2-46 | m/z = 518.18($C_{36}H_{26}N_2S$ = 518.68) |
| Sub 2-47 | m/z = 518.18($C_{36}H_{26}N_2S$ = 518.68) | Sub 2-48 | m/z = 586.23($C_{36}H_{38}N_2SSi_2$ = 586.94) |
| Sub 2-49 | m/z = 492.17($C_{34}H_{24}N_2S$ = 492.64) | Sub 2-50 | m/z = 518.18($C_{36}H_{26}N_2S$ = 518.68) |
| Sub 2-51 | m/z = 516.18($C_{36}H_{24}N_2O_2$ = 516.60) | Sub 2-52 | m/z = 426.17($C_{30}H_{22}N_2O$ = 426.52) |
| Sub 2-53 | m/z = 436.19($C_{32}H_{24}N_2$ = 436.56) | Sub 2-54 | m/z = 542.24($C_{39}H_{30}N_2O$ = 542.68) |
| Sub 2-55 | m/z = 442.15($C_{30}H_{22}N_2S$ = 442.58) | Sub 2-56 | m/z = 518.18($C_{36}H_{26}N_2S$ = 518.68) |
| Sub 2-57 | m/z = 518.18($C_{36}H_{26}N_2S$ = 518.68) | Sub 2-58 | m/z = 442.15($C_{30}H_{22}N_2S$ = 442.58) |
| Sub 2-59 | m/z = 518.18($C_{36}H_{26}N_2S$ = 518.68) | Sub 2-60 | m/z = 548.14($C_{36}H_{24}N_2S_2$ = 548.72) |
| Sub 2-61 | m/z = 442.15($C_{30}H_{22}N_2S$ = 442.58) | Sub 2-62 | m/z = 548.14($C_{36}H_{24}N_2S_2$ = 548.72) |
| Sub 2-63 | m/z = 582.18($C_{40}H_{26}N_2OS$ = 582.72) | Sub 2-64 | m/z = 528.26($C_{39}H_{32}N_2$ = 528.70) |
| Sub 2-65 | m/z = 624.26($C_{47}H_{32}N_2$ = 624.79) | Sub 2-66 | m/z = 518.18($C_{36}H_{26}N_2S$ = 518.68) |
| Sub 2-67 | m/z = 518.18($C_{36}H_{26}N_2S$ = 518.68) | Sub 2-68 | m/z = 618.21($C_{44}H_{30}N_2S$ = 618.80) |
| Sub 2-69 | m/z = 386.18($C_{28}H_{22}N_2$ = 386.50) | Sub 2-70 | m/z = 502.20($C_{36}H_{26}N_2O$ = 502.62) |
| Sub 2-71 | m/z = 492.17($C_{34}H_{24}N_2S$ = 492.64) | Sub 2-72 | m/z = 437.19($C_{31}H_{23}N_3$ = 437.55) |
| Sub 2-73 | m/z = 462.21($C_{34}H_{28}N_2$ = 462.60) | Sub 2-74 | m/z = 372.14($C_{24}H_{18}F_2N_2$ = 372.42) |
| Sub 2-75 | m/z = 364.19($C_{26}H_{24}N_2$ = 364.49) | Sub 2-76 | m/z = 488.23($C_{36}H_{28}N_2$ = 488.63) |
| Sub 2-77 | m/z = 594.21($C_{42}H_{30}N_2S$ = 594.78) | Sub 2-78 | m/z = 568.20($C_{40}H_{28}N_2S$ = 568.74) |
| Sub 2-79 | m/z = 644.23($C_{46}H_{32}N_2S$ = 644.84) | Sub 2-80 | m/z = 568.20($C_{40}H_{28}N_2S$ = 568.74) |
| Sub 2-81 | m/z = 492.17($C_{34}H_{24}N_2S$ = 492.64) | Sub 2-82 | m/z = 548.14($C_{36}H_{24}N_2S_2$ = 548.72) |
| Sub 2-83 | m/z = 608.19($C_{42}H_{28}N_2SO$ = 608.76) | Sub 2-84 | m/z = 544.17($C_{36}H_{24}N_4$ = 544.68) |

TABLE 2-continued

| Compound | FD-MS | Compound | FD-MS |
|---|---|---|---|
| Sub 2-85 | m/z = 680.23($C_{49}H_{32}N_2S$ = 680.87) | Sub 2-86 | m/z = 732.26($C_{53}H_{36}N_2S$ = 732.95) |
| Sub 2-87 | m/z = 494.18($C_{34}H_{26}N_2S$ = 494.66) | Sub 2-88 | m/z = 542.18($C_{38}H_{26}N_2S$ = 542.70) |
| Sub 2-89 | m/z = 456.17($C_{31}H_{24}N_2S$ = 456.61) | Sub 2-90 | m/z = 548.14($C_{36}H_{24}N_2S_2$ = 548.72) |
| Sub 2-91 | m/z = 426.17($C_{30}H_{22}N_2O$ = 426.52) | Sub 2-92 | m/z = 578.24($C_{42}H_{30}N_2O$ = 578.72) |
| Sub 2-93 | m/z = 568.20($C_{40}H_{28}N_2S$ = 568.74) | Sub 2-94 | m/z = 670.24($C_{48}H_{34}N_2S$ = 670.87) |

II. Synthesis of Product

After Sub 1 (1 eq.) was dissolved in toluene in a round bottom flask, Sub 2 (1 eq.), Pd$_2$(dba)$_3$ (0.03 eq.), (t-Bu)$_3$P (0.06 eq.), NaOt-Bu (3 eq.) were added to the solution and the mixture was stirred at 120° C. for 3 h. When the reaction was completed, the reaction product was extracted with CH$_2$Cl$_2$ and water, and then the organic layer was dried with MgSO$_4$ and concentrated. Then, the concentrate was applied to silica gel column and recrystallized to obtain a final product.

1. Synthesis Example of P-2

<Reaction Scheme 18>

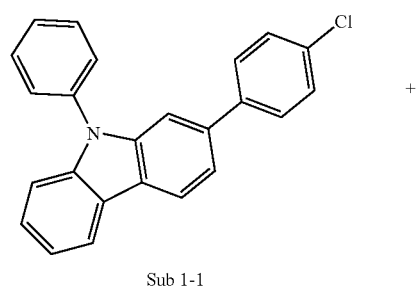

Sub 1-1

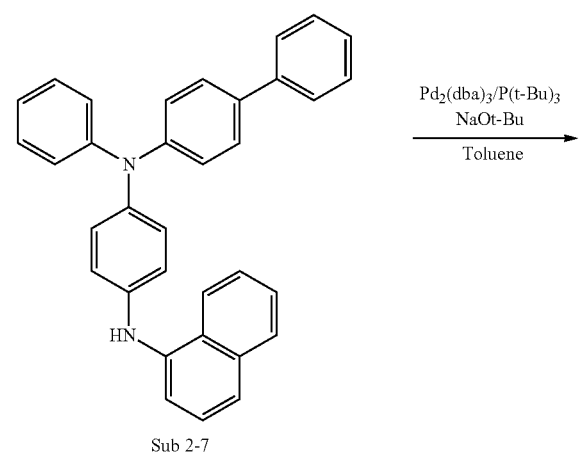

Sub 2-7

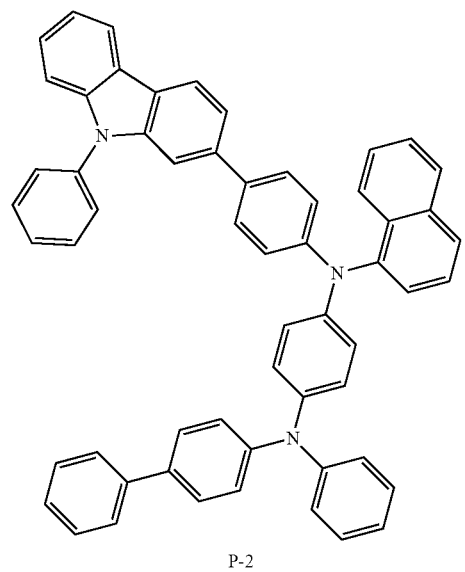

P-2

After Sub 1-1 (10 g, 28.26 mmol) obtained in the above synthesis was dissolved in toluene (90 ml) in a round bottom flask, Sub 2-7 (13.07 g, 28.26 mmol), Pd$_2$(dba)$_3$ (0.98 g, 0.85 mmol), 50% P(t-Bu)$_3$ (0.68 ml, 1.69 mmol), NaOt-Bu (8.15 g, 84.78 mmol) were added to the solution and the mixture was stirred at 120° C. When the reaction was completed, the reaction product was extracted with CH$_2$Cl$_2$ and water, and then the organic layer was dried with MgSO$_4$ and concentrated. Then, the concentrate was applied to silica gel column and recrystallized to obtain 20 g (yield: 92%) of the product.

2. Synthesis Example of P-14

<Reaction Scheme 19>

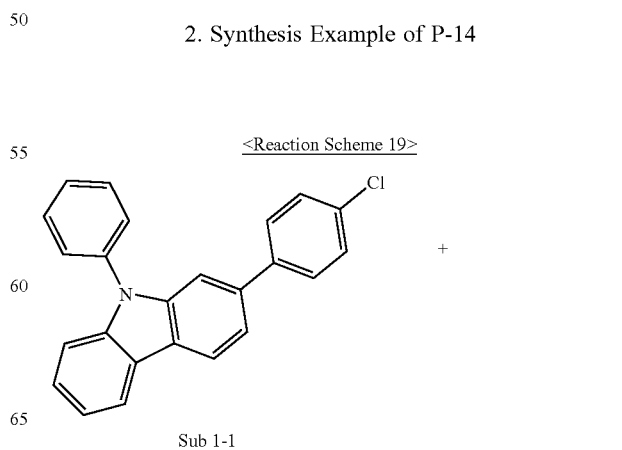

Sub 1-1

125
-continued

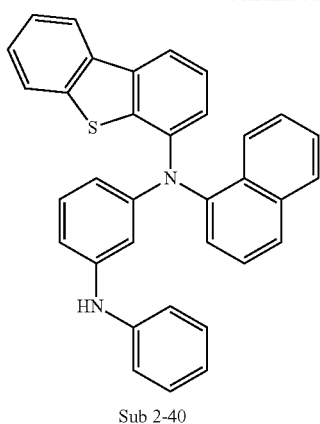

Sub 2-40

Pd₂(dba)₃/P(t-Bu)₃
NaOt-Bu
Toluene →

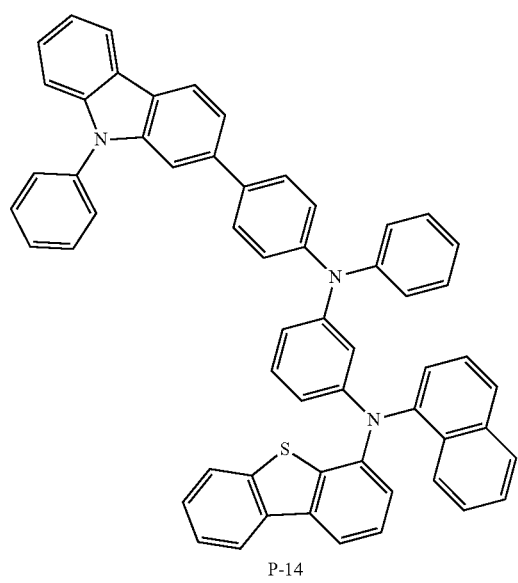

P-14

After Sub 2-40 (13.92 g, 28.26 mmol), Pd₂(dba)₃ (0.98 g, 0.85 mmol), 50% P(t-Bu)₃ (0.68 ml, 1.69 mmol), NaOt-Bu (8.15 g, 84.78 mmol), toluene (90 ml) were added to Sub 1-1 (10 g, 28.26 mmol) obtained in the above synthesis, 19.5 g (yield: 85%) of the product was obtained by proceeding with the same method as in synthesis of P-2.

3. Synthesis Example of P-32

<Reaction Scheme 20>

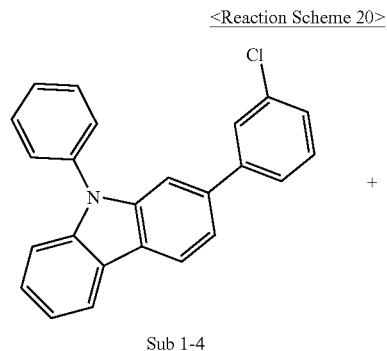

Sub 1-4

126
-continued

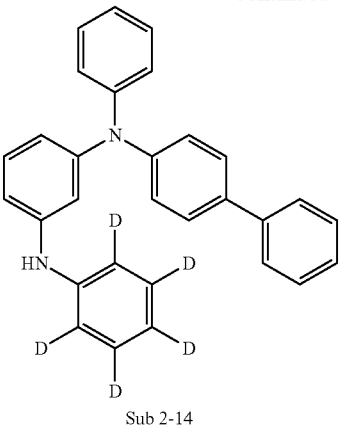

Sub 2-14

Pd₂(dba)₃/P(t-Bu)₃
NaOt-Bu
Toluene →

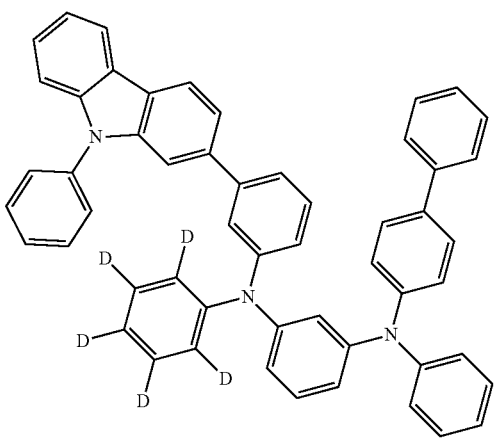

P-32

After Sub 2-14 (11.8 g, 28.26 mmol), Pd₂(dba)₃ (0.98 g, 0.85 mmol), 50% P(t-Bu)₃ (0.68 ml, 1.69 mmol), NaOt-Bu (8.15 g, 84.78 mmol), toluene (90 ml) were added to Sub 1-4 (10 g, 28.26 mmol) obtained in the above synthesis, 20 g (yield: 96%) of the product was obtained by proceeding with the same method as in synthesis of P-2.

4. Synthesis Example of P-46

<Reaction Scheme 21>

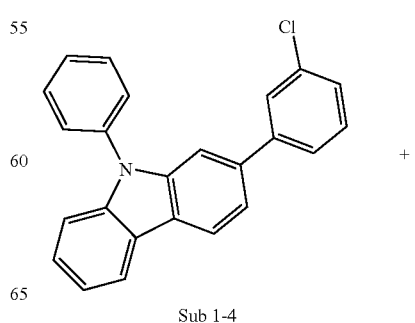

Sub 1-4

+

+

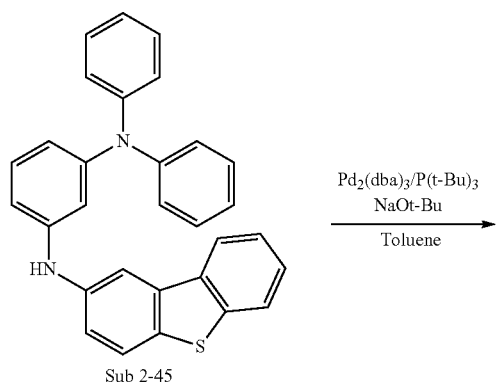

Sub 2-45

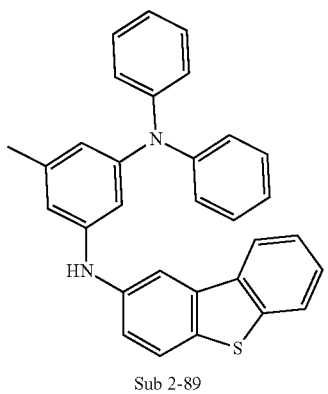

Sub 2-89

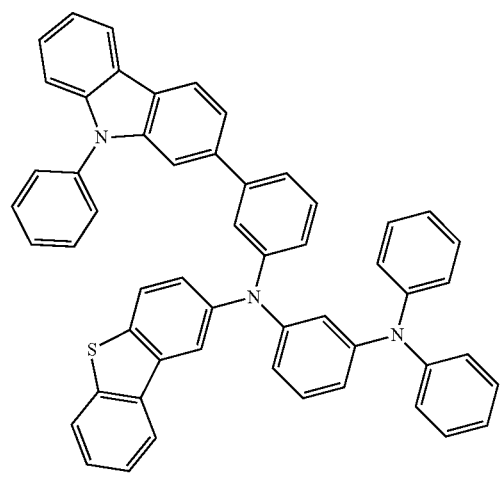

P-46

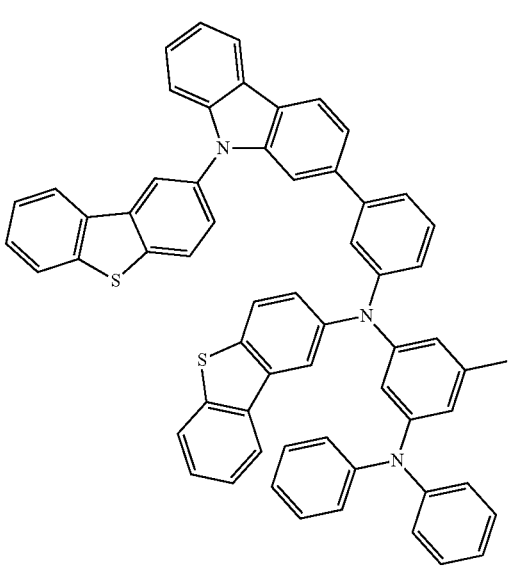

P-60

After Sub 2-45 (12.5 g, 28.26 mmol), Pd₂(dba)₃ (0.98 g, 0.85 mmol), 50% P(t-Bu)₃ (0.68 ml, 1.69 mmol), NaOt-Bu (8.15 g, 84.78 mmol), toluene (90 ml) were added to Sub 1-4 (10 g, 28.26 mmol) obtained in the above synthesis, 18 g (yield: 84%) of the product was obtained by proceeding with the same method as in synthesis of P-2.

5. Synthesis Example of P-60

After Sub 2-89 (8 g, 17.39 mmol), Pd₂(dba)₃ (0.5 g, 0.52 mmol), 50% P(t-Bu)₃ (0.42 ml, 1.04 mmol), NaOt-Bu (5 g, 52.18 mmol), toluene (60 ml) were added to Sub 1-29 (8 g, 17.39 mmol) obtained in the above synthesis, 12 g (yield: 78%) of the product was obtained by proceeding with the same method as in synthesis of P-2.

6. Synthesis Example of P-68

<Reaction Scheme 22>

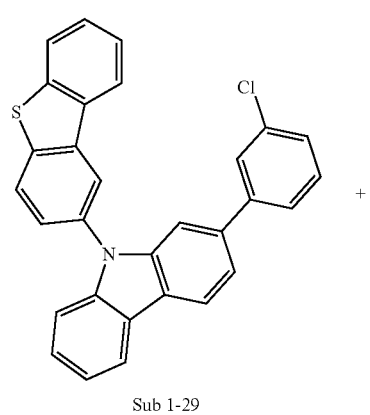

Sub 1-29

+

<Reaction Scheme 23>

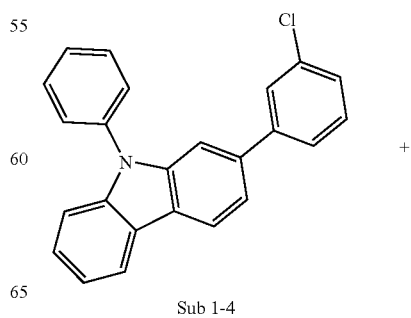

Sub 1-4

+

-continued

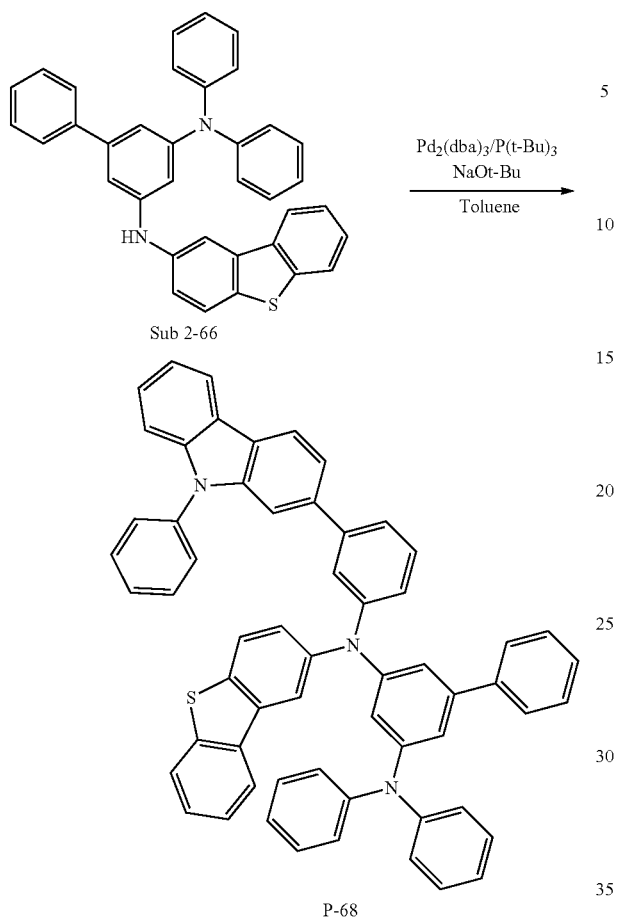

After Sub 2-66 (14.7 g, 28.26 mmol), Pd$_2$(dba)$_3$ (0.98 g, 0.85 mmol), 50% P(t-Bu)$_3$ (0.68 ml, 1.69 mmol), NaOt-Bu (8.15 g, 84.78 mmol), toluene (90 ml) were added to Sub 1-4 (10 g, 28.26 mmol) obtained in the above synthesis, 21 g (yield: 89%) of the product was obtained by proceeding with the same method as in synthesis of P-2.

7. Synthesis Example of P-79

<Reaction Scheme 24>

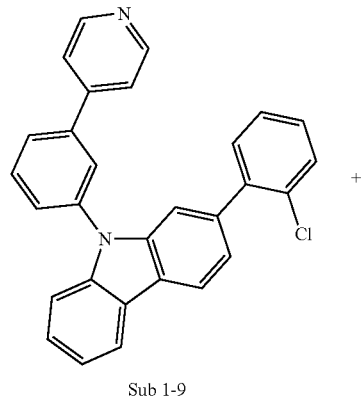

-continued

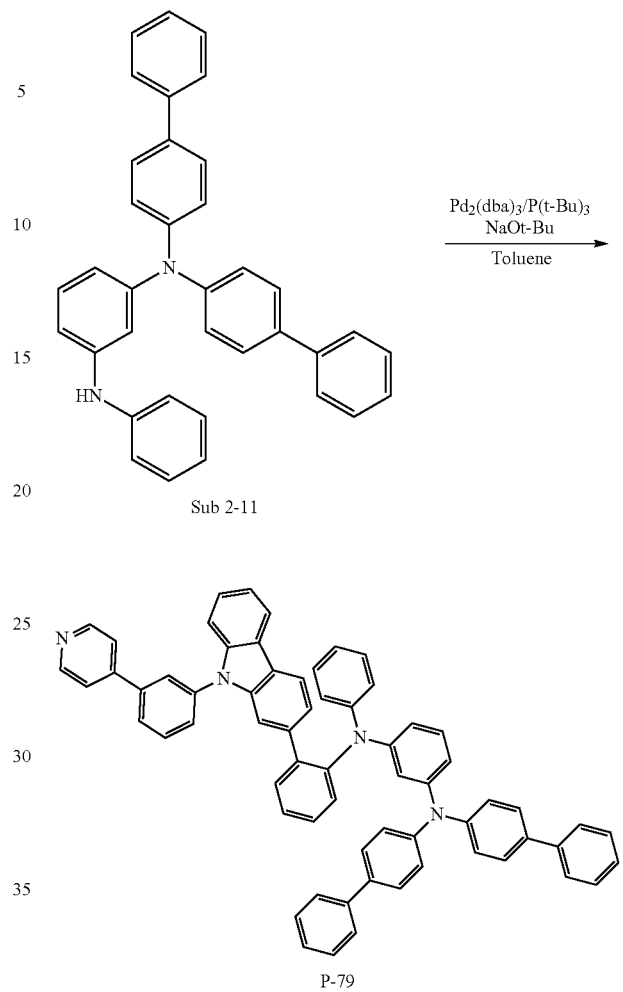

After Sub 2-11 (28.3 g, 58.01 mmol), Pd$_2$(dba)$_3$ (2 g, 1.74 mmol), 50% P(t-Bu)$_3$ (1.4 ml, 3.48 mmol), NaOt-Bu (16.7 g, 174 mmol), toluene (190 ml) were added to Sub 1-9 (25 g, 58.01 mmol) obtained in the above synthesis, 46 g (yield: 90%) of the product was obtained by proceeding with the same method as in synthesis of P-2.

8. Synthesis Example of P-96

<Reaction Scheme 25>

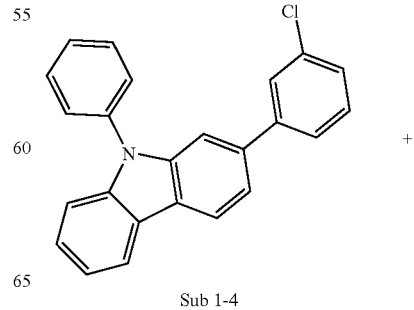

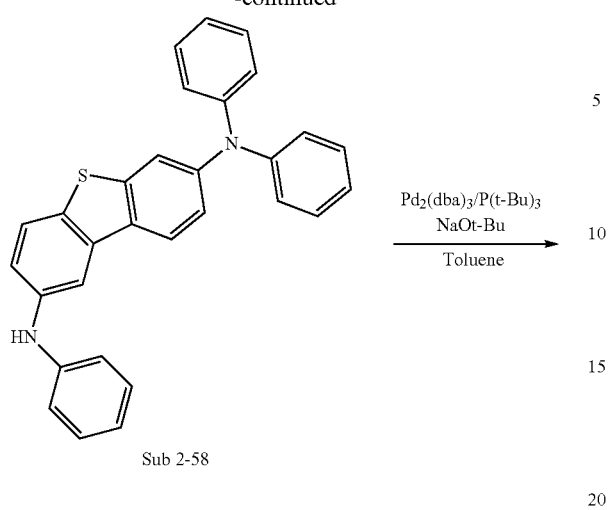

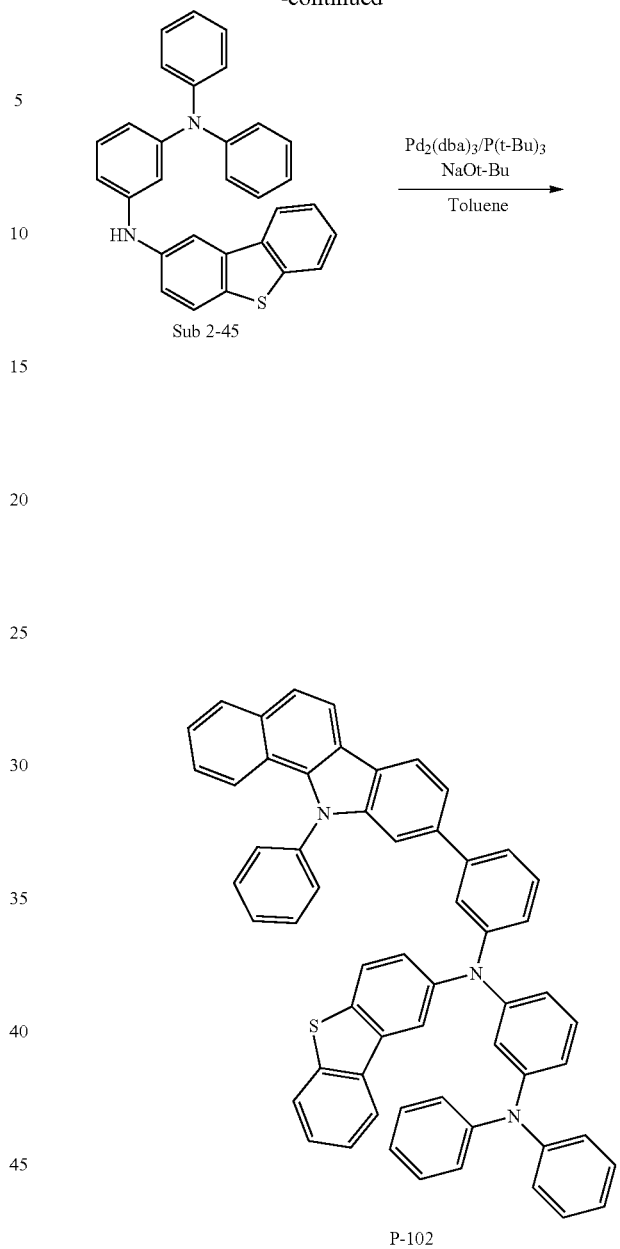

After Sub 2-58 (12.5 g, 28.26 mmol), Pd$_2$(dba)$_3$ (0.98 g, 0.85 mmol), 50% P(t-Bu)$_3$ (0.68 ml, 1.69 mmol), NaOt-Bu (8.15 g, 84.78 mmol), toluene (90 ml) were added to Sub 1-4 (10 g, 28.26 mmol) obtained in the above synthesis, 19 g (yield: 89%) of the product was obtained by proceeding with the same method as in synthesis of P-2.

9. Synthesis Example of P-102

<Reaction Scheme 26>

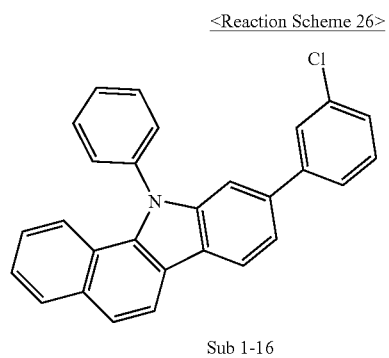

After Sub 2-45 (7.7 g, 17.33 mmol), Pd$_2$(dba)$_3$ (0.5 g, 0.52 mmol), 50% P(t-Bu)$_3$ (0.42 ml, 1.04 mmol), NaOt-Bu (5 g, 51.99 mmol), toluene (60 ml) were added to Sub 1-16 (7 g, 17.33 mmol) obtained in the above synthesis, 10 g (yield: 72%) of the product was obtained by proceeding with the same method as in synthesis of P-2.

The FD-MS values of the compounds of the present invention prepared according to the above synthesis examples are shown in Table 3 below.

TABLE 3

| Compound | FD-MS | Compound | FD-MS |
|---|---|---|---|
| P-1 | m/z = 653.28($C_{48}H_{35}N_3$ = 653.83) | P-2 | m/z = 779.33($C_{58}H_{41}N_3$ = 779.99) |
| P-3 | m/z = 805.35($C_{60}H_{43}N_3$ = 806.03) | P-4 | m/z = 779.33($C_{58}H_{41}N_3$ = 779.99) |
| P-5 | m/z = 885.32($C_{64}H_{43}N_3S$ = 886.13) | P-6 | m/z = 759.27($C_{54}H_{37}N_3S$ = 759.97) |
| P-7 | m/z = 833.30($C_{60}H_{39}N_3O_2$ = 833.99) | P-8 | m/z = 869.34($C_{64}H_{43}N_3O$ = 870.07) |
| P-9 | m/z = 653.28($C_{48}H_{35}N_3$ = 653.83) | P-10 | m/z = 805.35($C_{60}H_{43}N_3$ = 806.03) |
| P-11 | m/z = 835.30($C_{60}H_{41}N_3S$ = 836.07) | P-12 | m/z = 961.35($C_{70}H_{47}N_3S$ = 962.23) |
| P-13 | m/z = 809.29($C_{58}H_{39}N_3S$ = 810.03) | P-14 | m/z = 809.29($C_{58}H_{39}N_3S$ = 810.03) |
| P-15 | m/z = 730.31($C_{53}H_{38}N_4$ = 730.92) | P-16 | m/z = 653.28($C_{48}H_{35}N_3$ = 653.83) |
| P-17 | m/z = 729.31($C_{54}H_{39}N_3$ = 729.93) | P-18 | m/z = 753.31($C_{56}H_{39}N_3$ = 753.95) |
| P-19 | m/z = 865.26($C_{60}H_{39}N_3S_2$ = 866.11) | P-20 | m/z = 653.28($C_{48}H_{35}N_3$ = 653.83) |
| P-21 | m/z = 729.31($C_{54}H_{39}N_3$ = 729.93) | P-22 | m/z = 805.35($C_{60}H_{43}N_3$ = 806.03) |
| P-23 | m/z = 753.31($C_{56}H_{39}N_3$ = 753.95) | P-24 | m/z = 805.35($C_{60}H_{43}N_3$ = 806.03) |
| P-25 | m/z = 743.29($C_{54}H_{37}N_3O$ = 743.91) | P-26 | m/z = 885.32($C_{64}H_{43}N_3S$ = 886.13) |
| P-27 | m/z = 909.32($C_{66}H_{43}N_3S$ = 910.15) | P-28 | m/z = 653.28($C_{48}H_{35}N_3$ = 653.83) |
| P-29 | m/z = 729.31($C_{54}H_{39}N_3$ = 729.93) | P-30 | m/z = 805.35($C_{60}H_{43}N_3$ = 806.03) |
| P-31 | m/z = 779.33($C_{58}H_{41}N_3$ = 779.99) | P-32 | m/z = 734.35($C_{54}H_{34}D_5N_3$ = 734.96) |
| P-33 | m/z = 829.35($C_{62}H_{43}N_3$ = 830.05) | P-34 | m/z = 823.34($C_{60}H_{42}FN_3$ = 824.02) |
| P-35 | m/z = 765.30($C_{54}H_{37}F_2N_3$ = 765.91) | P-36 | m/z = 855.36($C_{64}H_{45}N_3$ = 856.09) |
| P-37 | m/z = 845.38($C_{63}H_{47}N_3$ = 846.09) | P-38 | m/z = 941.38($C_{71}H_{47}N_3$ = 942.18) |
| P-39 | m/z = 759.27($C_{54}H_{37}N_3S$ = 759.97) | P-40 | m/z = 835.30($C_{60}H_{41}N_3S$ = 836.07) |
| P-41 | m/z = 854.31($C_{60}H_{34}D_5N_3OS$ = 855.08) | P-42 | m/z = 909.37($C_{67}H_{47}N_3O$ = 910.13) |
| P-43 | m/z = 748.33($C_{54}H_{32}D_5N_3O$ = 748.94) | P-44 | m/z = 995.39($C_{74}H_{49}N_3O$ = 996.23) |
| P-45 | m/z = 833.30($C_{60}H_{39}N_3O_2$ = 833.99) | P-46 | m/z = 759.27($C_{54}H_{37}N_3S$ = 759.97) |
| P-47 | m/z = 835.30($C_{60}H_{41}N_3S$ = 836.07) | P-48 | m/z = 835.30($C_{60}H_{41}N_3S$ = 836.07) |
| P-49 | m/z = 885.32($C_{64}H_{43}N_3S$ = 886.13) | P-50 | m/z = 961.35($C_{70}H_{47}N_3S$ = 962.23) |
| P-51 | m/z = 935.33($C_{68}H_{45}N_3S$ = 936.19) | P-52 | m/z = 987.36($C_{72}H_{49}N_3S$ = 988.27) |
| P-53 | m/z = 885.32($C_{64}H_{43}N_3S$ = 886.13) | P-54 | m/z = 1053.40($C_{72}H_{59}N_3SSi_2$ = 1054.52) |
| P-55 | m/z = 836.30($C_{59}H_{40}N_4S$ = 837.06) | P-56 | m/z = 1049.38($C_{77}H_{51}N_3S$ = 1050.34) |
| P-57 | m/z = 997.35($C_{73}H_{47}N_3S$ = 998.26) | P-58 | m/z = 865.26($C_{60}H_{39}N_3S_2$ = 866.11) |
| P-59 | m/z = 925.31($C_{66}H_{43}N_3OS$ = 926.15) | P-60 | m/z = 879.27($C_{61}H_{41}N_3S_2$ = 880.14) |
| P-61 | m/z = 937.32($C_{66}H_{43}N_5S$ = 938.17) | P-62 | m/z = 835.30($C_{60}H_{41}N_3S$ = 836.07) |
| P-63 | m/z = 865.26($C_{60}H_{39}N_3S_2$ = 866.11) | P-64 | m/z = 987.36($C_{72}H_{49}N_3S$ = 988.27) |
| P-65 | m/z = 975.33($C_{70}H_{45}N_3OS$ = 976.21) | P-66 | m/z = 729.31($C_{54}H_{39}N_3$ = 729.93) |
| P-67 | m/z = 881.38($C_{66}H_{47}N_3$ = 882.12) | P-68 | m/z = 835.30($C_{60}H_{41}N_3S$ = 836.07) |
| P-69 | m/z = 911.33($C_{66}H_{45}N_3S$ = 912.17) | P-70 | m/z = 856.36($C_{63}H_{44}N_4$ = 857.07) |
| P-71 | m/z = 1000.36($C_{72}H_{48}N_4S$ = 1001.26) | P-72 | m/z = 881.38($C_{66}H_{47}N_3$ = 882.12) |
| P-73 | m/z = 653.28($C_{48}H_{35}N_3$ = 653.83) | P-74 | m/z = 729.31($C_{54}H_{39}N_3$ = 729.93) |
| P-75 | m/z = 935.33($C_{68}H_{45}N_3S$ 936.19) | P-76 | m/z = 905.38($C_{68}H_{47}N_3$ = 906.15) |
| P-77 | m/z = 653.28($C_{48}H_{35}N_3$ = 653.83) | P-78 | m/z = 729.31($C_{54}H_{39}N_3$ = 729.93) |
| P-79 | m/z = 882.37($C_{65}H_{46}N_4$ = 883.11) | P-80 | m/z = 759.27($C_{54}H_{37}N_3S$ = 759.97) |
| P-81 | m/z = 753.31($C_{56}H_{39}N_3$ = 753.95) | P-82 | m/z = 845.38($C_{63}H_{47}N_3$ = 846.09) |
| P-83 | m/z = 859.30($C_{62}H_{41}N_3S$ = 860.09) | P-84 | m/z = 1041.32($C_{74}H_{47}N_3S_2$ = 1042.33) |
| P-85 | m/z = 805.35($C_{60}H_{43}N_3$ = 806.03) | P-86 | m/z = 805.35($C_{60}H_{43}N_3$ = 806.03) |
| P-87 | m/z = 780.33($C_{57}H_{40}N_4$ = 780.98) | P-88 | m/z = 769.35($C_{57}H_{43}N_3$ = 769.99) |
| P-89 | m/z = 743.29($C_{54}H_{37}N_3O$ = 743.91) | P-90 | m/z = 759.27($C_{54}H_{37}N_3S$ = 759.97) |
| P-91 | m/z = 759.27($C_{54}H_{37}N_3S$ = 759.97) | P-92 | m/z = 759.27($C_{54}H_{37}N_3S$ = 759.97) |
| P-93 | m/z = 835.30($C_{60}H_{41}N_3S$ = 836.07) | P-94 | m/z = 835.30($C_{60}H_{41}N_3S$ = 836.07) |
| P-95 | m/z = 865.26($C_{60}H_{39}N_3S_2$ = 866.11) | P-96 | m/z = 759.27($C_{54}H_{37}N_3S$ = 759.97) |
| P-97 | m/z = 899.30($C_{64}H_{41}N_3OS$ = 900.11) | P-98 | m/z = 859.30($C_{62}H_{41}N_3S$ = 860.09) |
| P-99 | m/z = 941.29($C_{66}H_{43}N_3S_2$ = 942.21) | P-100 | m/z = 821.38($C_{61}H_{47}N_3$ = 822.07) |
| P-101 | m/z = 859.30($C_{62}H_{41}N_3S$ = 860.09) | P-102 | m/z = 809.29($C_{58}H_{39}N_3S$ = 810.03) |
| P-103 | m/z = 904.36($C_{67}H_{44}N_4$ = 905.12) | P-104 | m/z = 803.33($C_{60}H_{41}N_3$ = 804.01) |
| P-105 | m/z = 919.36($C_{68}H_{45}N_3O$ = 920.13) | | |

In the above, an exemplary synthesis example of the present invention represented by the general formula 1 are described, but all of them are based on Buchwald-Hartwig cross coupling reaction, Suzuki cross-coupling reaction, Ullmann reaction, Miyaura boration reaction and the like. Therefore, it will be understood by those skilled in the art that the above reaction proceeds even when other substituents ($Ar^1$ to $Ar^4$, $R^1$ to $R^3$, $L^1$, m, n and o) defined in Formula 1 are bonded, in addition to the substituents specified in the specific synthesis example.

For example, the reaction of Sub 1 and Sub 2->Final Product in Reaction Scheme 1, the reactions of starting materials->Sub 2-I and Sub 2-I->Sub 2 in Reaction Scheme 9 are all based on the Buchwald-Hartwig cross coupling reaction, the reaction of Sub 1-II->Sub 1 in Reaction Scheme 2 is based on the Suzuki cross-coupling reaction, the reaction of starting materials->Sub 1-1 in Reaction Scheme 3 is based on the Ullmann reaction, and the reaction of Sub 1-I->Sub 1-II in Reaction Scheme 3 is based on the Miyaura boration reaction. The above reactions will proceed even if a substituent not specifically mentioned is attached.

Fabrication and Evaluation of Organic Electronic Element

[Example 1] Red OLED (an Emission-Auxiliary Layer)

Organic light emitting diode (OLED) was fabricated according to a conventional method by using a compound of the present invention as an emission-auxiliary layer material. First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm.

Subsequently, 4,4'-bis[N-(1-napthyl)-N-phenyl-amino] biphenyl (hereinafter, "NPD") was vacuum-deposited with a thickness of 60 nm on the hole injection layer to form a hole transport layer. Subsequently, a film of the compound P-1 of the present invention was vacuum-deposited on the hole transport layer to form an emission-auxiliary layer with a thickness of 20 nm. A light emitting layer with a thickness of 30 nm was deposited on the emission-auxiliary layer by using 4,4'-N,N'-dicarbazole-biphenyl (hereinafter, "CBP") as a host material and bis-(1-phenylisoquinoline)iridium(III) acetylacetonate (hereinafter, "(piq)₂Ir(acac)") as a dopant material in a weight ratio of 95:5. Next, a film of (1,1'-biphenyl-4-olato)bis(2-methyl-8-quinolinolato)aluminum (hereinafter, "BAlq") was vacuum-deposited with a thickness of 5 nm on the light emitting layer to form a hole blocking layer, and a film of Bis(10-hydroxybenzo[h]quinolinato)berylium (hereinafter, "BeBq₂") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 50] Red OLED (an Emission-Auxiliary Layer)

The OLEDs were fabricated in the same manner as described in Example 1 except that the compounds of the present invention described in the following Table 4, instead of the compound P-1 of the present invention, were used as an emission-auxiliary layer material.

Comparative Example 1

The OLED was fabricated in the same manner as described in Example 1 except that an emission-auxiliary layer was not formed.

[Comparative Example 2] to [Comparative Example 6] Red OLED (an Emission-Auxiliary Layer)

The OLEDs were fabricated in the same manner as described in Example 1 except that the Comparative compounds 1 to 5 described in the following Table 4, instead of the compound P-1 of the present invention, were used as an emission-auxiliary layer material.

<Comp. compd 1>

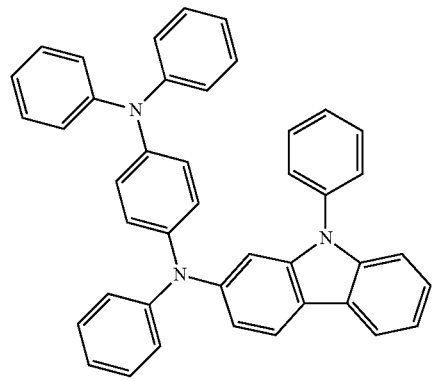

<Comp. compd 2>

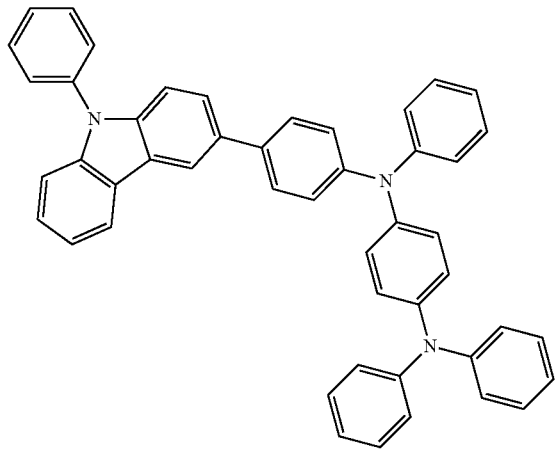

<Comp. compd 3>

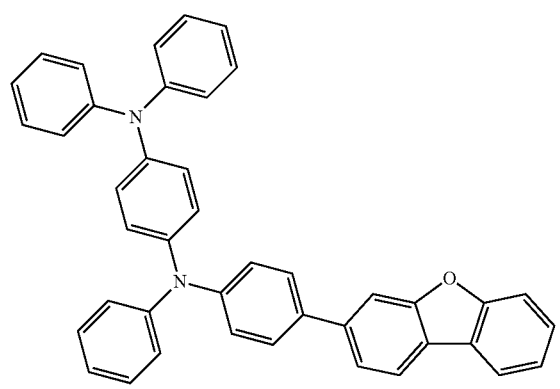

-continued

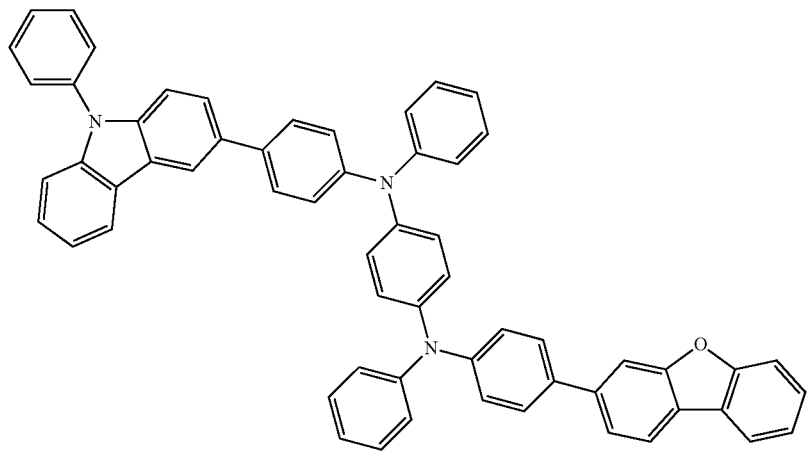
<Comp. compd 4>

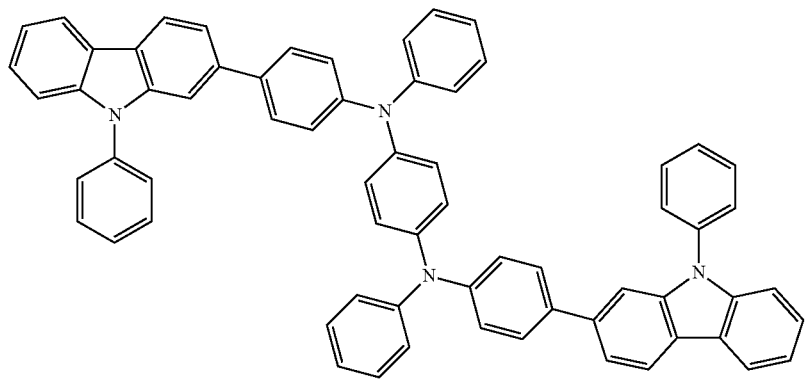
<Comp. compd 5>

Electroluminescence (EL) characteristics were measured with a PR-650 (Photoresearch) by applying a forward bias DC voltage to the OLEDs prepared in Examples 1 to 50 of the present invention and Comparative Examples 1 to 6. And, the T95 life time was measured using a life time measuring apparatus manufactured by Macscience Inc. at reference brightness of 2500 cd/m². The measurement results are shown in Tables 4 below.

TABLE 4

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex(1) | — | 5.3 | 33.3 | 2500 | 7.5 | 62.7 | 0.66 | 0.32 |
| comp. Ex(2) | comp. Com1 | 5.7 | 30.9 | 2500 | 8.1 | 72.2 | 0.66 | 0.32 |
| comp. Ex(3) | comp. Com2 | 5.8 | 26.6 | 2500 | 9.4 | 75.4 | 0.66 | 0.33 |
| comp. Ex(4) | comp. Com3 | 5.7 | 24.5 | 2500 | 10.2 | 79.8 | 0.66 | 0.33 |
| comp. Ex(5) | comp. Com4 | 5.7 | 20.8 | 2500 | 12.0 | 85.9 | 0.66 | 0.33 |
| comp. Ex(6) | comp. Com5 | 5.6 | 19.1 | 2500 | 13.1 | 91.2 | 0.66 | 0.32 |
| Ex.(1) | Com.(P-1) | 5.6 | 13.9 | 2500 | 18.0 | 120.5 | 0.66 | 0.32 |
| Ex.(2) | Com.(P-2) | 5.6 | 13.4 | 2500 | 18.7 | 127.3 | 0.66 | 0.32 |
| Ex.(3) | Com.(P-5) | 5.5 | 12.6 | 2500 | 19.8 | 130.5 | 0.66 | 0.32 |
| Ex.(4) | Com.(P-6) | 5.5 | 13.0 | 2500 | 19.2 | 131.5 | 0.66 | 0.32 |
| Ex.(5) | Com.(P-8) | 5.6 | 13.0 | 2500 | 19.2 | 131.9 | 0.66 | 0.33 |
| Ex.(6) | Com.(P-9) | 5.5 | 12.4 | 2500 | 20.1 | 134.0 | 0.66 | 0.33 |
| Ex.(7) | Com.(P-12) | 5.4 | 12.0 | 2500 | 20.8 | 133.8 | 0.66 | 0.32 |
| Ex.(8) | Com.(P-14) | 5.5 | 11.9 | 2500 | 21.0 | 136.2 | 0.66 | 0.32 |
| Ex.(9) | Com.(P-16) | 5.5 | 12.3 | 2500 | 20.3 | 134.6 | 0.66 | 0.33 |
| Ex.(10) | Com.(P-20) | 5.4 | 11.5 | 2500 | 21.7 | 136.5 | 0.66 | 0.32 |
| Ex.(11) | Com.(P-21) | 5.4 | 11.6 | 2500 | 21.5 | 136.2 | 0.66 | 0.33 |
| Ex.(12) | Com.(P-25) | 5.4 | 11.1 | 2500 | 22.6 | 138.7 | 0.66 | 0.33 |
| Ex.(13) | Com.(P-26) | 5.5 | 11.4 | 2500 | 21.9 | 139.9 | 0.66 | 0.32 |
| Ex.(14) | Com.(P-28) | 5.5 | 10.5 | 2500 | 23.7 | 140.9 | 0.66 | 0.33 |
| Ex.(15) | Com.(P-30) | 5.4 | 10.5 | 2500 | 23.9 | 142.9 | 0.66 | 0.33 |
| Ex.(16) | Com.(P-32) | 5.5 | 10.5 | 2500 | 23.8 | 144.5 | 0.66 | 0.32 |
| Ex.(17) | Com.(P-37) | 5.5 | 10.7 | 2500 | 23.3 | 138.3 | 0.66 | 0.33 |
| Ex.(18) | Com.(P-38) | 5.4 | 10.6 | 2500 | 23.5 | 138.7 | 0.66 | 0.33 |

TABLE 4-continued

| Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|
| Ex.(19) Com.(P-39) | 5.4 | 10.3 | 2500 | 24.4 | 143.9 | 0.66 | 0.33 |
| Ex.(20) Com.(P-40) | 5.5 | 10.3 | 2500 | 24.2 | 144.4 | 0.66 | 0.32 |
| Ex.(21) Com.(P-41) | 5.4 | 10.4 | 2500 | 24.1 | 143.4 | 0.66 | 0.32 |
| Ex.(22) Com.(P-42) | 5.4 | 10.4 | 2500 | 24.0 | 143.4 | 0.66 | 0.33 |
| Ex.(23) Com.(P-43) | 5.4 | 10.1 | 2500 | 24.7 | 149.9 | 0.66 | 0.32 |
| Ex.(24) Com.(P-46) | 5.3 | 9.7 | 2500 | 25.9 | 165.1 | 0.66 | 0.33 |
| Ex.(25) Com.(P-47) | 5.3 | 9.8 | 2500 | 25.6 | 157.6 | 0.66 | 0.32 |
| Ex.(26) Com.(P-48) | 5.3 | 9.8 | 2500 | 25.6 | 157.7 | 0.66 | 0.32 |
| Ex.(27) Com.(P-49) | 5.3 | 10.0 | 2500 | 25.0 | 147.3 | 0.66 | 0.33 |
| Ex.(28) Com.(P-53) | 5.3 | 10.0 | 2500 | 25.1 | 150.5 | 0.66 | 0.32 |
| Ex.(29) Com.(P-58) | 5.4 | 10.1 | 2500 | 24.8 | 151.7 | 0.66 | 0.33 |
| Ex.(30) Com.(P-60) | 5.3 | 10.1 | 2500 | 24.8 | 150.1 | 0.66 | 0.32 |
| Ex.(31) Com.(P-62) | 5.3 | 10.0 | 2500 | 25.0 | 150.5 | 0.66 | 0.33 |
| Ex.(32) Com.(P-66) | 5.4 | 10.7 | 2500 | 23.3 | 139.9 | 0.66 | 0.32 |
| Ex.(33) Com.(P-68) | 5.5 | 10.3 | 2500 | 24.3 | 143.5 | 0.66 | 0.32 |
| Ex.(34) Com.(P-69) | 5.4 | 10.5 | 2500 | 23.8 | 142.9 | 0.66 | 0.33 |
| Ex.(35) Com.(P-73) | 5.4 | 10.9 | 2500 | 22.9 | 137.9 | 0.66 | 0.33 |
| Ex.(36) Com.(P-75) | 5.4 | 10.9 | 2500 | 22.9 | 137.8 | 0.66 | 0.33 |
| Ex.(37) Com.(P-77) | 5.6 | 13.4 | 2500 | 18.7 | 122.7 | 0.66 | 0.33 |
| Ex.(38) Com.(P-78) | 5.6 | 13.0 | 2500 | 19.3 | 132.3 | 0.66 | 0.33 |
| Ex.(39) Com.(P-85) | 5.6 | 13.3 | 2500 | 18.8 | 126.6 | 0.66 | 0.33 |
| Ex.(40) Com.(P-88) | 5.6 | 13.7 | 2500 | 18.3 | 122.2 | 0.66 | 0.33 |
| Ex.(41) Com.(P-89) | 5.5 | 12.2 | 2500 | 20.5 | 134.6 | 0.66 | 0.33 |
| Ex.(42) Com.(P-90) | 5.4 | 11.8 | 2500 | 21.1 | 136.9 | 0.66 | 0.33 |
| Ex.(43) Com.(P-92) | 5.3 | 9.6 | 2500 | 26.1 | 164.4 | 0.66 | 0.32 |
| Ex.(44) Com.(P-93) | 5.3 | 9.8 | 2500 | 25.6 | 155.4 | 0.66 | 0.33 |
| Ex.(45) Com.(P-94) | 5.3 | 9.8 | 2500 | 25.5 | 158.5 | 0.66 | 0.32 |
| Ex.(46) Com.(P-95) | 5.4 | 10.3 | 2500 | 24.4 | 144.4 | 0.66 | 0.33 |
| Ex.(47) Com.(P-96) | 5.4 | 9.9 | 2500 | 25.2 | 151.8 | 0.66 | 0.32 |
| Ex.(48) Com.(P-99) | 5.4 | 10.3 | 2500 | 24.2 | 143.8 | 0.66 | 0.33 |
| Ex.(49) Com.(P-102) | 5.4 | 10.1 | 2500 | 24.7 | 147.4 | 0.66 | 0.33 |
| Ex.(50) Com.(P-105) | 5.5 | 10.9 | 2500 | 22.9 | 137.6 | 0.66 | 0.32 |

From the Table 4, it can be seen that the luminous efficiency and lifetime of the organic electroluminescent device are remarkably improved when compounds of the present invention were used as an emission-auxiliary layer material, compared Comparative Examples 1 to 6. That is, the organic electroluminescent devices employing the Comparative compounds 1 to 5, or the compounds of the present invention showed the improved luminous efficiency and lifetime, compared to the organic electroluminescent device not comprising an emission-auxiliary layer, and among them, the cases where the compounds of the present invention were used showed remarkably improved luminous efficiency and lifetime.

In particular, comparing the cases where the Comparative compounds 1 and 2 were used with the cases where the compounds of the present invention were used, it is confirmed that there is a large difference in luminous efficiency and lifetime depending on whether the linker connecting the carbazole core and the amine type (—N(Ar$^2$)-L$^1$-N(Ar$^3$)(Ar$^4$)) is introduced or not and where the linker is bonded, even if the same amine type (—N(Ar$^2$)-L$^1$-N(Ar$^3$)(Ar$^4$)) is bonded to the carbazole core. This is because the case where the linker is introduced between the carbazole core and the amine type (—N(Ar$^2$)-L$^1$-N(Ar$^3$)(Ar$^4$)) has a deeper HOM energy level than when the carbazole core and the amine type (—N(Ar$^2$)-L-N(Ar$^3$)(Ar$^4$)) are directly bonded without the linker and thus the charge balance of holes and electrons in the light emitting layer is increased as the hole can move more easily.

In addition, the compound of the present invention in which the linker is directly bonded to at the 2-position of the carbazole backbone has a shorter conjugation length than the Comparative compound 2 bonded to at the 3-position of the carbazole core, as a result, it can be seen that the band gap is widened, HOMO energy level is deepened and the value of T1 is increased.

The results depending on the number of cores or the type of the introduced atoms (N, O) on the same skeleton can be confirmed by comparing the compounds of the present invention with Comparative Compounds 3 to 5. The case where two or more carbazole cores are introduced as in Comparative Compound 5, or the case where dibenzofuran in place of carbazole is introduced as the core has a relatively low T1 value as compared with the compound of the present invention. As a result, it is confirmed that the luminous efficiency and lifetime are reduced by decreasing the ability to block electrons.

Among the compounds of the present invention, comparing the compound P-1 (linear type in which carbazole and amine are bonded at the para position of phenyl being a liker) of the present invention and the compound P-20 (non-linear type in which carbazole and amine are bonded at the meta position of phenyl being a liker), it shows different results depending on the linking type (linear type or non-linear type) of the linker.

The case where the carbazole core and the amine type (—N(Ar$^2$)-L$^1$-N(Ar$^3$)(Ar$^4$)) are bonded to the linker at the meta-position, that is non-linear type, showed deeper HOMO energy level and higher T1 value than the case where the carbazole core and the amine type (—N(Ar$^2$)-L$^1$-N(Ar$^3$)(Ar$^4$)) are bonded to the linker at the para-position, that is linear type. This shows that the compound P-20 of the present invention is improved in driving voltage, luminous efficiency and lifetime as compared with the compound P-1 of the present invention.

In addition, among the compounds of the present invention, when at least one heterocyclic substituent such as a dibenzothiophene is introduced as a substituent of an amine, the refractive index increases and the Tg value increases, comparing to the case where aryl groups are all introduced as a substituents of an amine. As a result, it can be seen that the luminous efficiency and thermal stability were improved.

In the evaluation results of the above-described device fabrication, the device characteristics has been described when the compound of the present invention is applied to only one of the hole transport layer and an emission-auxiliary layer. However, the compounds of the present invention can be used for both the hole transport layer and an emission-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

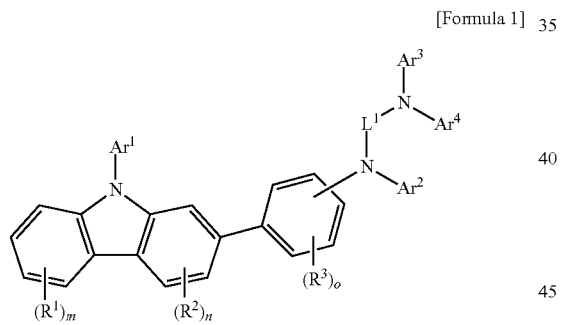

[Formula 1]

wherein:

Ar$^1$ to Ar$^4$ are each independently selected from the group consisting of a C$_6$-C$_{60}$ aryl group, a C$_2$-C$_{60}$ heterocyclic group containing at least one heteroatom selected from the group consisting of O, N, S, Si, and P, a fluorenyl group, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group and a C$_6$-C$_{30}$ aryloxy group, with the proviso that a triphenylene group is excluded from Ar$^2$ and a carbazole group is excluded from Ar$^3$ and Ar$^4$, R$^1$ to R$^3$ are each independently selected from the group consisting of deuterium, tritium, halogen, a cyano group, a nitro group, a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group and a C$_6$-C$_{30}$ aryloxy group, m is an integer of 0, or 2 to 4, n is an integer of 0, 2 or 3, o is 0, and adjacent R$^1$s or adjacent R$^2$s are linked together to form at least one monocyclic ring when m or n is each an integer of 2 or more, L$^1$ is selected from the group consisting of a C$_6$-C$_{60}$ arylene group, a fluorenylene group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, and an aliphatic hydrocarbon group, and the aryl group, arylene group, fluorenyl group, fluorenylene group, heterocyclic group, fused ring group, alkyl group, alkenyl group, alkynyl group, alkoxyl group and aryloxyl group of Ar$^1$ to Ar$^4$, R$^1$ to R$^3$ and L$^1$ are each optionally further substituted with one or more substituents selected from the group consisting of deuterium, halogen, a silane group substituted or unsubstituted with C$_1$-C$_{20}$ alkyl group or C$_6$-C$_{20}$ aryl group, a siloxane group, a boron group, a germanium group, a cyano group, a nitro group, a C$_1$-C$_{20}$ alkylthio group, a C$_1$-C$_{20}$ alkoxyl group, a C$_1$-C$_{20}$ alkyl group, a C$_2$-C$_{20}$ alkenyl group, a C$_2$-C$_{20}$ alkynyl group, a C$_6$-C$_{20}$ aryl group, a C$_6$-C$_{20}$ aryl group substituted with deuterium, a fluorenyl group, a C$_2$-C$_{20}$ heterocyclic group containing at least one heteroatom selected from the group consisting of O, N, S, Si, and P, a C$_3$-C$_{20}$ cycloalkyl group, a C$_7$-C$_{20}$ arylalkyl group and a C$_8$-C$_{20}$ arylalkenyl group, wherein adjacent substituents may optionally be linked together to form a ring, with the proviso that where an aryl group of Ar$^2$ to Ar$^4$ is substituted with a heterocyclic group, a carbazole, a dibenzothienyl group or a dibenzofuryl group is excluded from the heterocyclic group.

2. The compound of claim 1, wherein Formula 1 is represented by one of the following Formulas 2 to 4:

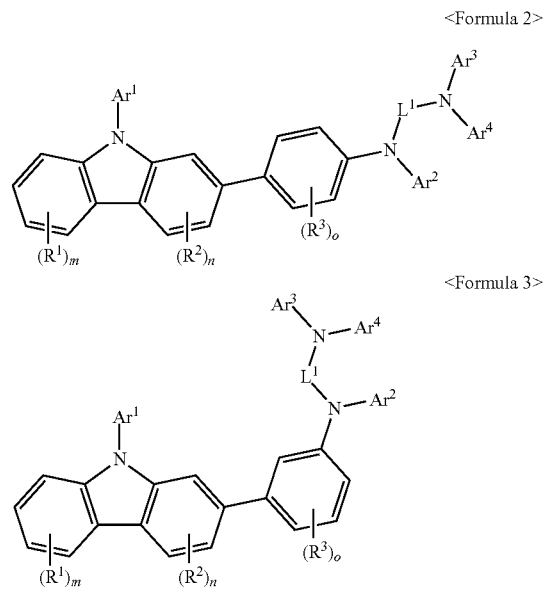

<Formula 2>

<Formula 3>

-continued

<Formula 4>

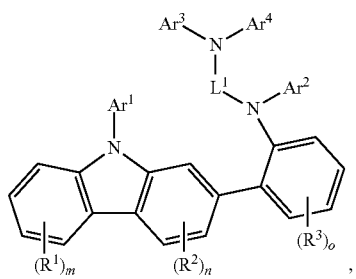

wherein Ar¹ to Ar⁴, R¹ to R³, L¹, m, n and o are the same as defined in claim 1.

3. The compound of claim 1, wherein L¹ 1 is represented by one of the following Formulas L1-1 to L1-7:

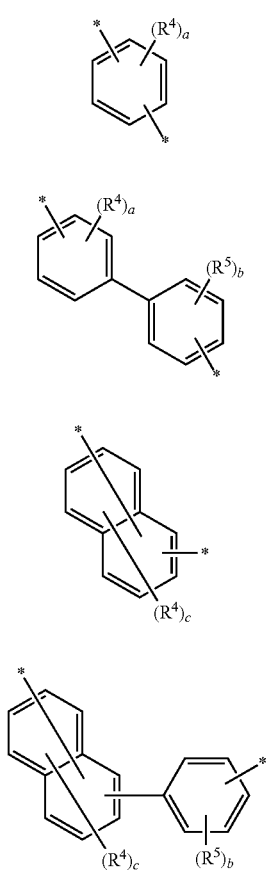

<Formula L1-6>

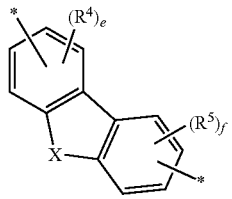

<Formula L1-7>

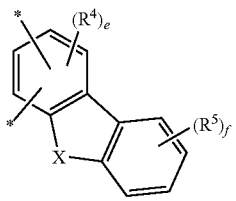

wherein:

X is S, O, $C(R^a)(R^b)$ or $N(R^c)$, wherein $R^a$, $R^b$ and $R^c$ are each independently selected from the group consisting of a $C_6$-$C_{20}$ aryl group, a fluorenyl group, a $C_2$-$C_{20}$ heterocyclic group containing at least one heteroatom selected from the group consisting of O, N, S, Si, and P, a fused ring group of a $C_3$-$C_{20}$ aliphatic ring and a $C_6$-$C_{60}$ aromatic ring, a $C_1$-$C_{20}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, and $R^a$ and $R^b$ may optionally be linked together to form a spiro compound together with a carbon to which they are bonded, $R^4$ and $R^5$ are each independently selected from the group consisting of a $C_6$-$C_{20}$ aryl group, a fluorenyl group, a $C_2$-$C_{20}$ heterocyclic group containing at least one heteroatom selected from the group consisting of O, N, S, Si, and P, a fused ring group of a $C_3$-$C_{20}$ aliphatic ring and a $C_6$-$C_{60}$ aromatic ring, a $C_1$-$C_{20}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, and a to b are each an integer of 0 to 4, c is an integer of 0 to 6, d is an integer of 0 to 5, e and f are each an integer of 0 to 3, and each of the plurality of $R^4$s and each of the plurality of $R^5$s are the same or different from each other where a, b, c, d, e and f are each an integer of 2 or more.

4. A compound of Formula 1:

[Formula 1]

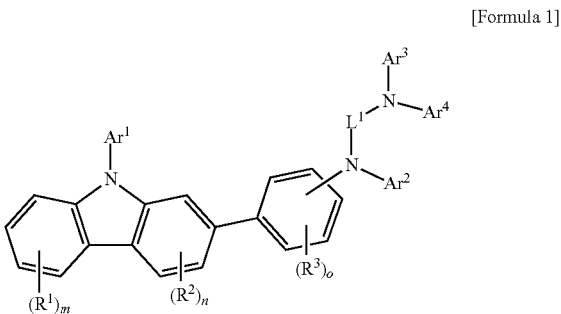

wherein:

Ar$^1$ to Ar$^4$ are each independently selected from the group consisting of a C$_6$-C$_{60}$ aryl group, a C$_2$-C$_{60}$ heterocyclic group containing at least one heteroatom selected from the group consisting of O, N, S, Si, and P, a fluorenyl group, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group and a C$_6$-C$_{30}$ aryloxy group, with the proviso that a triphenylene group is excluded from Ar$^2$ and a carbazole group is excluded from Ar$^3$ and Ar$^4$, R$^1$ to R$^3$ are each independently selected from the group consisting of deuterium, tritium, halogen, a cyano group, a nitro group, a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group and a C$_6$-C$_{30}$ aryloxy group, m and o are each an integer of 0 to 4, n is an integer of 0 to 3 and adjacent R$^1$s, adjacent R$^2$s or adjacent R$^3$s may optionally be linked together to form a ring when m, n or o is each an integer of 2 or more, L$^1$ is selected from the group consisting of a C$_6$-C$_{60}$ arylene group, a fluorenylene group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, and an aliphatic hydrocarbon group, and the aryl group, arylene group, fluorenyl group, fluorenylene group, heterocyclic group, fused ring group, alkyl group, alkenyl group, alkynyl group, alkoxyl group and aryloxyl group of Ar$^1$ to Ar$^4$, R$^1$ to R$^3$ and L$^1$ are each optionally further substituted with one or more substituents selected from the group consisting of deuterium, halogen, a silane group substituted or unsubstituted with C$_1$-C$_{20}$ alkyl group or C$_6$-C$_{20}$ aryl group, a siloxane group, a boron group, a germanium group, a cyano group, a nitro group, a C$_1$-C$_{20}$ alkylthio group, a C$_1$-C$_{20}$ alkoxyl group, a C$_1$-C$_{20}$ alkyl group, a C2-C$_{20}$ alkenyl group, a C$_2$-C$_{20}$ alkynyl group, a C$_6$-C$_{20}$ aryl group, a C$_6$-C$_{20}$ aryl group substituted with deuterium, a fluorenyl group, a C$_2$-C$_{20}$ heterocyclic group containing at least one heteroatom selected from the group consisting of O, N, S, Si, and P, a C$_3$-C$_{20}$ cycloalkyl group, a C$_7$-C$_{20}$ arylalkyl group and a C$_8$-C$_{20}$ arylalkenyl group, wherein adjacent substituents may optionally be linked together to form a ring, with the proviso that where an aryl group of Ar$^2$ to Ar$^4$ is substituted with a heterocyclic group, a carbazole, a dibenzothienyl group or a dibenzofuryl group is excluded from the heterocyclic group, wherein at least one of Ar$^1$ to Ar$^4$ is represented by the following Formula 5:

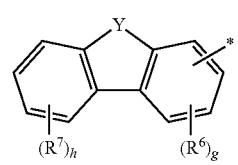

<Formula 5> wherein:

Y is S, O or C(R$^d$)(R$^e$), wherein R$^d$ and R$^e$ are each independently selected from the group consisting of a C$_6$-C$_{20}$ aryl group, a fluorenyl group, a C$_2$-C$_{20}$ heterocyclic group containing at least one heteroatom selected from the group consisting of O, N, S, Si, and P, a fused ring group of a C$_3$-C$_{20}$ aliphatic ring and a C$_6$-C$_{20}$ aromatic ring, a C$_1$-C$_{20}$ alkyl group, a C$_2$-C$_{20}$ alkenyl group, a C$_2$-C$_{20}$ alkynyl group, a C$_1$-C$_{30}$ alkoxyl group and a C$_6$-C$_{30}$ aryloxy group, R$^6$ and R$^7$ are each independently selected from the group consisting of a C$_6$-C$_{20}$ aryl group, a fluorenyl group, a C$_2$-C$_{20}$ heterocyclic group containing at least one heteroatom selected from the group consisting of O, N, S, Si, and P, a fused ring group of a C$_3$-C$_{20}$ aliphatic ring and a C$_6$-C$_{20}$ aromatic ring, a C$_1$-C$_{20}$ alkyl group, a C$_2$-C$_{20}$ alkenyl group, a C$_2$-C$_{20}$ alkynyl group, a C$_1$-C$_{30}$ alkoxyl group and a C$_6$-C$_{30}$ aryloxy group, h is an integer of 0 to 4, g is an integer of 0 to 3, and plural R$^6$s and plural R$^7$s are each the same or different from each other where h and g are each an integer of 2 or more.

5. The compound of claim 4, wherein at least one of Ar$^1$ to Ar$^4$ in the formula 1 is the formula 5 and Y in the formula 5 is S.

6. A compound selected from compounds P-1 to p-105

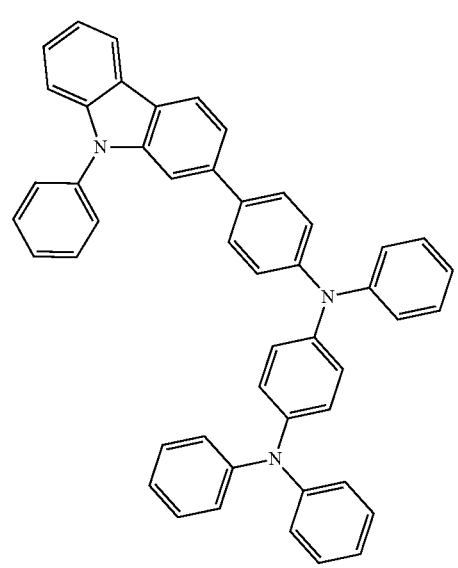

P-1

P-2
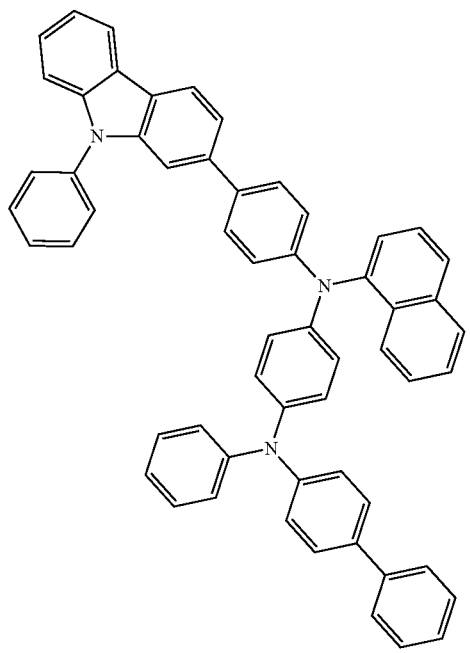
P-3
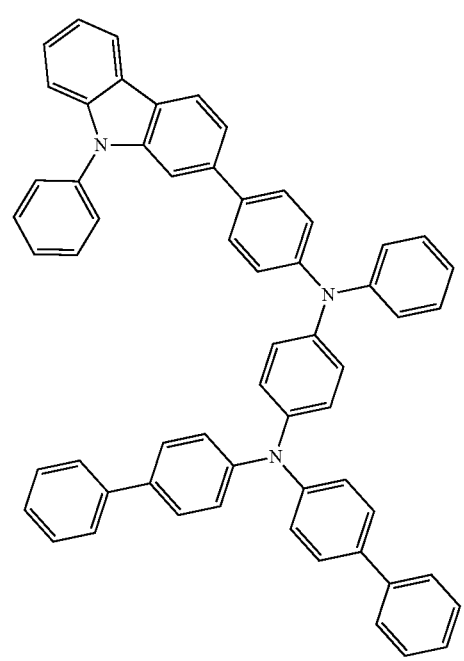
P-4
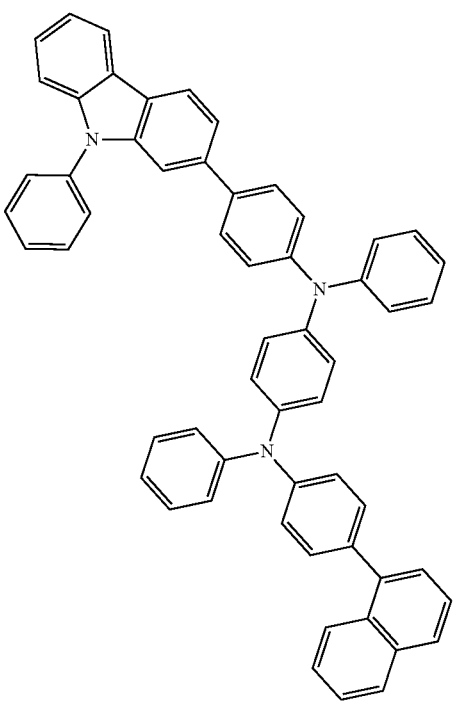
P-5
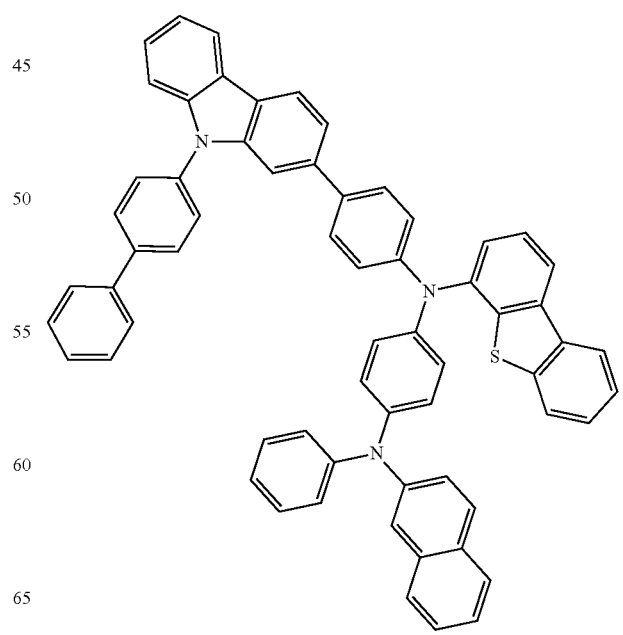

P-6
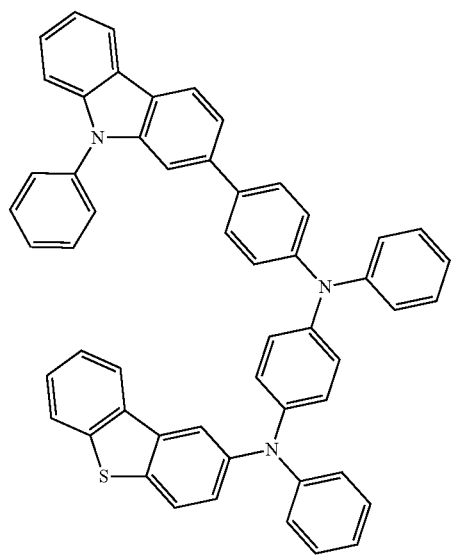
P-7
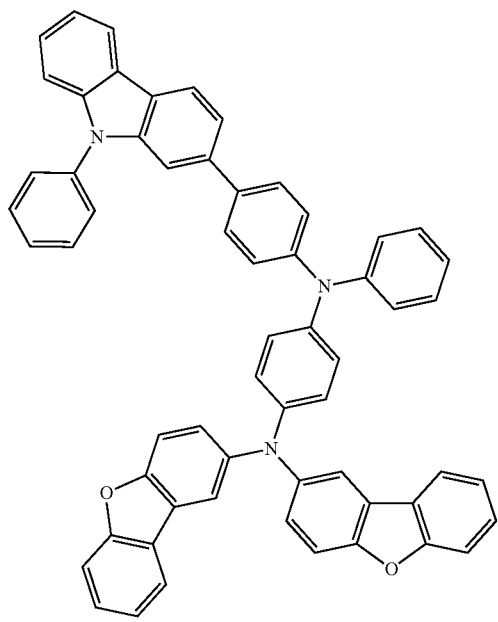
P-8
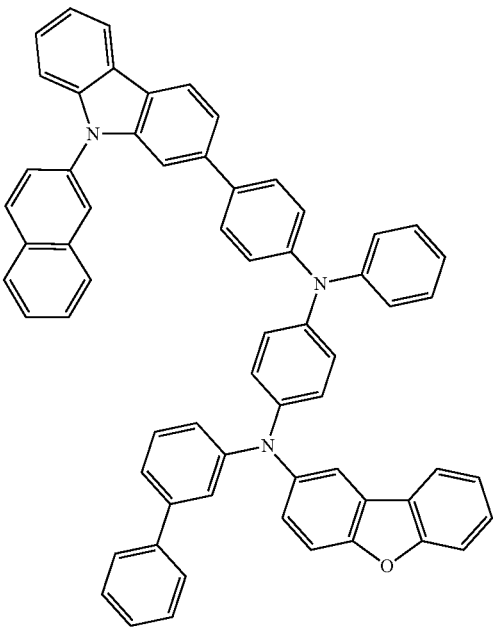
P-9
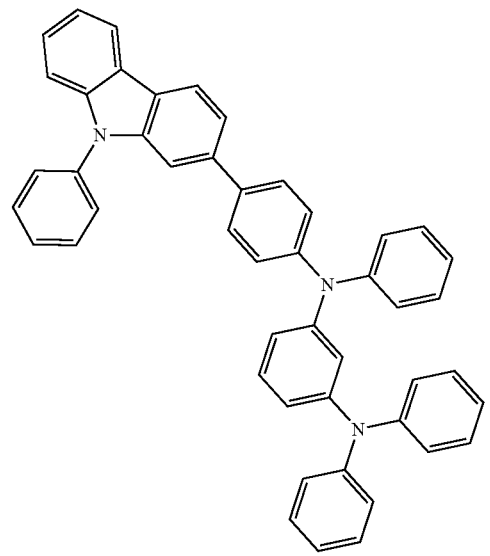

P-10
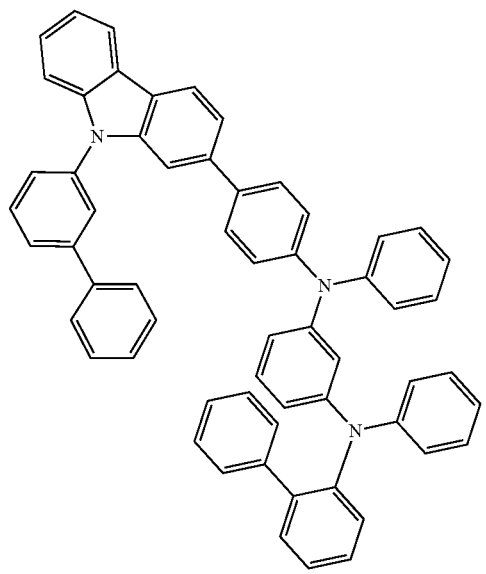
P-11
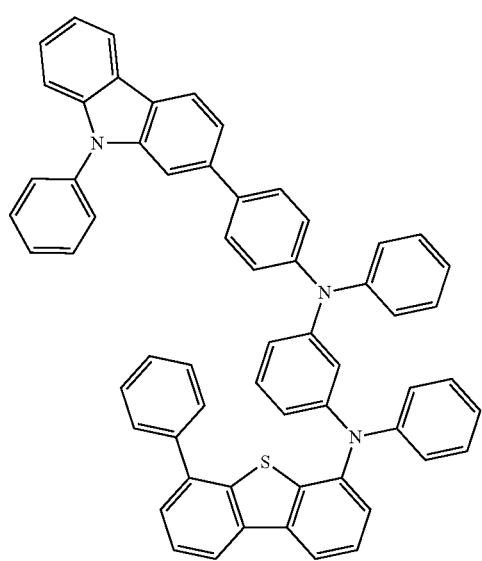
P-12
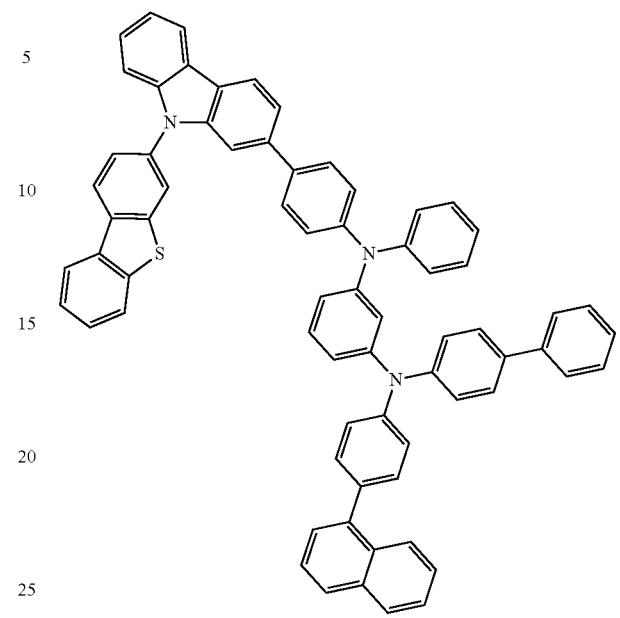
P-13
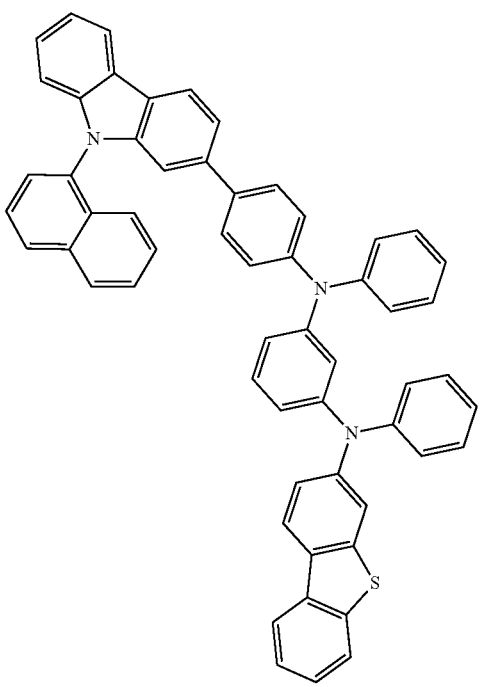

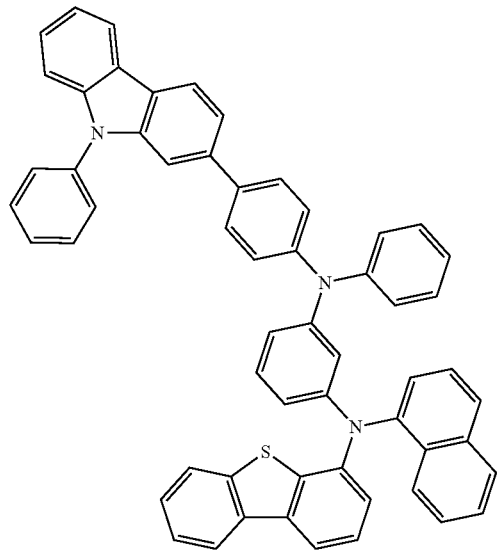
P-14
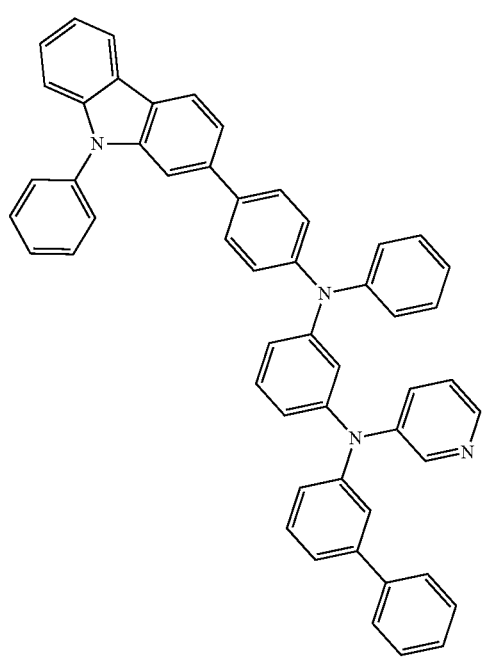
P-15
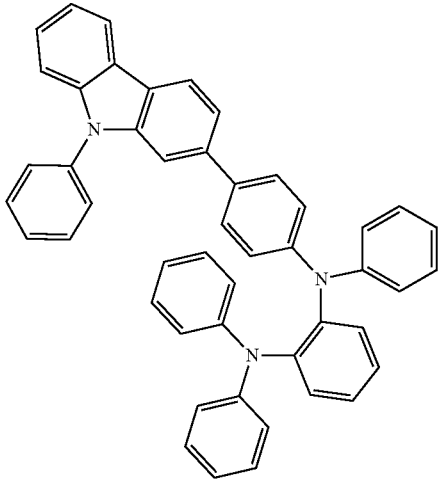
P-16
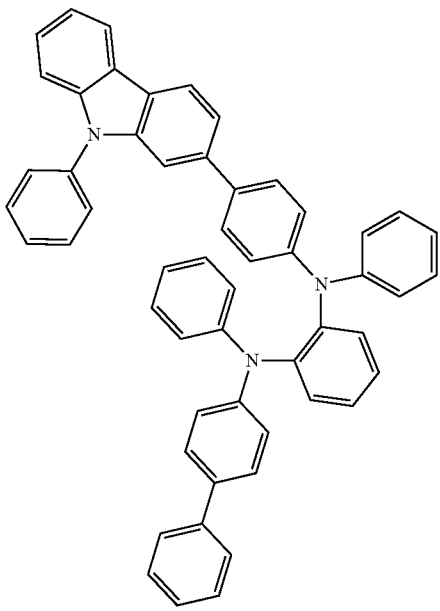
P-17
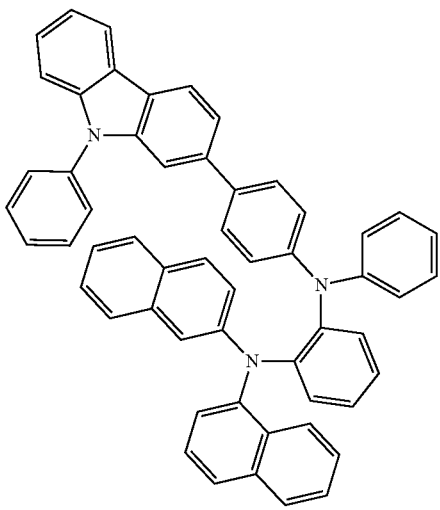
P-18

P-19
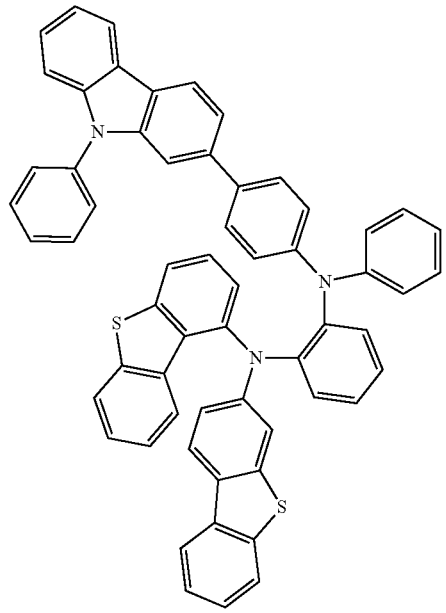
P-21
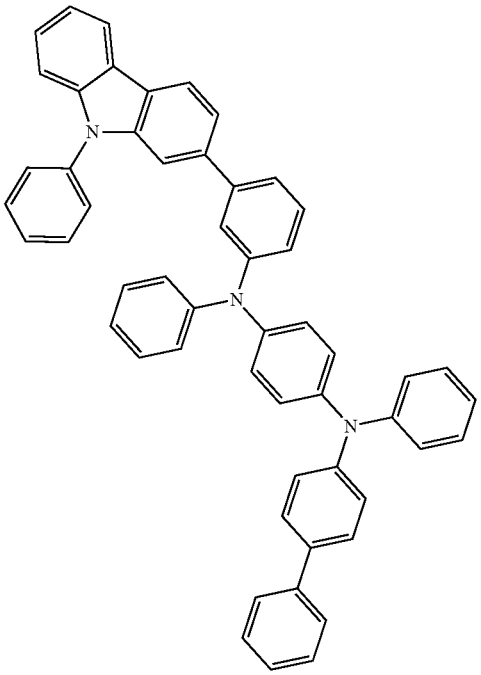
P-20
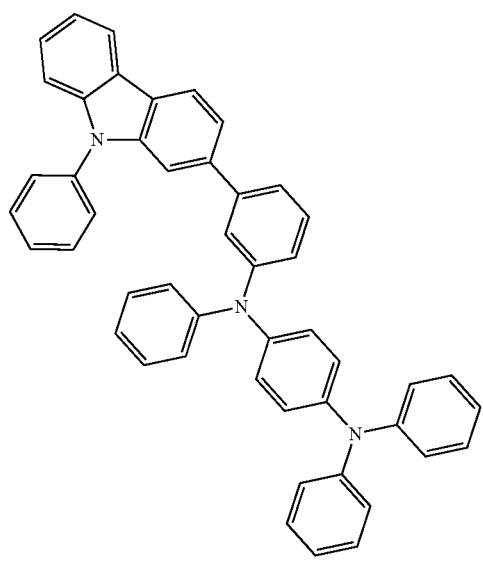
P-22
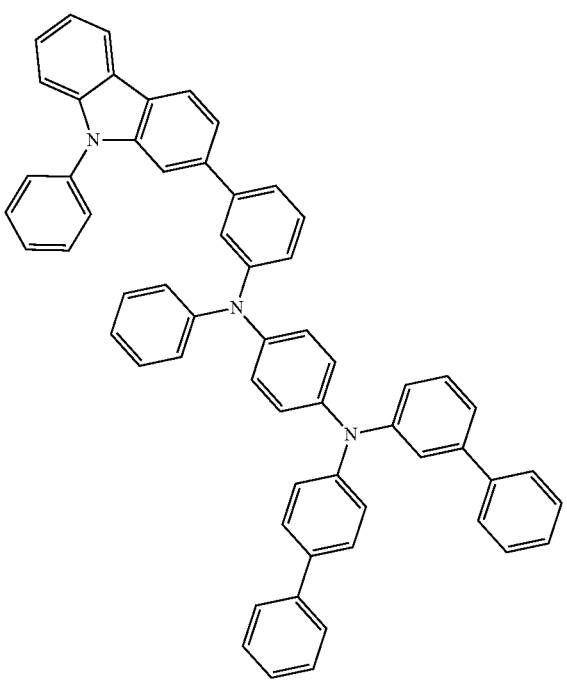

P-23
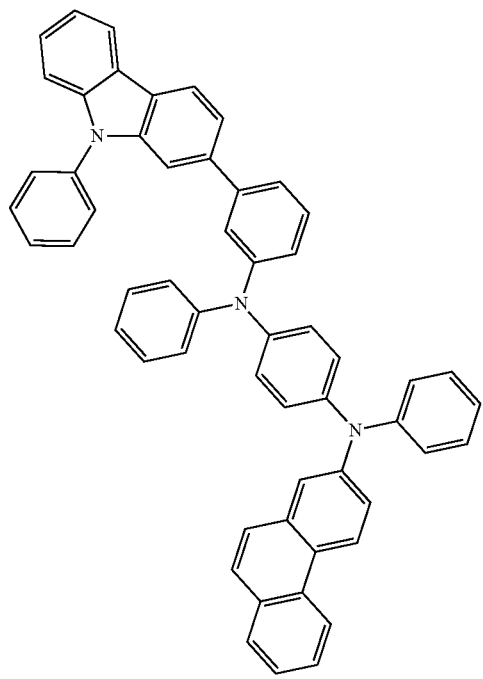
P-25
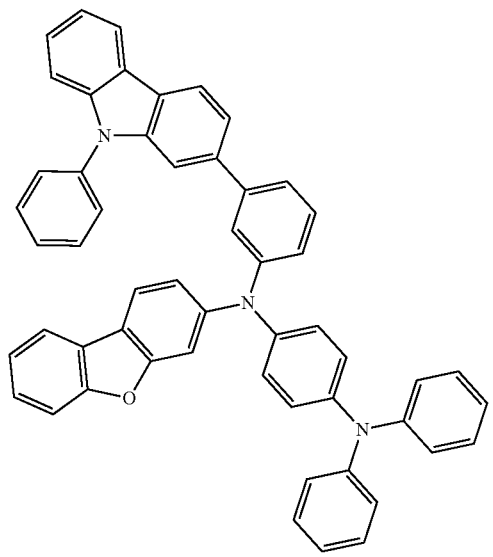
P-24
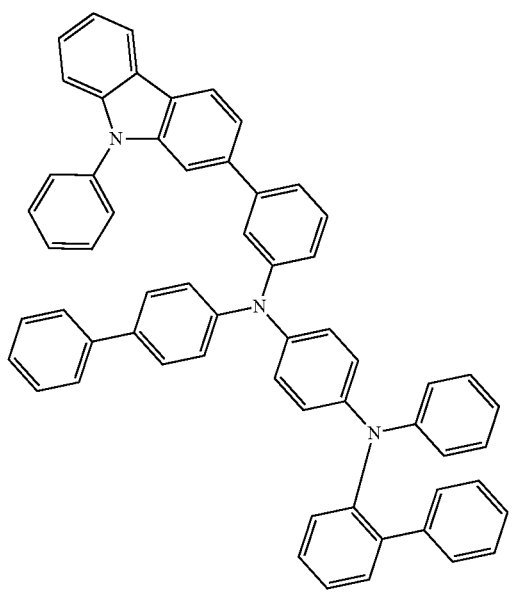
P-26
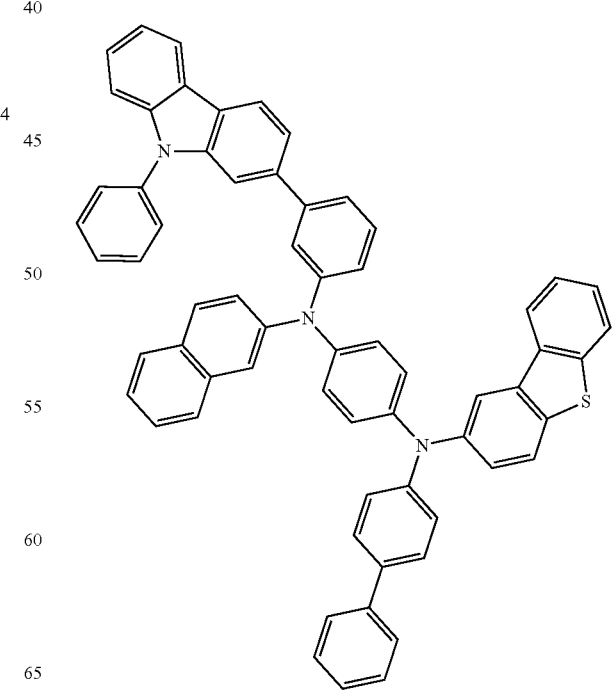

P-27
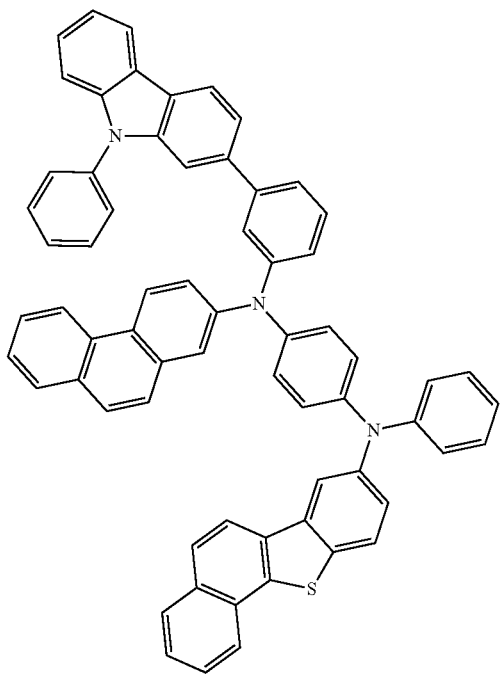
P-29
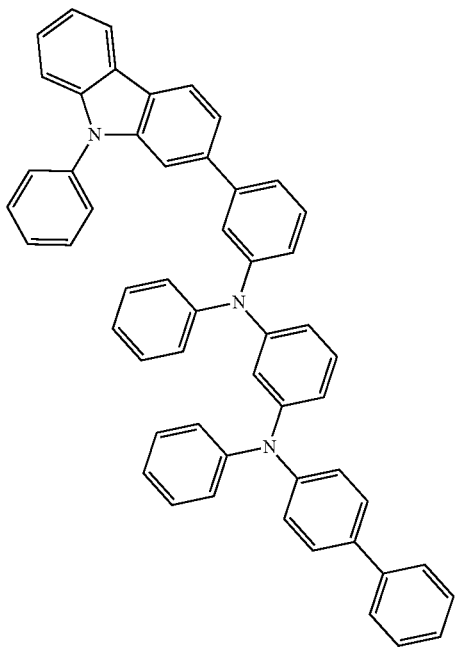
P-28
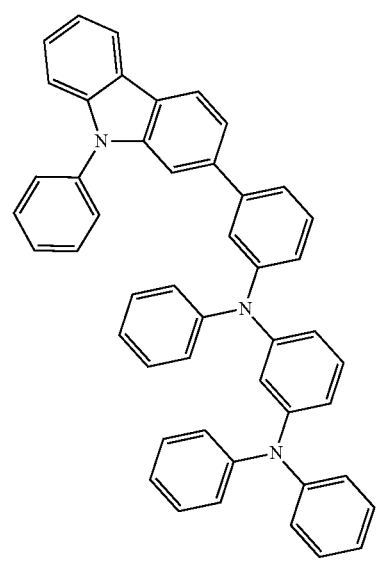
P-30
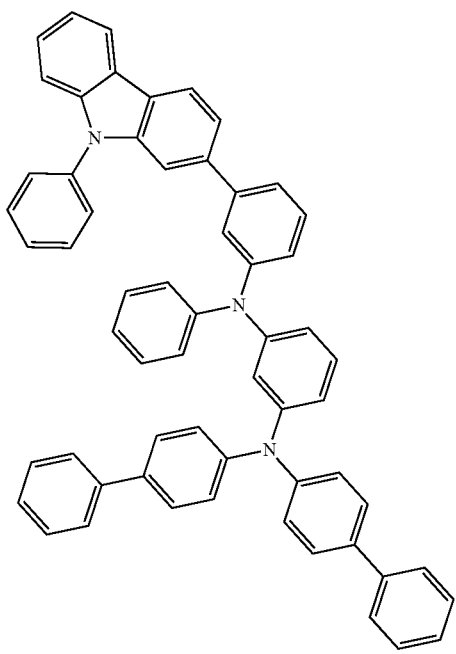

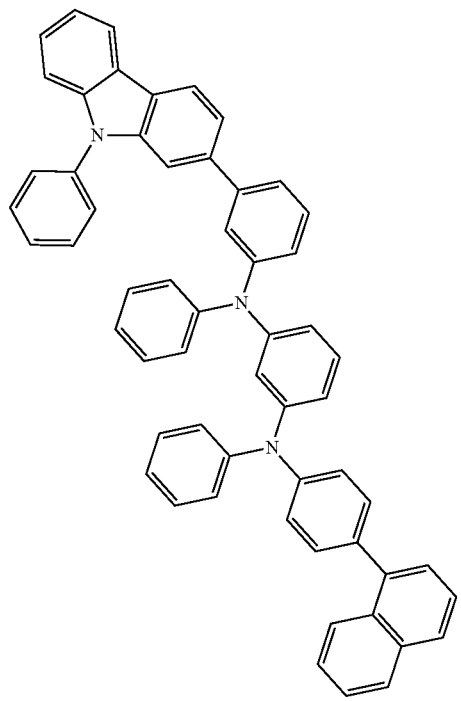
P-31
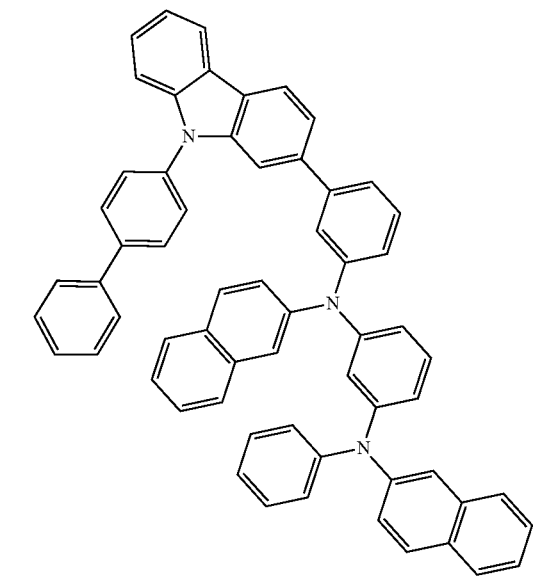
P-33
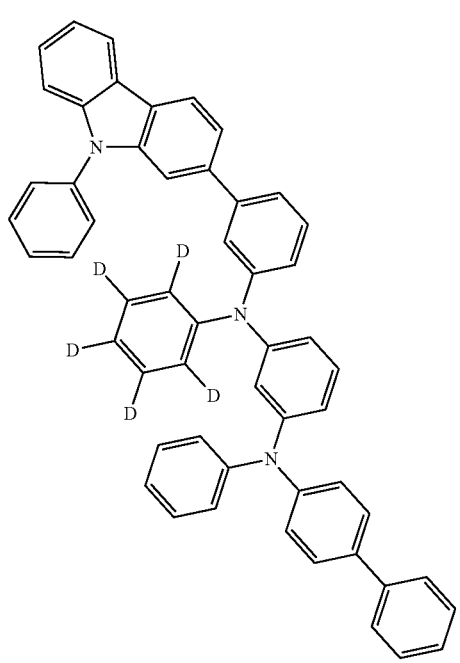
P-32
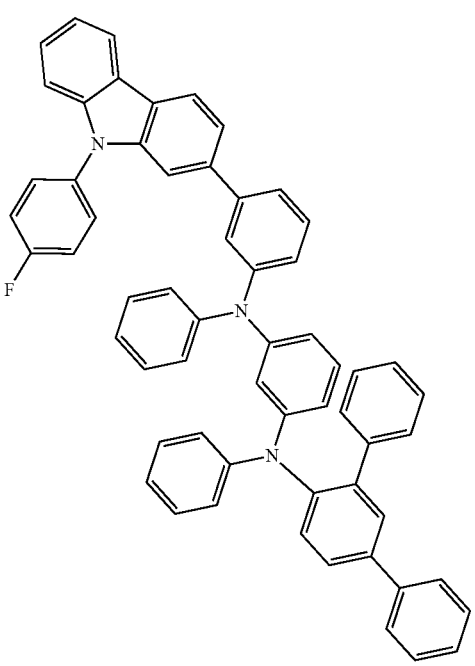
P-34

P-35
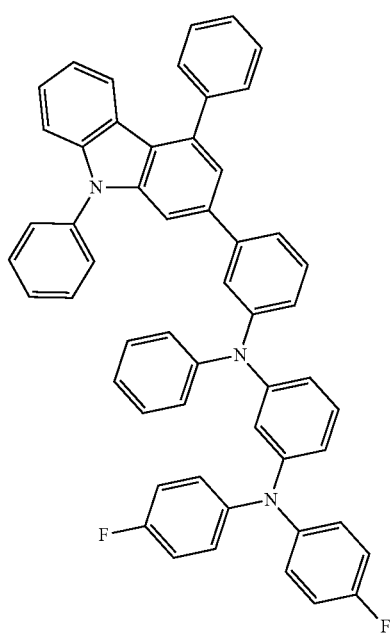
P-36
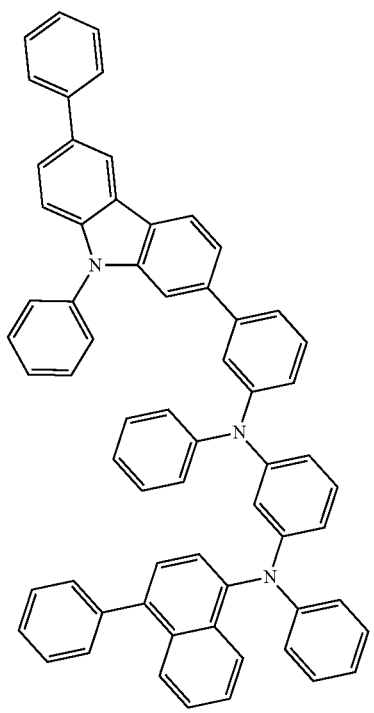
P-37
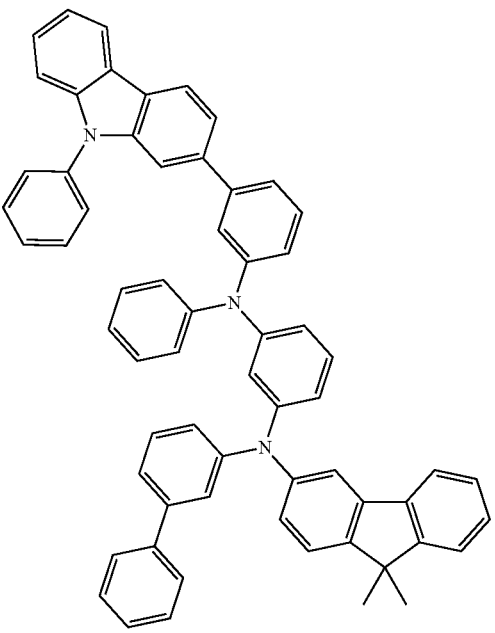
P-38
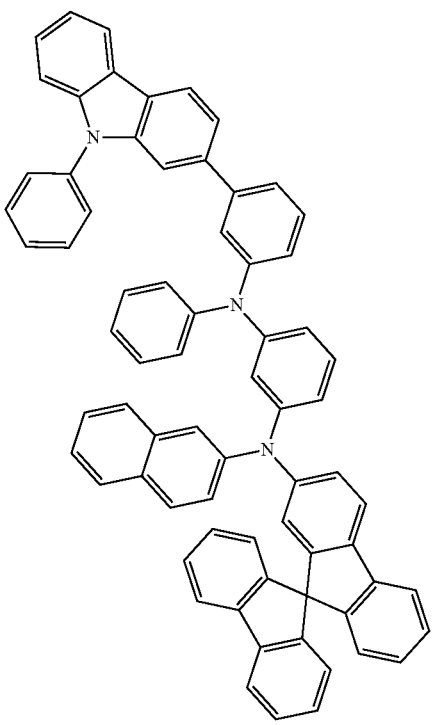

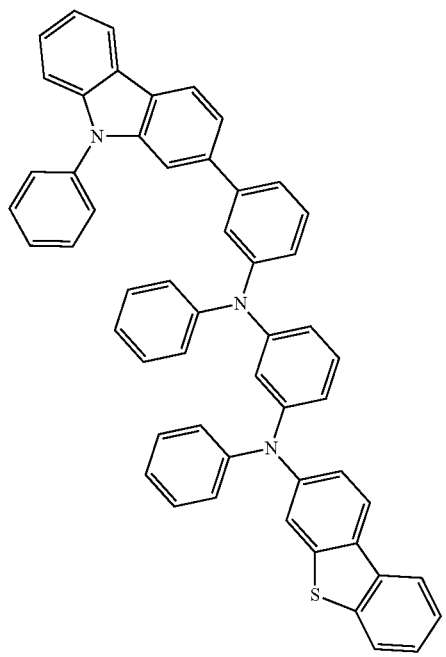
P-39
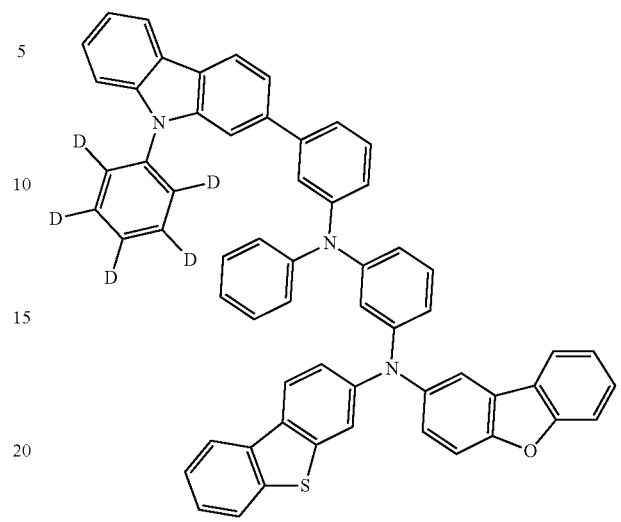
P-41
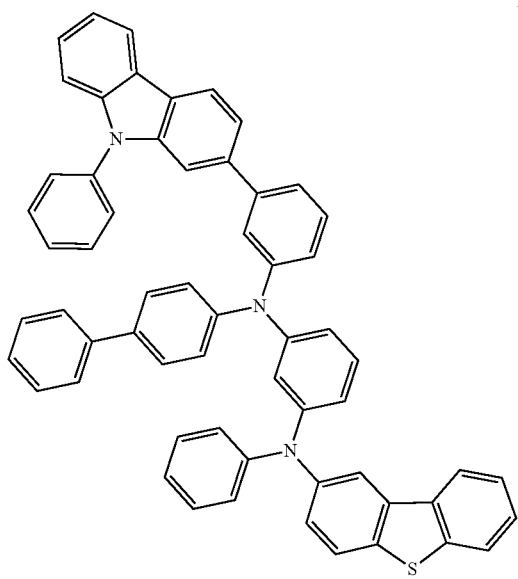
P-40
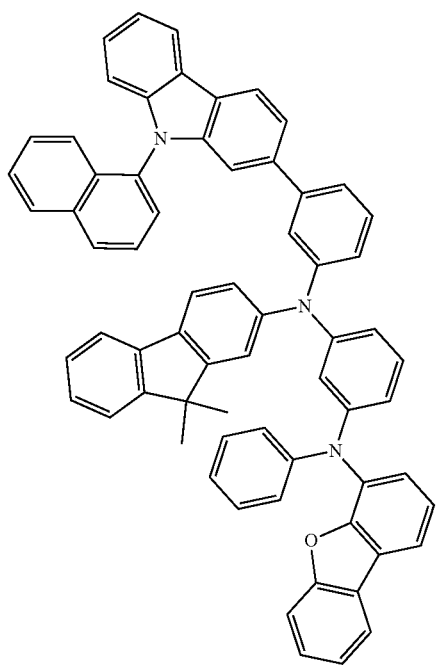
P-42

P-43
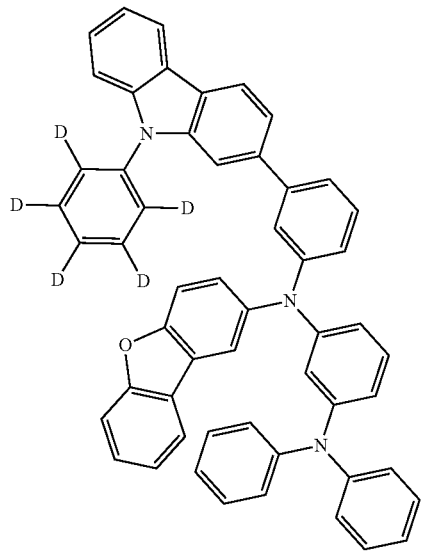
P-44
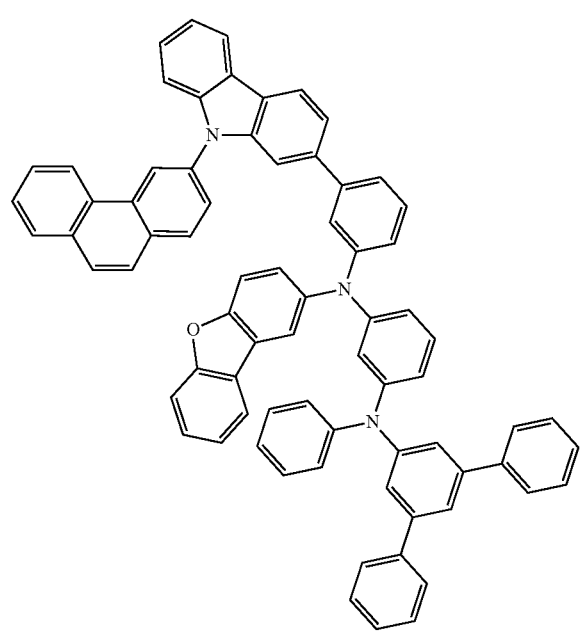
P-45
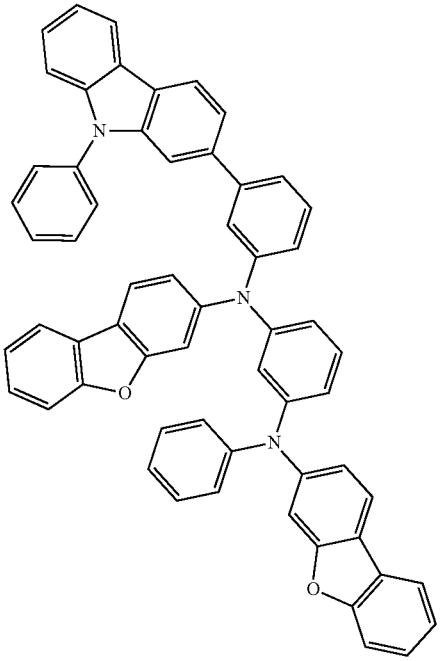
P-46
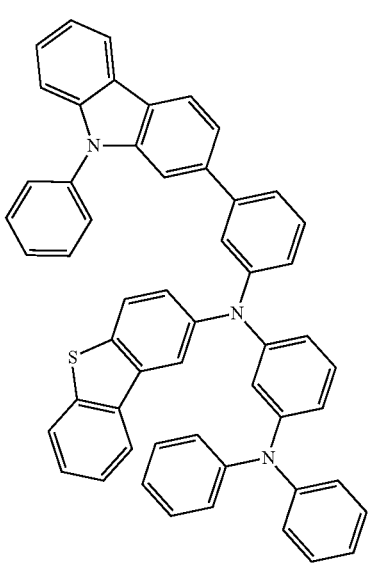

P-47
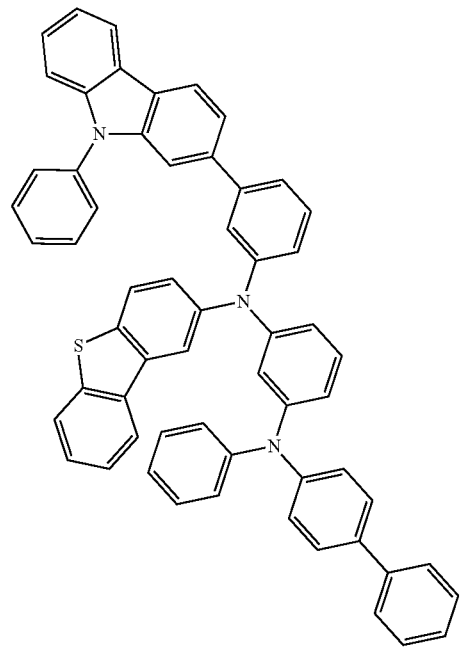
P-48
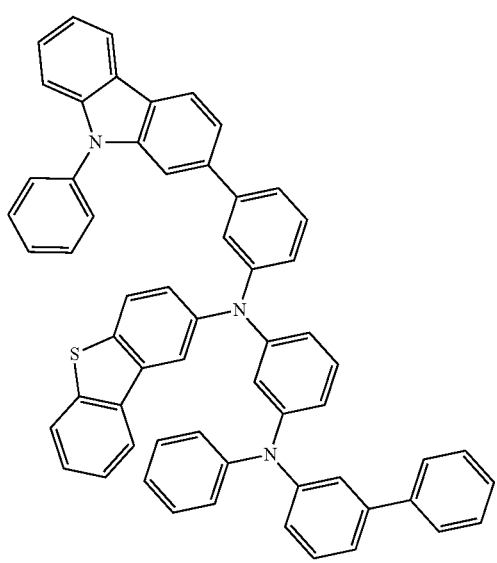
P-49
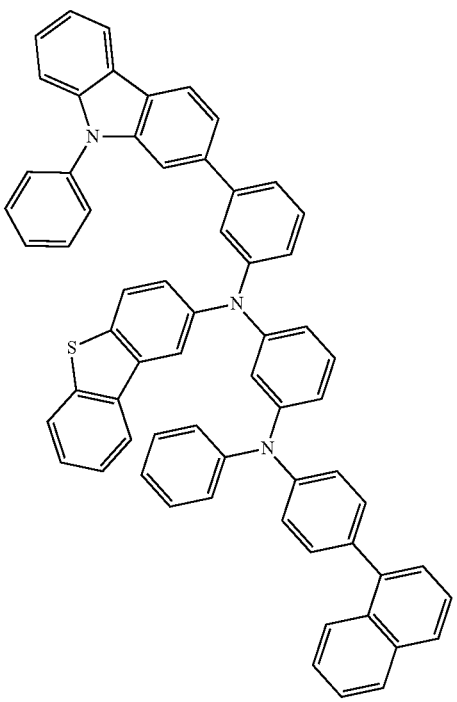
P-50
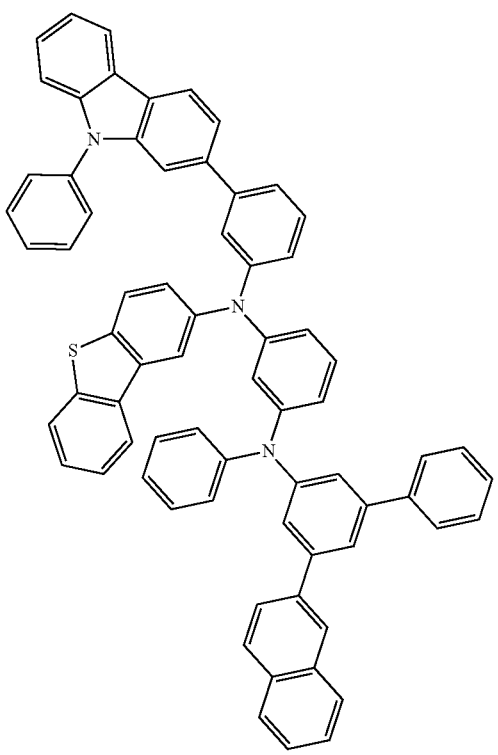

-continued
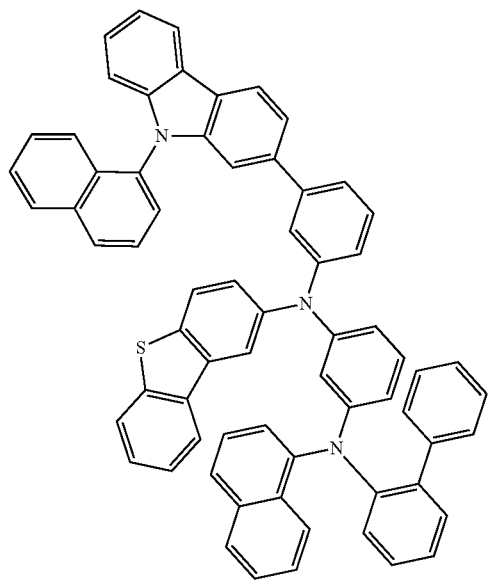
P-51
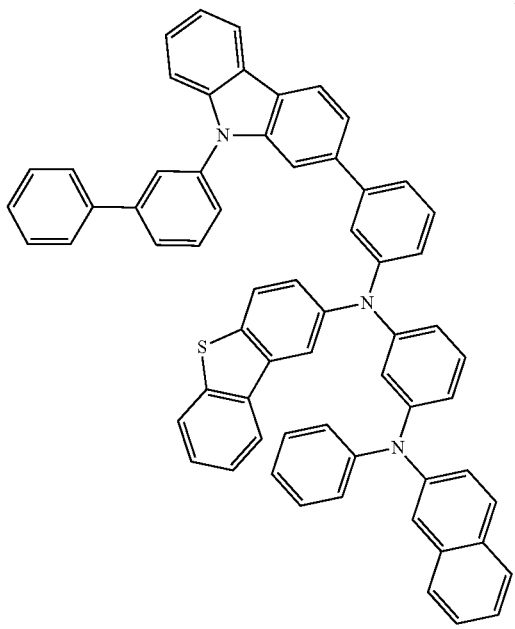
P-53
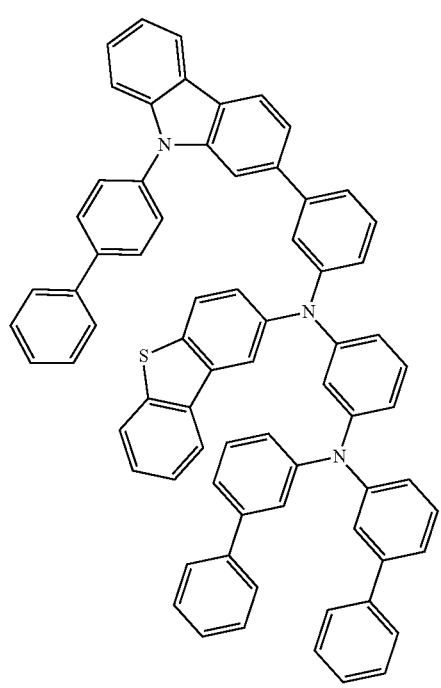
P-52
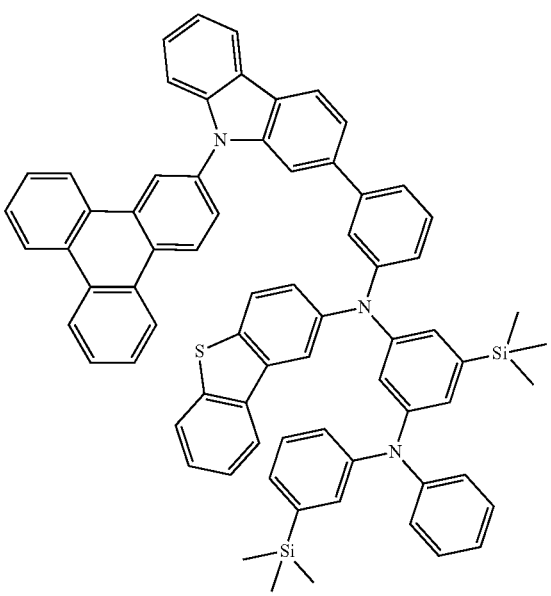
P-54

P-55
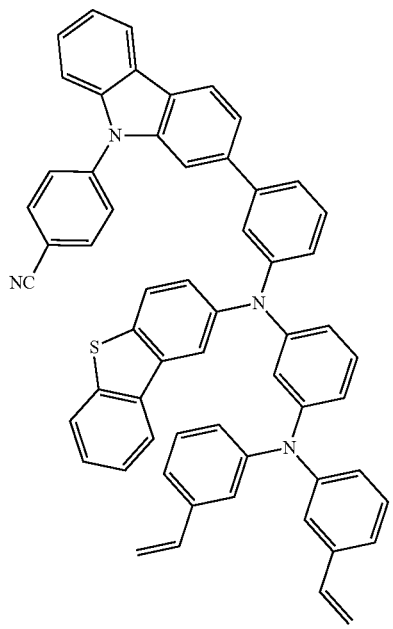
P-56
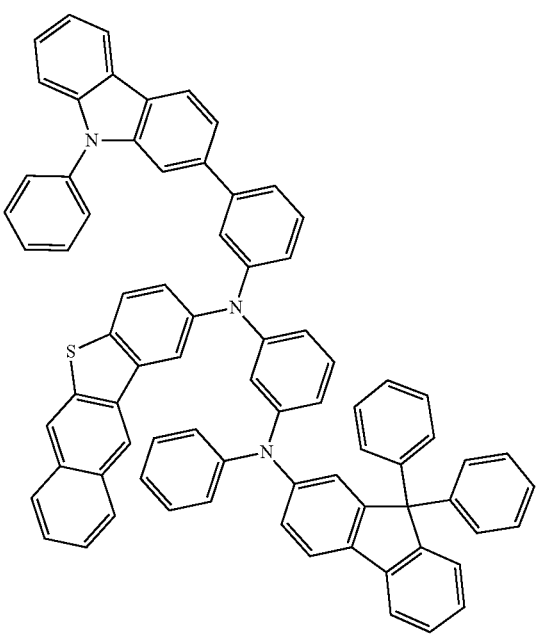
P-57
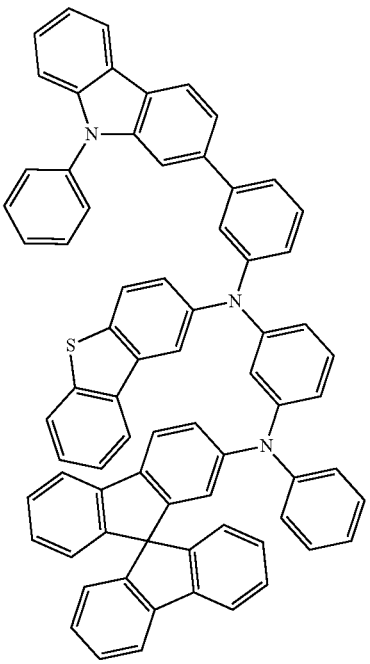
P-58
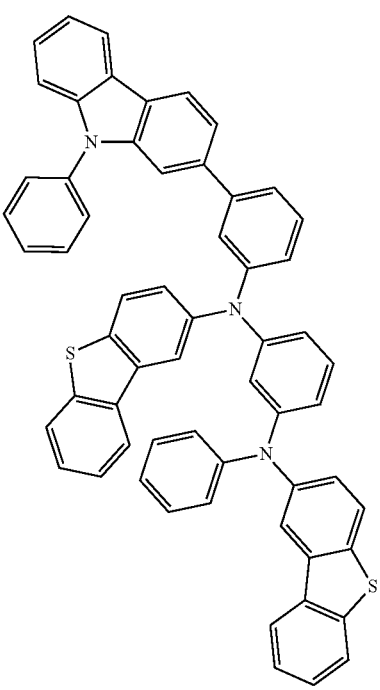

-continued
P-59
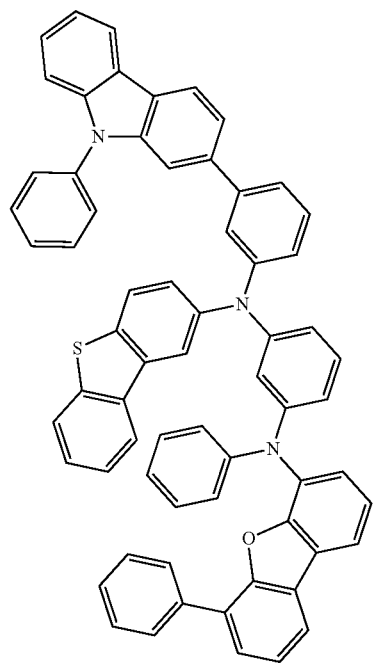
P-61
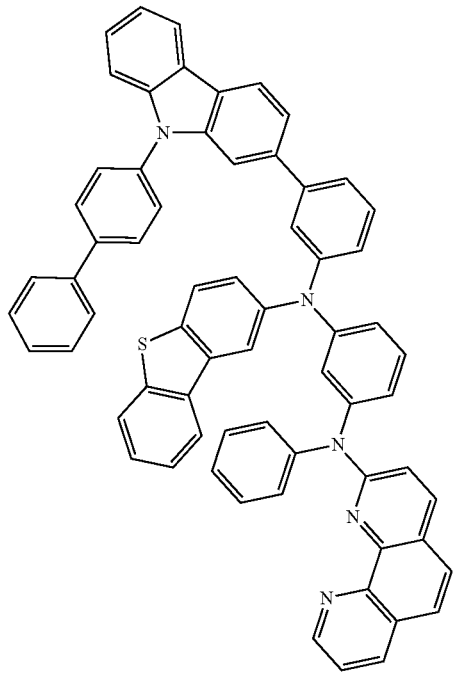
P-60
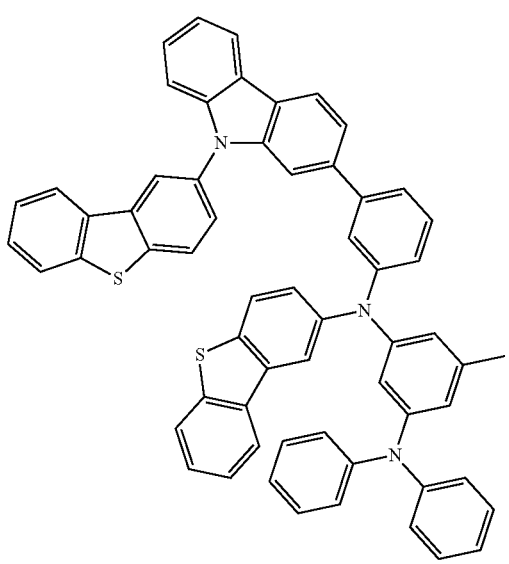
P-62
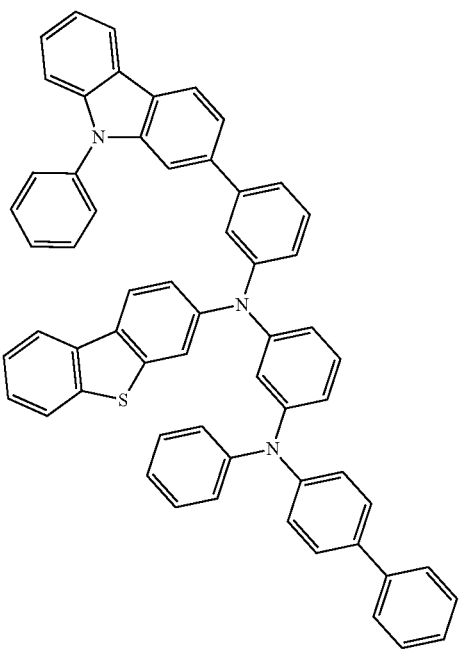

P-63
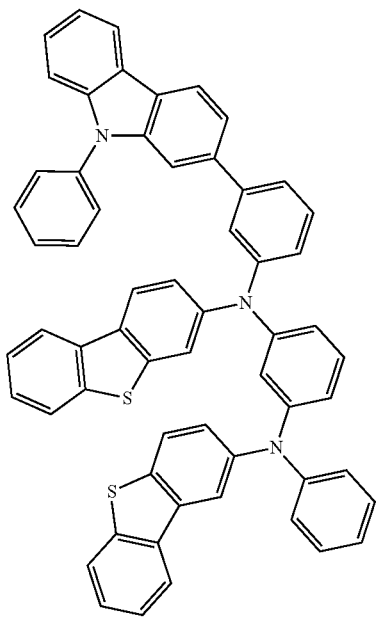
P-64
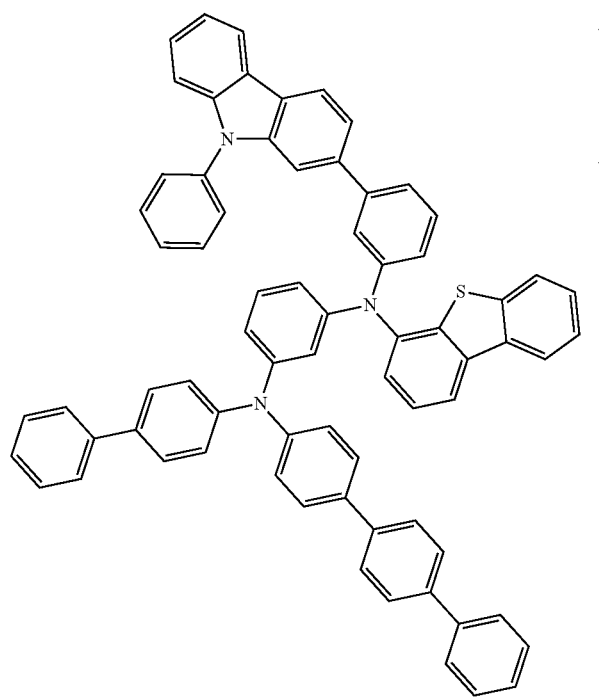
P-65
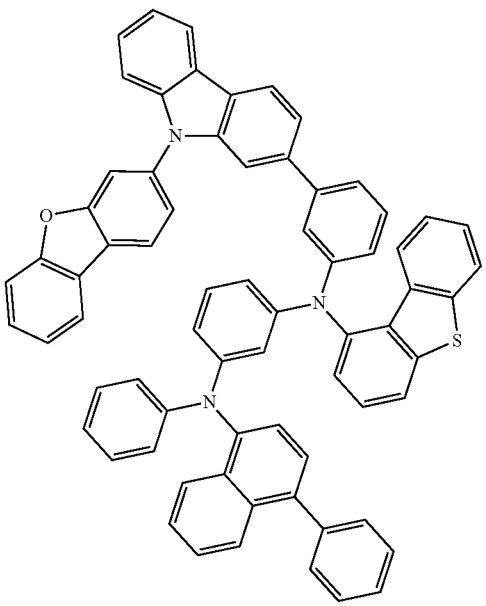
P-66
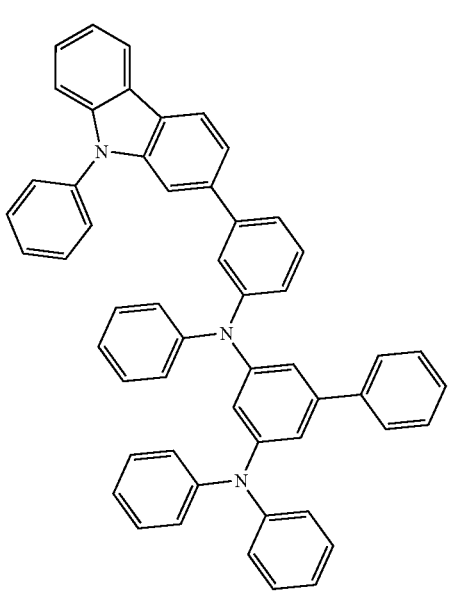

-continued
P-67
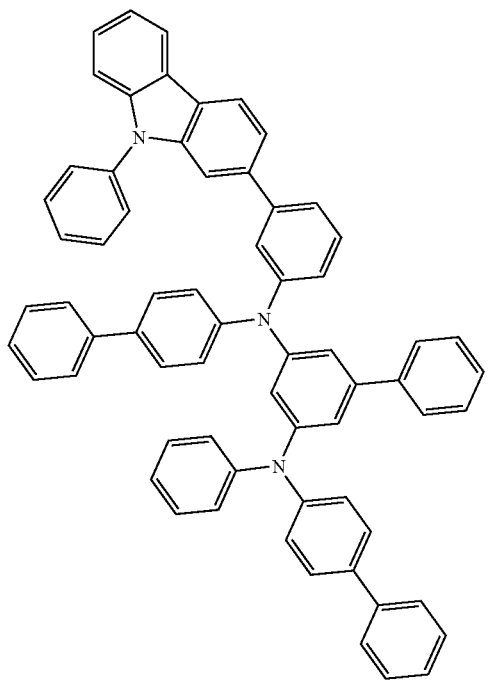
P-68
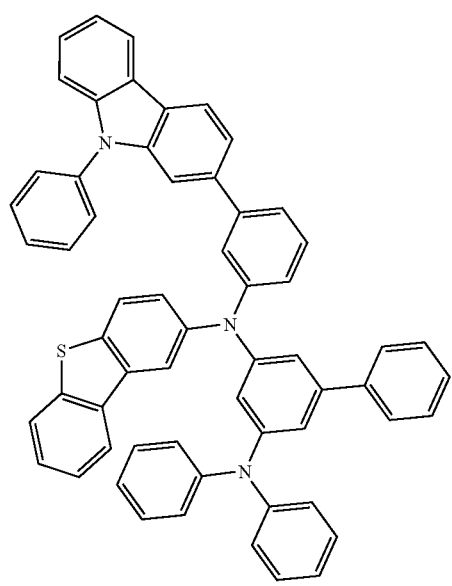
P-69
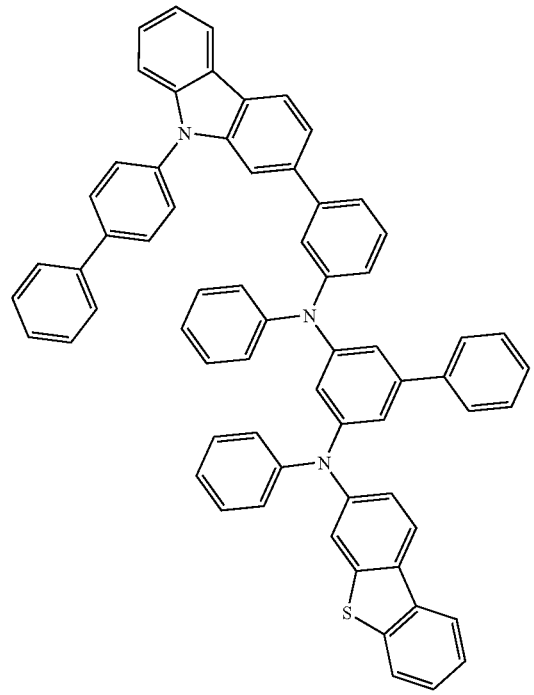
P-70
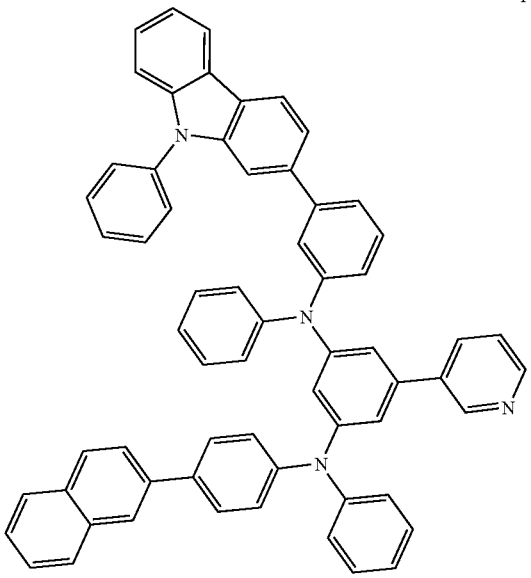

-continued
P-71
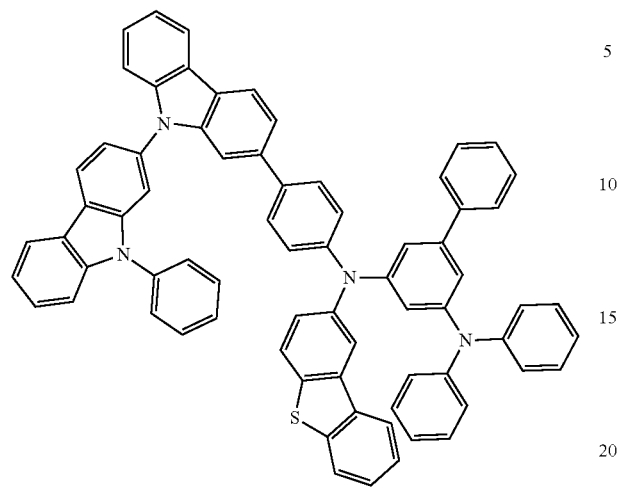
P-72
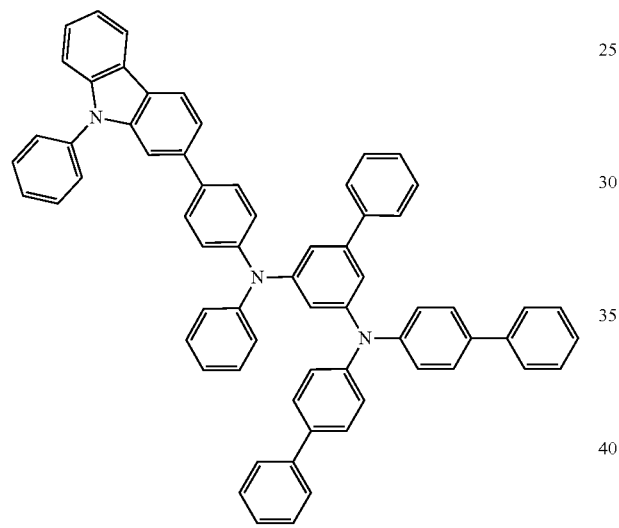
P-73
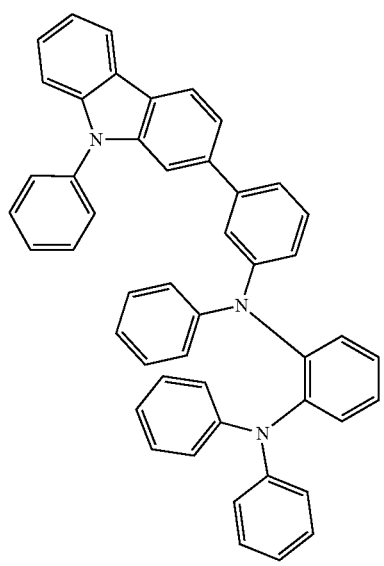
P-74
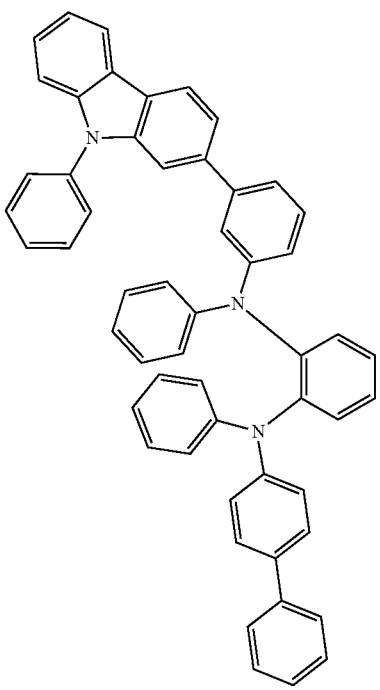
P-75
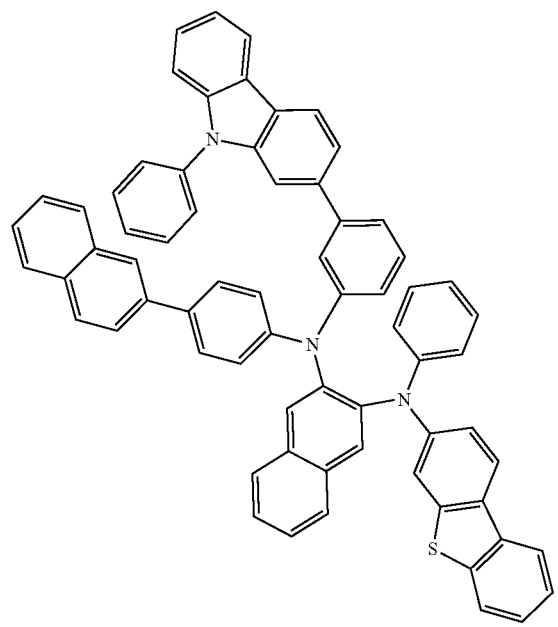

P-76
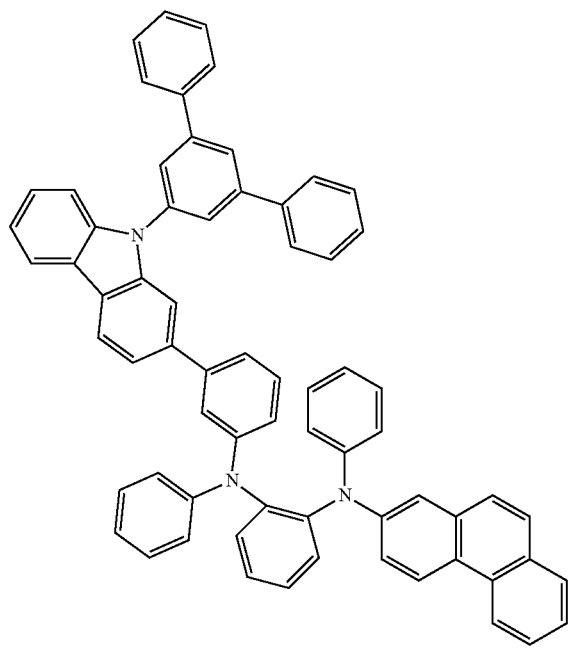
P-78
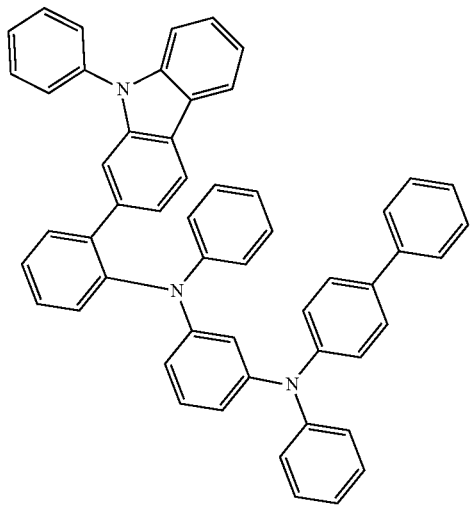
P-77
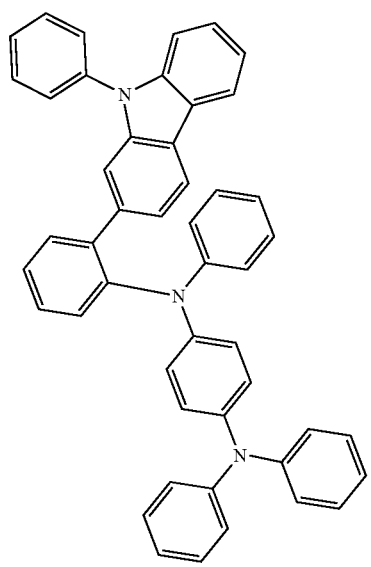
P-79
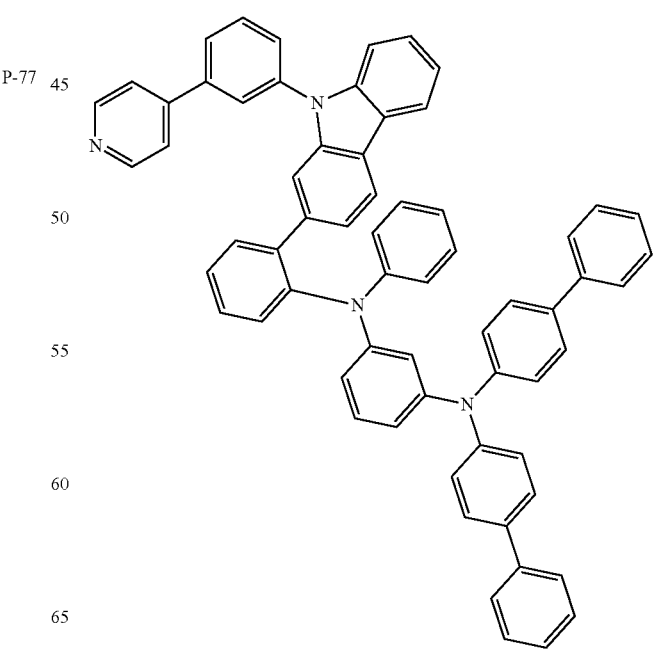

P-80
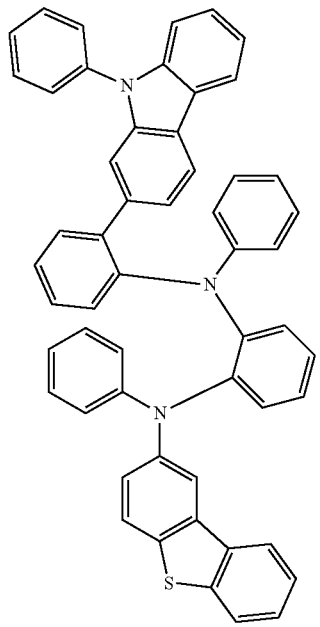
P-82
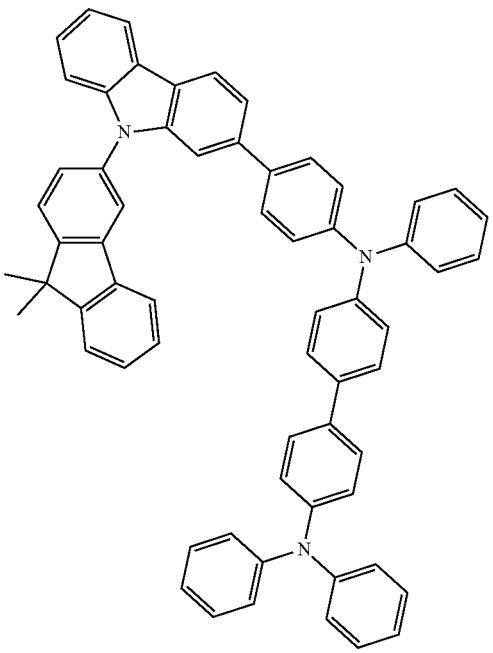
P-81
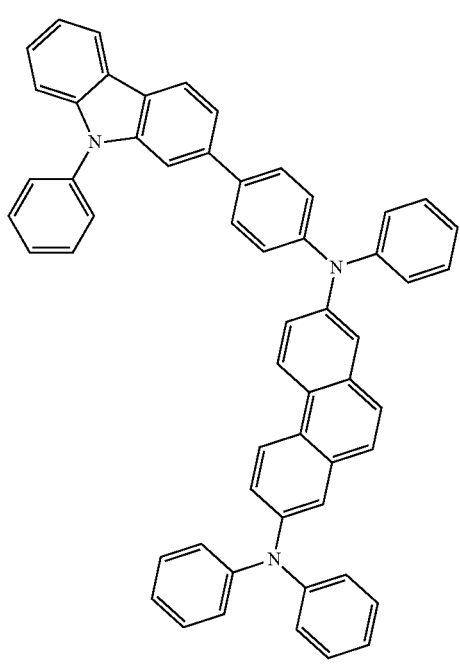
P-83
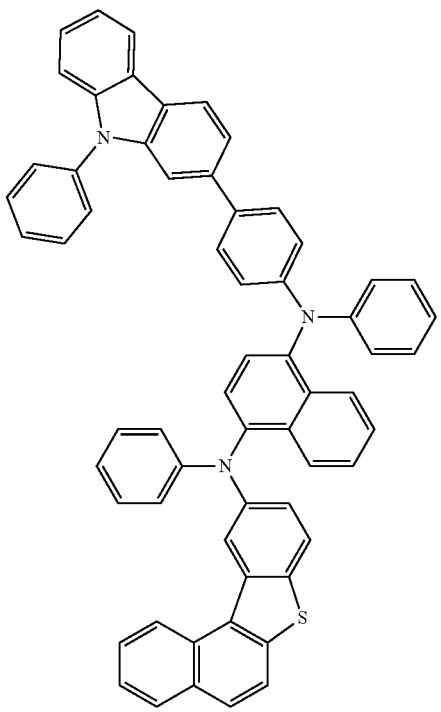

P-84
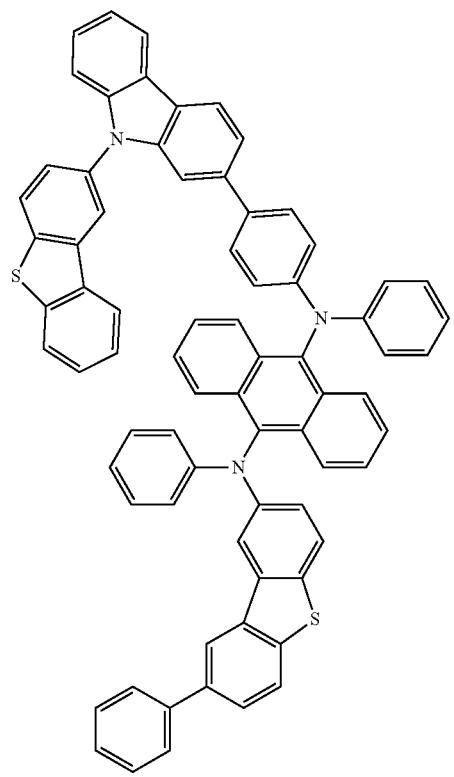
P-85
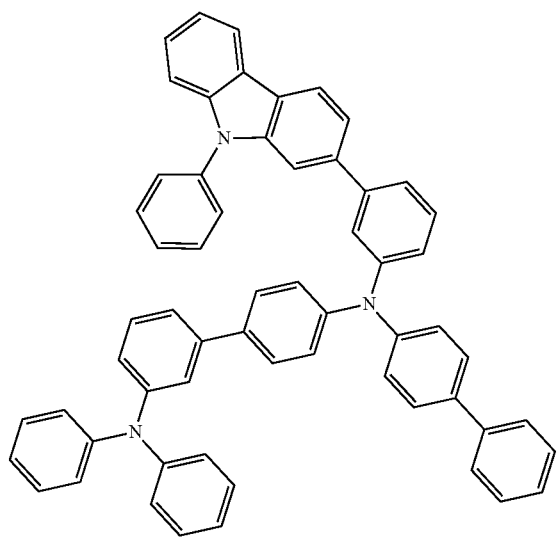
P-86
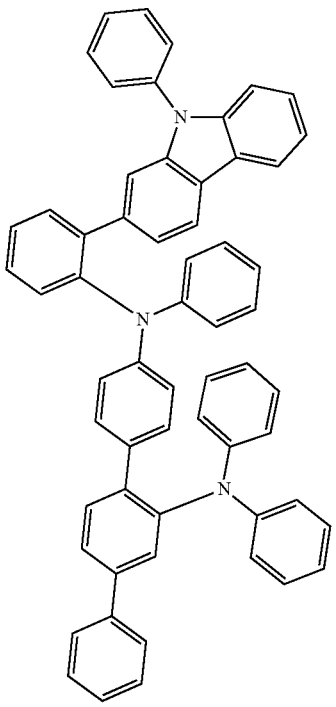
P-87
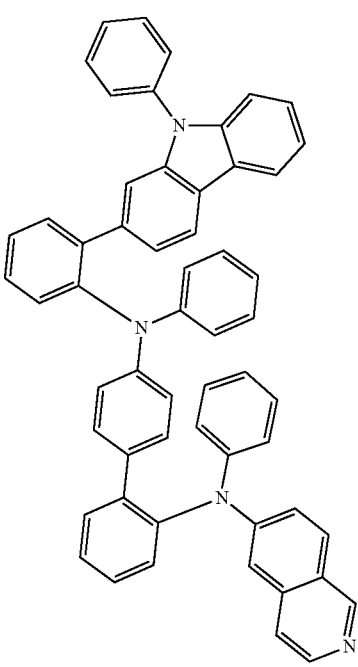

P-88
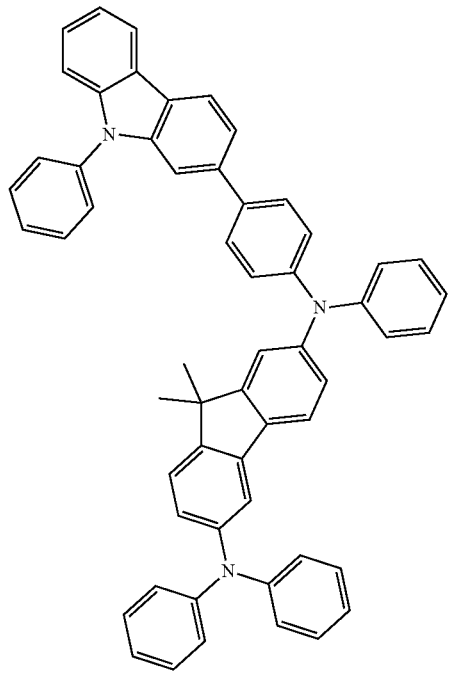
P-89
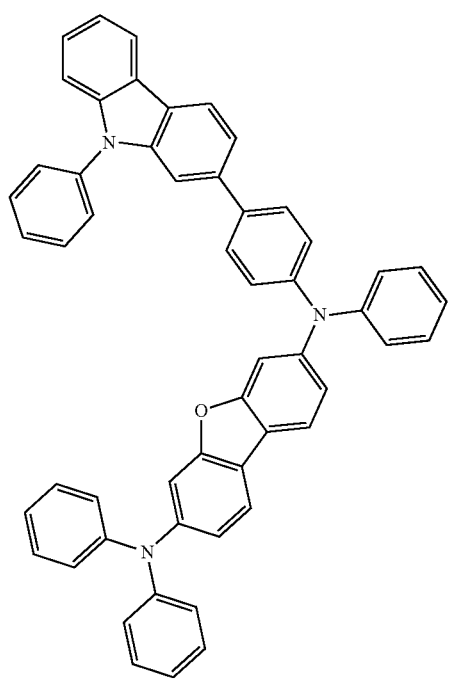
P-90
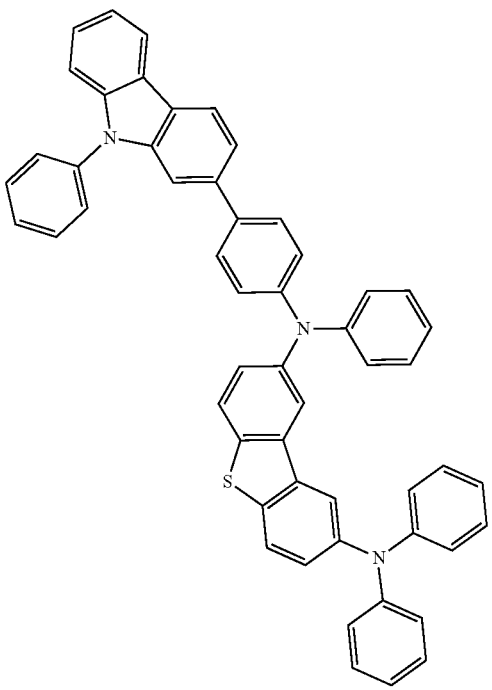
P-91
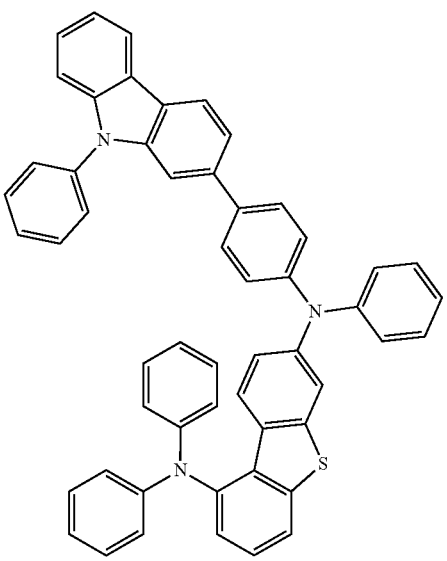

P-92
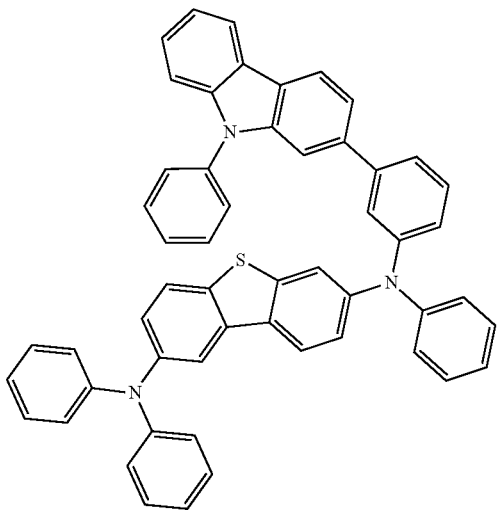
P-95
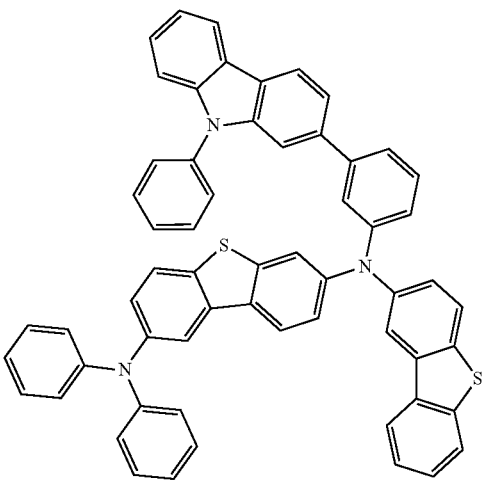
P-93
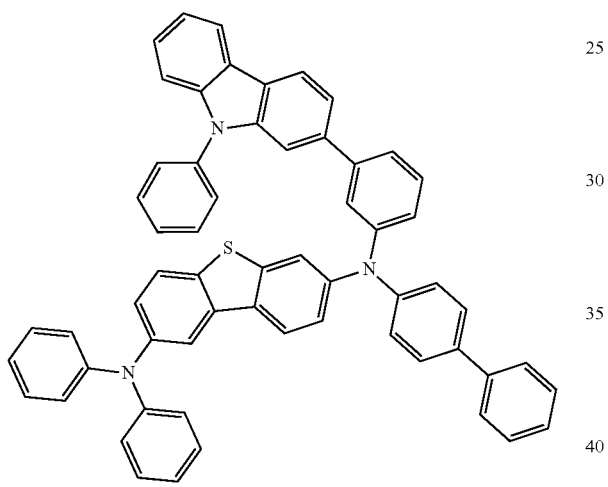
P-96
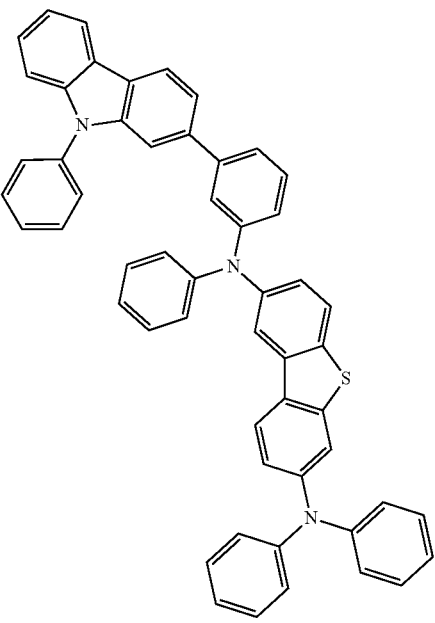
P-94

P-97
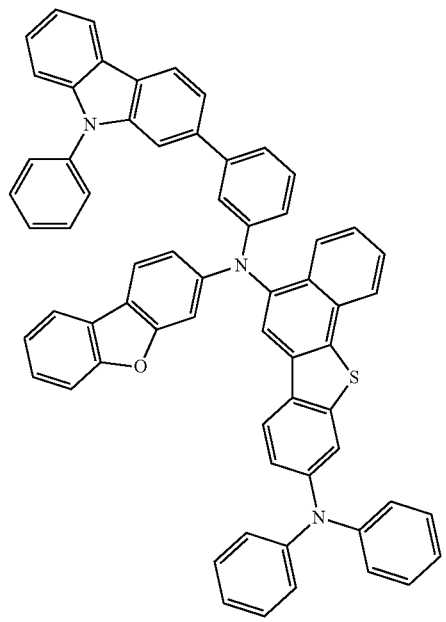
P-98
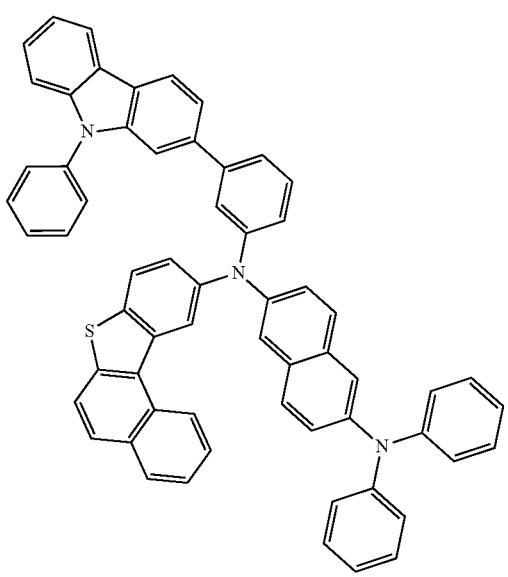
P-99
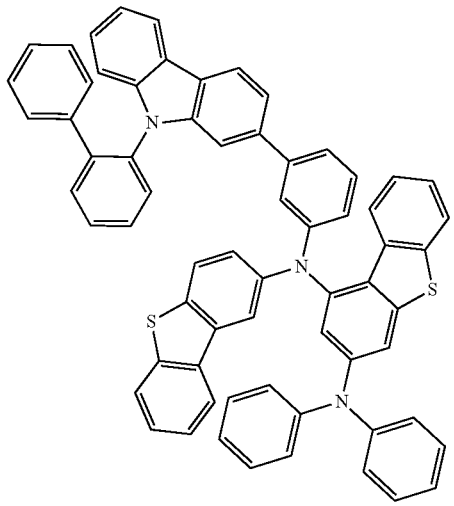
P-100
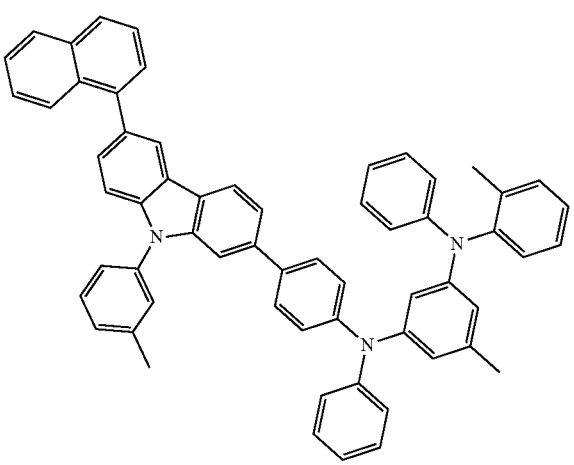

P-101
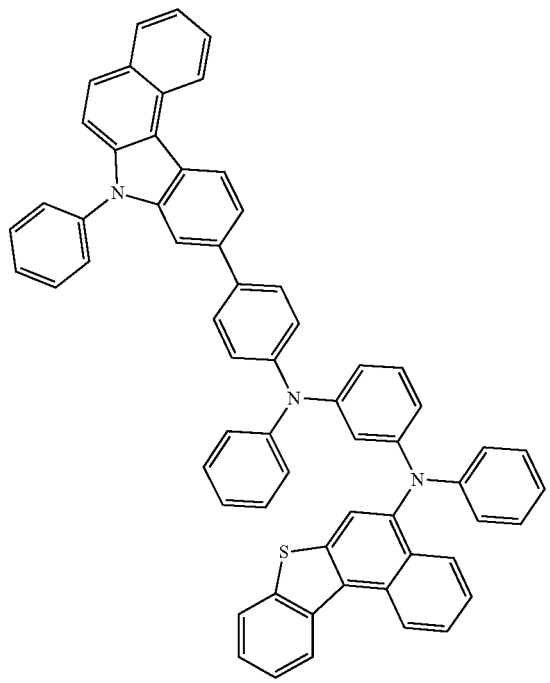
P-103
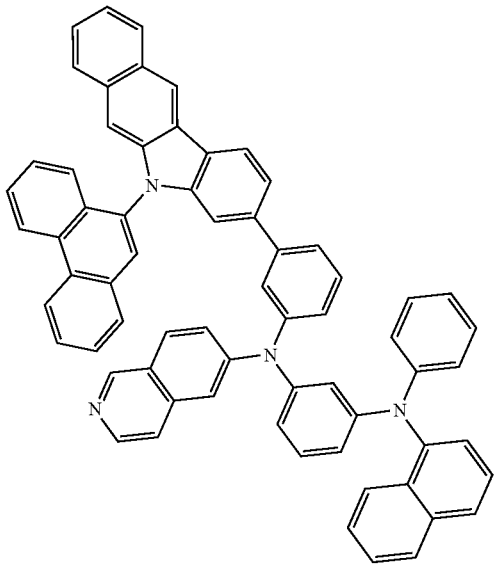
P-102
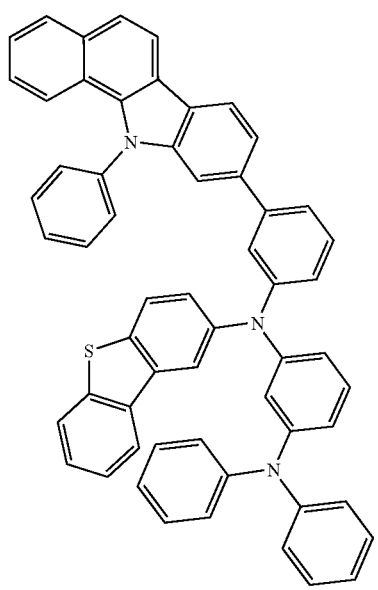
P-104
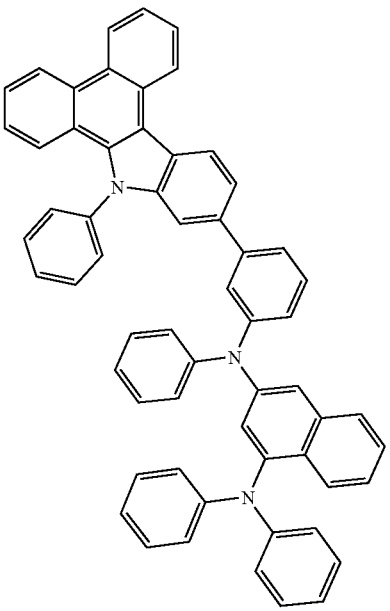

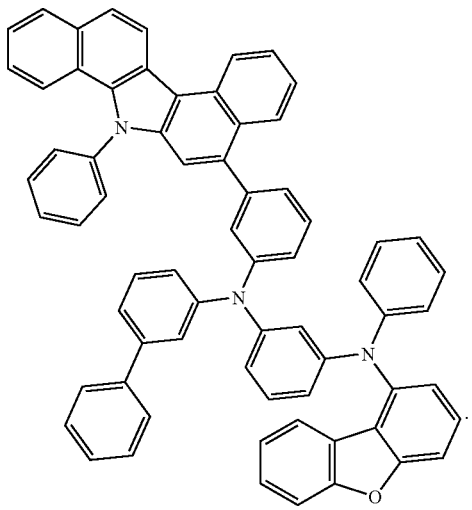

P-105

7. An organic electric element comprising a first electrode, a second electrode, and an organic material layer formed between the first electrode and the second electrode, wherein the organic material layer comprises the compound of claim 1.

8. The organic electric element of claim 7, wherein the compound is comprised in at least one layer of a hole injection layer, one or more hole transport layer, an emission-auxiliary layer, a light emitting layer, an electron transport auxiliary layer, one or more electron transport layer and an electron injection layer of the organic material layer, and the compound is comprised as a single compound or a mixture of two or more kinds in the organic material layer.

9. The organic electric element of claim 8, wherein the compound is comprised in one or more hole transport layer or one or more the emission-auxiliary layer.

10. The organic electric element of claim 7, wherein the organic material layer is formed by a process of spin coating, nozzle printing, inkjet printing, slot coating, dip coating or roll-to-roll.

11. An electronic device comprising a display device and a control unit for driving the display device, wherein the display device comprises the organic electric element of claim 7.

12. The electronic device of claim 11, wherein the organic electric element is one of an organic light emitting diode, an organic solar cell, an organic photo conductor, an organic transistor, and an element for monochromatic or white illumination.

13. An organic electric element comprising a first electrode, a second electrode, and an organic material layer formed between the first electrode and the second electrode, wherein the organic material layer comprises the compound of claim 4.

14. The organic electric element of claim 13, wherein the compound is comprised in at least one layer of a hole injection layer, one or more hole transport layer, an emission-auxiliary layer, a light emitting layer, an electron transport auxiliary layer, one or more electron transport layer and an electron injection layer of the organic material layer, and the compound is comprised as a single compound or a mixture of two or more kinds in the organic material layer.

15. An electronic device comprising a display device and a control unit for driving the display device, wherein the display device comprises the organic electric element of claim 13.

16. The electronic device of claim 15, wherein the organic electric element is one of an organic light emitting diode, an organic solar cell, an organic photo conductor, an organic transistor, and an element for monochromatic or white illumination.

17. An organic electric element comprising a first electrode, a second electrode, and an organic material layer formed between the first electrode and the second electrode, wherein the organic material layer comprises the compound of claim 6.

18. The organic electric element of claim 17, wherein the compound is comprised in at least one layer of a hole injection layer, one or more hole transport layer, an emission-auxiliary layer, a light emitting layer, an electron transport auxiliary layer, one or more electron transport layer and an electron injection layer of the organic material layer, and the compound is comprised as a single compound or a mixture of two or more kinds in the organic material layer.

19. An electronic device comprising a display device and a control unit for driving the display device, wherein the display device comprises the organic electric element of claim 17.

20. The electronic device of claim 19, wherein the organic electric element is one of an organic light emitting diode, an organic solar cell, an organic photo conductor, an organic transistor, and an element for monochromatic or white illumination.

* * * * *